US008692052B2

(12) United States Patent
Stevens et al.

(10) Patent No.: US 8,692,052 B2
(45) Date of Patent: *Apr. 8, 2014

(54) GENETICALLY MODIFIED MICE AND ENGRAFTMENT

(75) Inventors: Sean Stevens, San Diego, CA (US); Andrew J. Murphy, Croton-on-Hudson, NY (US); Richard Flavell, Guilford, CT (US); Elizabeth Eynon, New Haven, CT (US); Jorge Galan, New Haven, CT (US); Tim Willinger, New Haven, CT (US); Markus Manz, Zurich (CH); Anthony Rongvaux, New Haven, CT (US); George D. Yancopoulos, Yorktown Heights, NY (US)

(73) Assignees: Regeneron Pharmaceuticals, Tarrytown, NY (US); Yale University, New Haven, CT (US); Institute for Research in Biomedicine (IRB), Bellinzona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/617,472

(22) Filed: Sep. 14, 2012

(65) Prior Publication Data

US 2013/0022996 A1 Jan. 24, 2013

Related U.S. Application Data

(63) Continuation of application No. 12/897,517, filed on Oct. 4, 2010, now Pat. No. 8,541,646.

(60) Provisional application No. 61/249,069, filed on Oct. 6, 2009, provisional application No. 61/256,237, filed on Oct. 29, 2009, provisional application No. 61/320,132, filed on Apr. 1, 2010.

(51) Int. Cl.
*A01K 67/033* (2006.01)
*G01N 33/00* (2006.01)

(52) U.S. Cl.
USPC .................. 800/18; 800/3; 800/8; 800/13

(58) Field of Classification Search
None
See application file for complete search history.

(56) References Cited

U.S. PATENT DOCUMENTS

| | | | |
|---|---|---|---|
| 5,583,278 A | 12/1996 | Alt et al. | |
| 5,633,426 A | 5/1997 | Namikawa et al. | |
| 5,652,373 A | 7/1997 | Reisner | |
| 5,663,481 A | 9/1997 | Gallinger et al. | |
| 5,681,729 A | 10/1997 | Kudo et al. | |
| 5,709,843 A | 1/1998 | Reisner | |
| 5,750,826 A | 5/1998 | Borkowski et al. | |
| 5,849,288 A | 12/1998 | Reisner | |
| 5,866,757 A | 2/1999 | Reisner | |
| 6,018,096 A | 1/2000 | Keating et al. | |
| 6,353,150 B1 | 3/2002 | Dick et al. | |
| 6,455,756 B1 | 9/2002 | Chen et al. | |
| 7,294,754 B2 * | 11/2007 | Poueymirou et al. | ........... 800/21 |
| 8,541,646 B2 * | 9/2013 | Stevens et al. | ................. 800/9 |
| 2013/0024957 A1 * | 1/2013 | Stevens et al. | ................. 800/9 |

FOREIGN PATENT DOCUMENTS

| | | |
|---|---|---|
| EP | 0322240 | 6/1989 |
| EP | 0438053 | 7/1991 |
| EP | 0517199 | 12/1992 |
| WO | 89/12823 | 12/1989 |
| WO | 91/16910 | 11/1991 |
| WO | 91/18615 | 12/1991 |
| WO | 93/05796 | 4/1993 |
| WO | 03/018744 | 3/2003 |
| WO | 2008/069659 | 6/2008 |
| WO | 2009/042917 | 4/2009 |
| WO | 89/12823 | 3/2011 |

OTHER PUBLICATIONS

Nicolini et al. Leukemia 2004;18:341-7.*
Mittrucker et al. J Immunol 2000;164:1648-52.*
Sohn BH, et al. "Expression and characterization of bioactive human thrombopoietin in the milk of transgenic mice" DNA Cell Biol. (Nov. 1999) 18(11):845-52.
Zang WP, et al. "Transfer and Expression of Recombinant Human Thrombopoietin Gene in COS-7 Cells and Mice In Vivo" [Article in Chinese] Zhongguo Shi Yan Xue Ye Xue Za Zhi. (Mar. 2001) 9(1)14-17.
Zang W, et al., "Thrombopoietic effect of recombinant human thrombopoictin gene transferred to mice mediated by electric pulse on normal and experimental thrombocytopenia mice." [Article in Chinese] Zhonghua Xue Ye Xue Za Zhi. (Mar. 2001) 22(3):128-31.
Brehm; et al., "Parameters for establishing humanized mouse models to study human immunity: Analysis of human hematopoeitic stem cell engraftment in three immunodeficient strains of mice bearing the IL2rγ null mutation", Clinical Immunology, (2010), 135:84-98.
Cocco; et al., "CD34+ Cord Blood Cell-Transplanted Rag2-/-yc-/- Mice as a Model for Epstein-Barr Virus Infection", The American Journal of Pathology, (Nov. 2008), 173(5):1369-1378.
Greiner; et al., "Improved Engraftment of Human Spleen Cells in NOD/LtSz-scid/scid Mice as Compared with C. B-17-scid/scid Mice", American Journal of Pathology, (Apr. 1995), 146(4):888-902.

(Continued)

*Primary Examiner* — Janice Li
(74) *Attorney, Agent, or Firm* — Tor Smeland; Margarita Zippin; Elizabeth A. Alcamo

(57) ABSTRACT

A mouse with a humanization of the mIL-3 gene and the mGM-CSF gene, a knockout of a mRAG gene, and a knockout of a mIl2rg subunit gene; and optionally a humanization of the TPO gene is described. A RAG/Il2rg KO/hTPO knock-in mouse is described. A mouse engrafted with human hematopoietic stem cells (HSCs) that maintains a human immune cell (HIC) population derived from the HSCs and that is infectable by a human pathogen, e.g., *S. typhi* or *M. tuberculosis* is described. A mouse that models a human pathogen infection that is poorly modeled in mice is described, e.g., a mouse that models a human mycobacterial infection, wherein the mouse develops one or more granulomas comprising human immune cells. A mouse that comprises a human hematopoietic malignancy that originates from an early human hematopoietic cells is described, e.g., a myeloid leukemia or a myeloproliferative neoplasia.

16 Claims, 26 Drawing Sheets

(56) References Cited

OTHER PUBLICATIONS

Hofer; et al., "RAG2-/-γc-/-Mice Transplanted with CD34+ Cells from Human Cord Blood Show Low Levels of Intestinal Engraftment and Are Resistant to Rectal Transmission of Human Immunodeficiency Virus", Journal of Virology, (Dec. 2008), 82(24):12145-12153.

IWHM2 2nd International Workshop on Humanized Mice, Colorado State University, Program & Abstract Book. (Apr. 3-6, 2009, Sint Olofskapel/Amsterdam, NL.

Kondo; et al., "Lymphocyte development from hematopoietic stem cells", Current Opn Gen & Dev, (2001), 11:520-526.

Kosco-Vilbois; "A mightier mouse with human adaptive immunity", Nature Biotechnology, (Jun. 2004), 22(6):684-685.

Legrand; et al., "Humanized Mice for Modeling Human Infectious Disease: Challenges, Progress, and Outlook", Cell Host & Microbe (Jul. 23, 2009), 6:5-9.

Libby; et al., "Humanized nonobese diabetic-scid IL2rγ null mice are susceptible to lethal *Salmonella typhi* infection," PNAS, (Aug. 2010), 107(35):15589-15594.

Macchiarini; et al., Humanized mice: are we there yet?, JEM, (Nov. 2005), 202(10):1307-1311.

Manz; "Human-Hemato-Lymphoid-System Mice: Opportunities and Challenges", (May 2007), Immunity, 26:537-541.

Manz; et al., "Renaissance for mouse models of human hematopoiesis and immunohobiology," Nature Immun. (Oct. 2009) 10(10):1039-1042.

Rongvaux; "Human thrombopoietin knockin mice efficiently support human hematopoiesis", Flavell Lab, Yale University (ASH—Dec. 6, 2010).

Rongvaux; et al., "Human thrombopoietin knockin mice efficiently support human hematopoiesis in vivo". pp. 1-32.

Shultz; et al., "Human Lymphoid and Myeloid Cell Development in NOD/LtSz-scid IL2Rγ null Mice Engrafted with Mobilized Human Hempoietic Stem Cells", The Jounal of Immulogy, (2005), 174:6477-6489.

Song; et al., "A Mouse Model for the Human Pathogen *Salmonella typhi*" Cell Host & Microbe, (Oct. 21, 2010), 8:369-376.

Traggiai; et al., "Development of a Human Adaptive Immune System in Cord Blood Cell-Transplanted Mice", Science, (Apr. 2, 2004), 304:104-107.

Willinger; et al, "Human IL-3/GM-CSF knock-in mice support human alveolar macrophage development and human immune responses in the lung", Classificaton: Biological Sciences—Immunology.

Young; "Infectious disease: Tuberculosis", Eur. J. Immunol. (2009), 39:1991-2058.

Gorantla el al., "Human Immunodeficiency Virus Type 1 Pathobiology Studied in Humanized BALB/c-Rag2-/-Yc-/-Mice" Journal of Virology (Mar. 2007) 81(6):2700-2712.

Bock et al., "Improved Engraftment of Humanized Hematopoeitic Cells in Severe Combined Immunodeficient (SCID) Mice Carrying Human Cytokine Transgenes" Journal of Exp. Med. (Dec. 1995) 182:2037-2043.

Huo et al., "Humanized Mouse Model of Cooley's Anemia" J. Biol. Chem., (Feb. 20, 2009) 284(8):4889-4896.

Zhao et al., "Thrombopoietin: a potential T-helper lymphocyte stimulator. Change in T-lymphocyte composition and blood cytokine levels in thrombopoietin cDNA transferred mice" Haematolgica, (Jun. 1998) 83(6):572-573.

Biedzka-Sarek et al., "How to outwit the enemy: dendritic cells face *Salmonella*" APMIS (Sep. 2006) 114(9):589-600.

Kuruvilla et al., "Dengue virus infection and immune response in humanized RAG2-/-γc-/- (RAG-hu) mice" Virology (2007) 369:143-152.

Legrand et al., "Experimental Models to Study Development and Function of the Human Immune System in Vivo" The Journal of Immunology (2006) 176:2053-2058.

Luo et al., "Knock-in mice with chimeric human/murine p53 gene develop normally and show wild-type p53 responses to DNA damaging agents: a new biomedical research tool" Oncogene (2001) 20:320-328.

Mazurier et al., "A Novel Immunodeficient Mouse Model—RAG2 X Common Cytokine Receptor γ Chain Double Mutants—Requiring Exogenous Cytokine Administration for Human Hematopoietic Stem Cell Engraftment" Journal of Interferon and Cytokine Research (1999) 19:533-541.

Murray et al., "Thrombopoietin mobilizes CD34+ cell subsets into peripheral blood and expands multilineage progenitors in bone marrow of cancer patients with normal hematopoiesis" Experimental Hematology (1998) 26:207-216.

Rongvaux et al., "Human thrombopoietin knockin mice efficiently support human hematopoiesis in vivo" PNAS (Feb. 8, 2011) 108(6):2378-2383.

Wringer et al., "Human IL-3/GM-CSF knock-in mice support human alveolar macrophage development and human immune responses in the lung" PNAS (Feb. 8, 2011) 108(6):2390-2395.

Brehm; et al., "Parameters for establishing humanized mouse models to study human immunity: Analysis of human hematopoeitic stem cell engraftment in three immunodeficient strains of mice bearing the IL2rγ nut mutation", Clinical Immunology, (2010), 135:84-98.

Cocco; et al., "CD34+ Cord Biood Cell-Transplanted Rag2-/-γc-/-Mice as a Model for Epstein-Barr Virus Infection", The American Journal of Pathology, (Nov. 2008), 173(5):1369-1378.

Dao; et al., "Immunodeficient mice as models of human hematopoietic stem cell engraftment", Current Opinion in Immunol., (1999), 11:532-537.

Mason et al., "Alcohol Exacerbates Murine Pulmonary Tuberculosis" Infection and Immunity (May 2004) 72(5):2556-2563.

\* cited by examiner

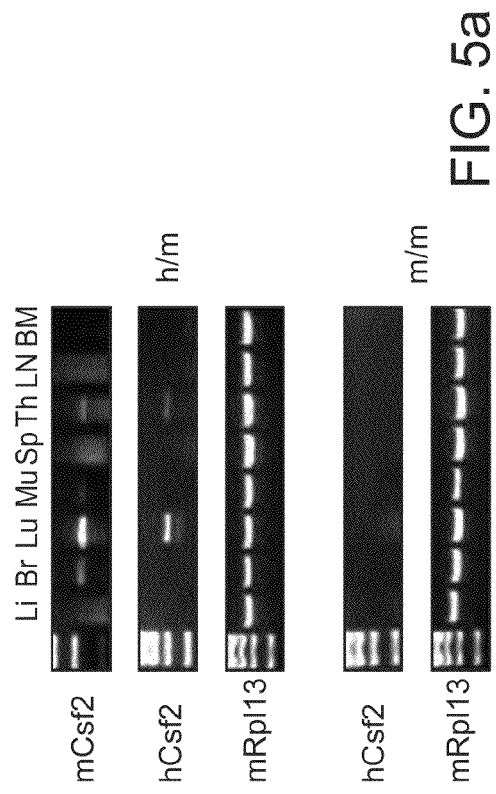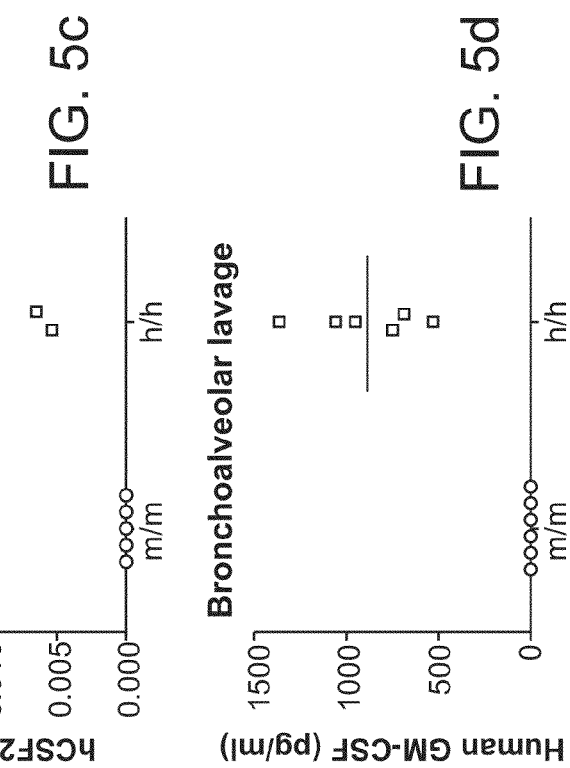
FIG. 5a
FIG. 5b
FIG. 5c
FIG. 5d

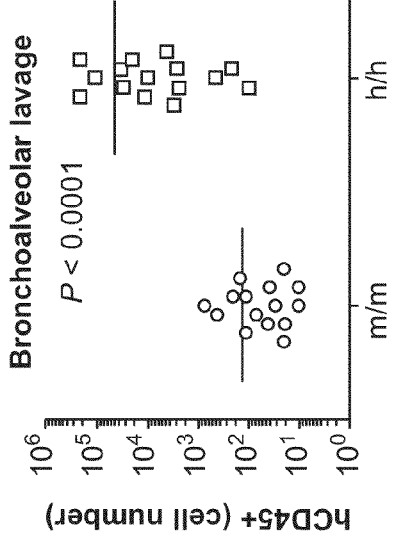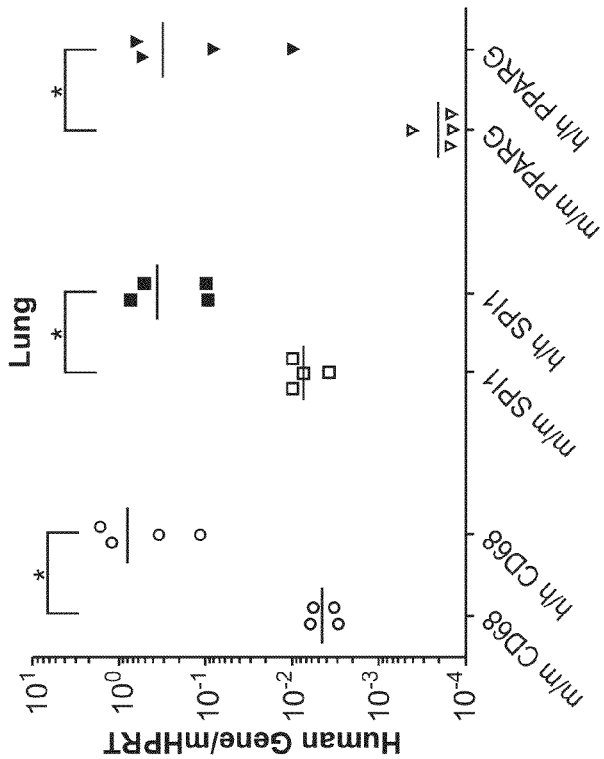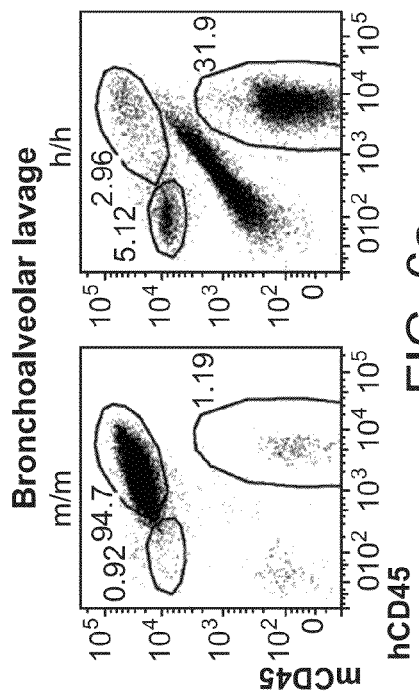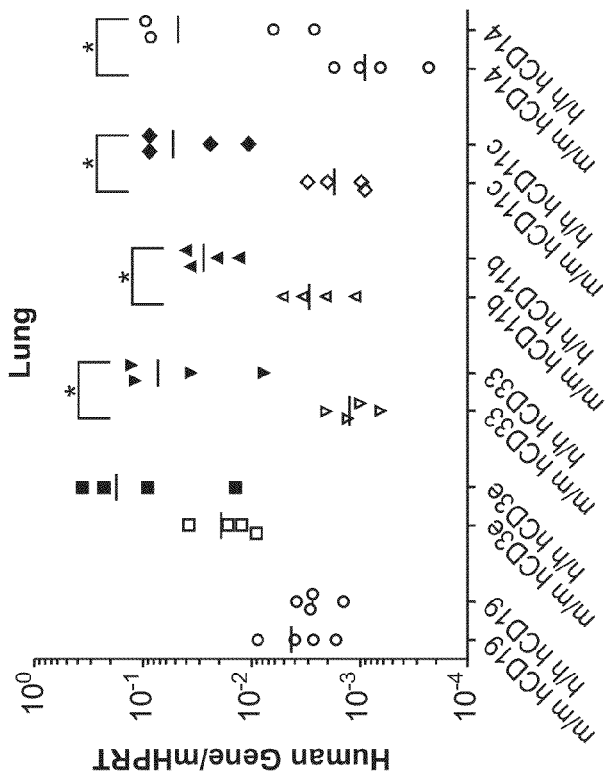
FIG. 6a
FIG. 6b
FIG. 6c
FIG. 6d

Bronchoalveolar lavage (non-engrafted mice)

Lung (non-engrafted mice)

Lung h/m (H&E)

Lung h/m (hCD45)  Lung h/m (hCD3)

Lung h/m (hCD68)  Lung h/m (hCD68)

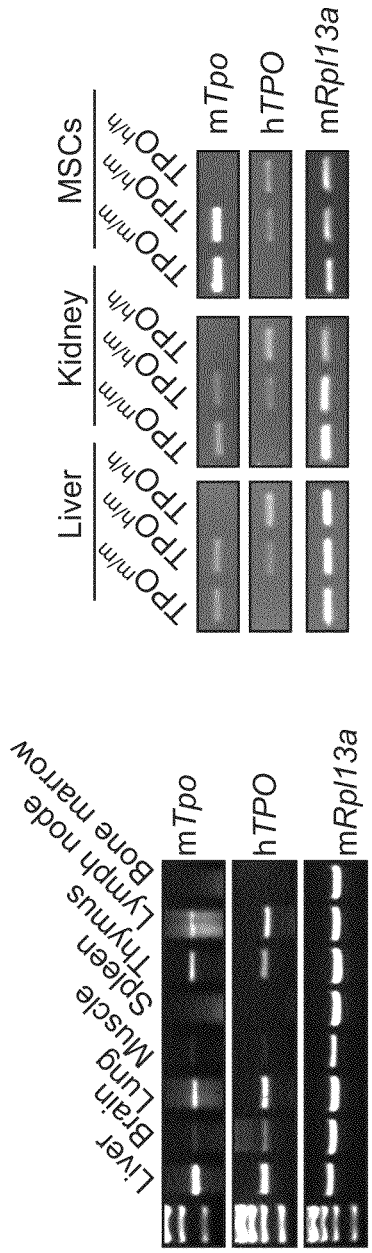
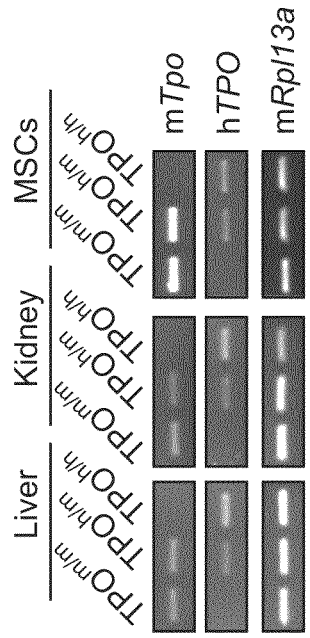
FIG. 11a
FIG. 11b
FIG. 11c

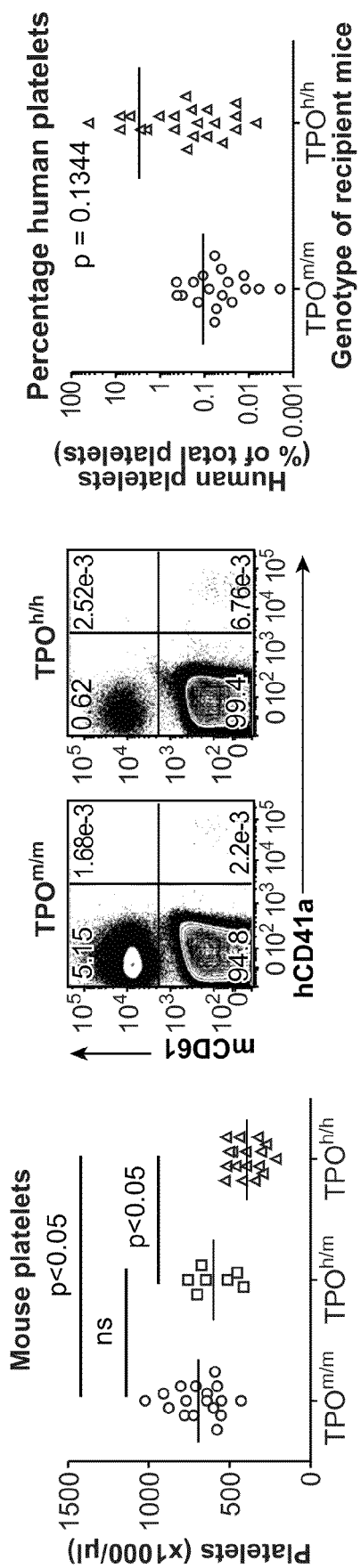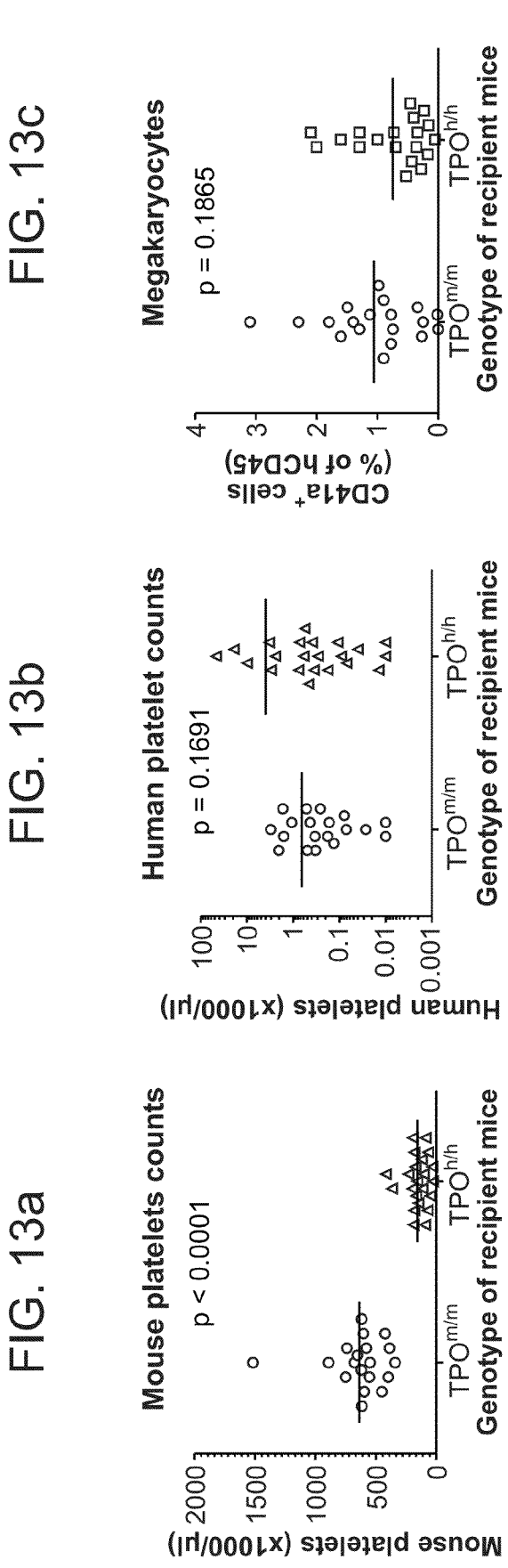
FIG. 13a, FIG. 13b, FIG. 13c, FIG. 13d, FIG. 13e, FIG. 13f

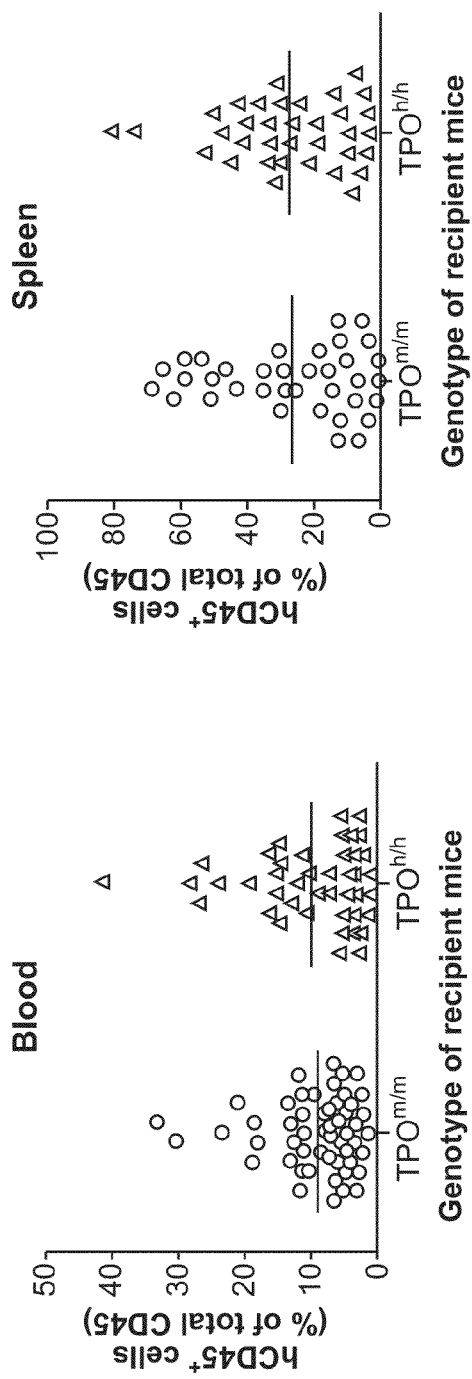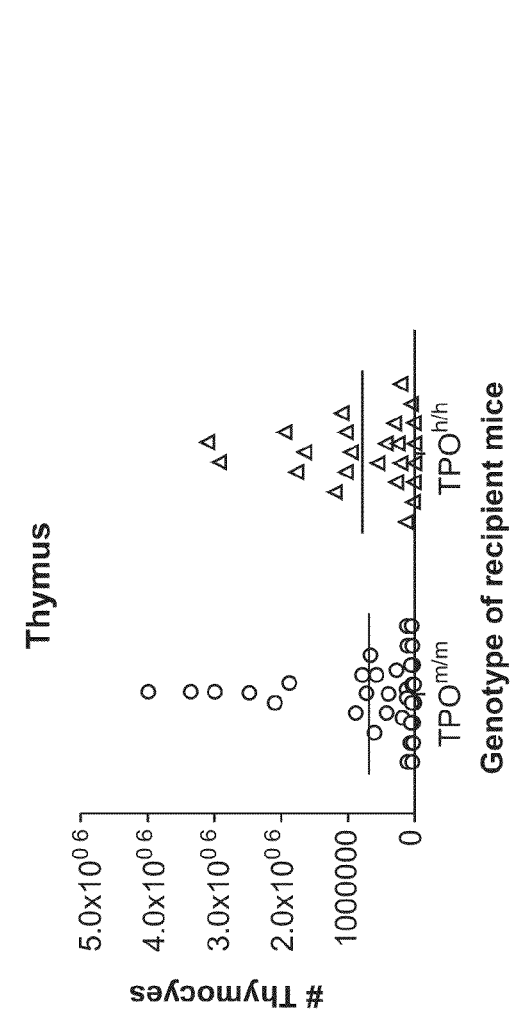
FIG. 13h
FIG. 13i
FIG. 13g

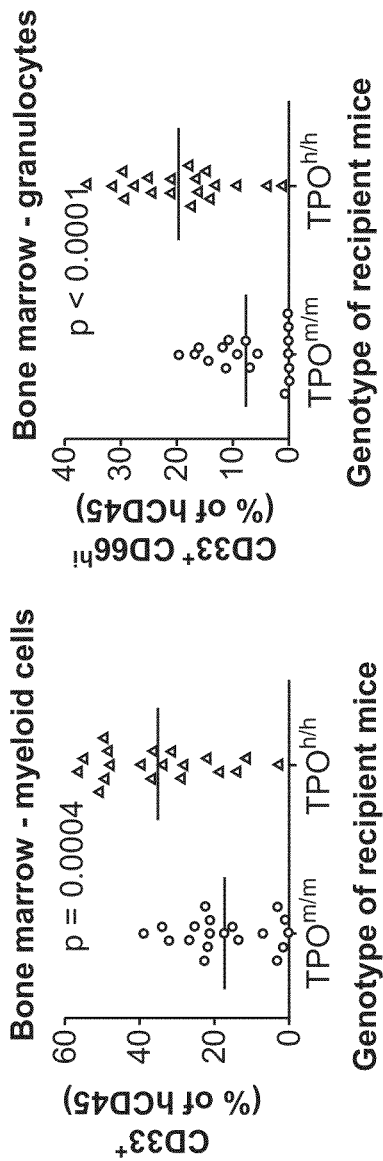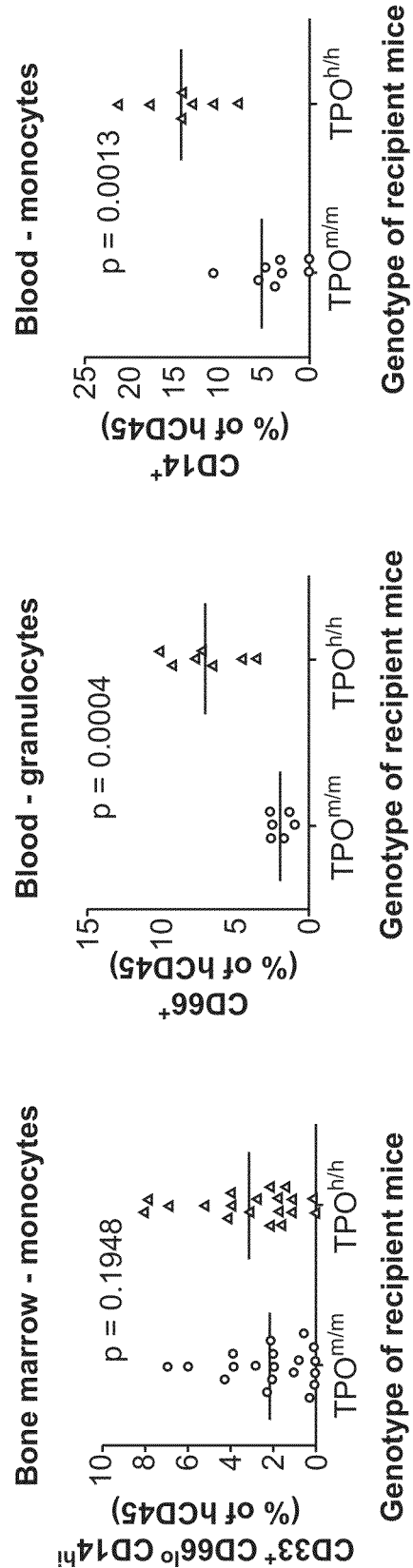
FIG. 14b, FIG. 14c, FIG. 14d, FIG. 14e, FIG. 14f, FIG. 14g

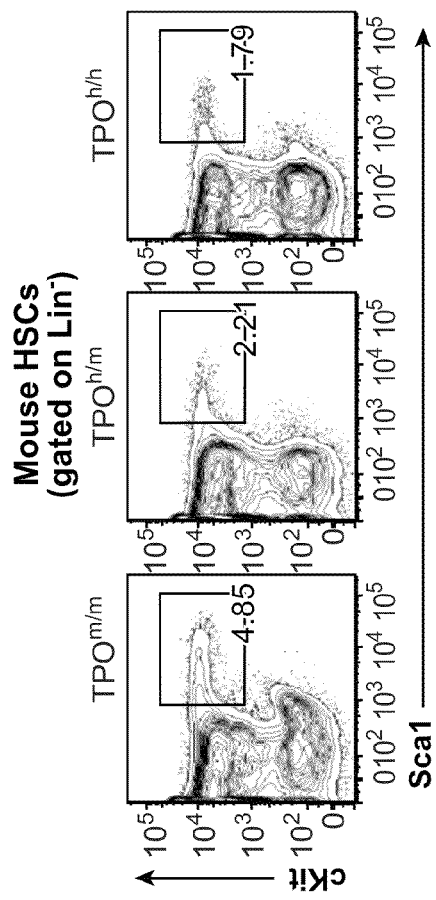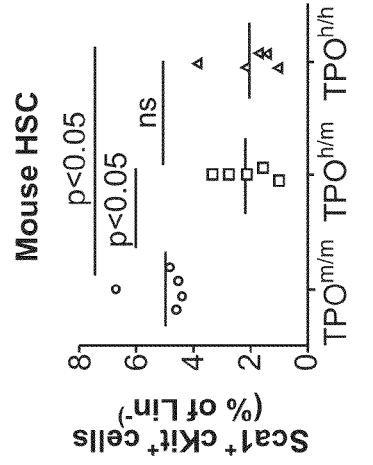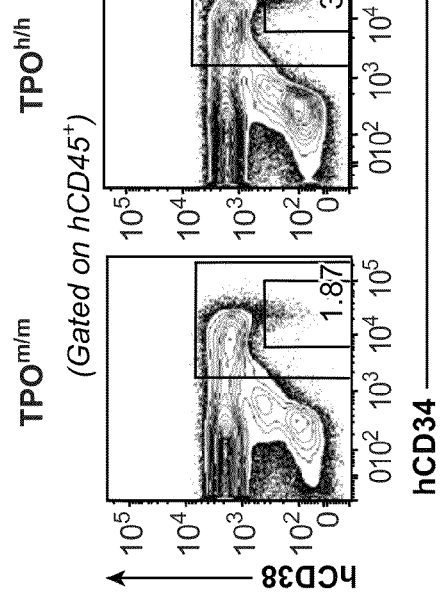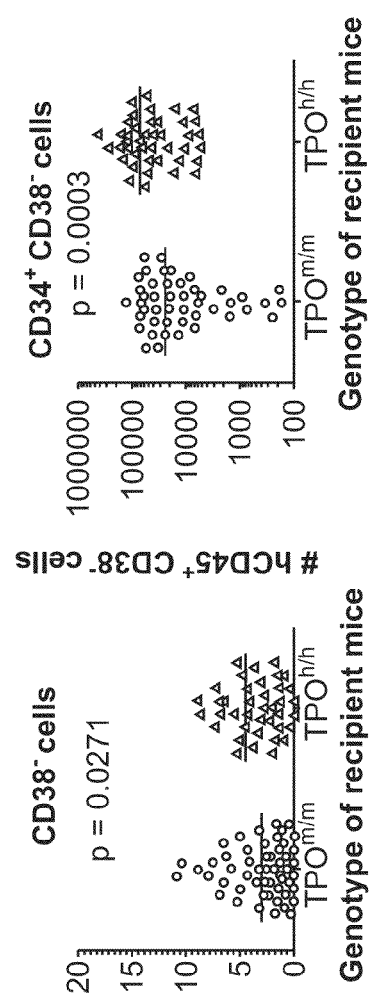
FIG. 15a
FIG. 15b
FIG. 15c
FIG. 15d
FIG. 15e

SEQUENCE LISTING

```
<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: Synthetic primer

<400> SEQUENCE: 1
ccaccaccca tggatctc                                                18

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
aaagcagaac atctggagca g                                            21
```

-continued

```
<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
caggactgaa aagggaatca                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
cgttggaagg ccttgaattt                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
gtacgctgtg aaggcatcaa                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
atcccatcca acaccttgag                                               20

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
ccagtccaaa aatgaggaag c                                             21

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
cagcgttttc agagggctat                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 9
ggcgtctcct gaacctgagt                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ggggatgaca agcagaaagt                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
gtacgctgtg aaggcatcaa                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
atcccatcca acaccttgag                                                20
```

US 8,692,052 B2

GENETICALLY MODIFIED MICE AND ENGRAFTMENT

CROSS REFERENCE

This application is a continuation of U.S. application Ser. No. 12/897,517, filed Oct. 4, 2010, now U.S. Pat. No. 8,541, 646; which claims the benefit of U.S. Provisional Application Nos. 61/249,069, filed Oct. 6, 2009; 61/256,237, filed Oct. 29, 2009; and 61/320,132, filed Apr. 1, 2010, which applications are incorporated herein by reference.

GOVERNMENT RIGHTS

This invention was made with government support under AI070949 and AI079022 awarded by National Institute of Health. The government has certain rights in the invention.

FIELD OF THE INVENTION

This invention relates to the field of genetically modified non-human animals, in particular immune-compromised mice having a RAG gene knockout, an Il2rgIl2rg gene knockout and a humanization of an IL-3 and a GM-CSF gene, and optionally a humanization of a TPO gene; RAG/Il2rgIl2rg knockout mice having a humanization of a TPO gene; genetically modified mice that are engrafted with human hematopoietic cells; and engrafted mice that are infected with a human pathogen, e.g., Salmonella typhi or Mycobacterium tuberculosis.

BACKGROUND

Genetically modified mice, modified and engrafted mice, and their use in modeling human diseases, e.g., for the purpose of drug testing, are known in the art. Attempts have been made to use genetically modified mice to model a human immune system. A review of that field is provided in Manz (2007) Human-Hemato-Lympoid-System Mice: Opportunities and Challenges, Immunity, 26:537-541 hereby incorporated by reference.

To date no genetically modified mice have been generated that demonstrate infectivity with certain human pathogens, e.g., Salmonella typhi (S. typhi). Even for pathogenic infections for which mouse models exist, the models can fail to adequately model certain pathologies in humans, e.g., failure to form well-defined granulomas or granulomas containing human immune cells in mouse models of Mycobacterium tuberculosis (M. tuberculosis). In order to study the effects of certain pathogens on humans, and to test drugs for effectiveness in treating humans infected with certain pathogens, it would be useful to have a non-human animal such as a mouse that is genetically modified so that it is susceptible to infection with such a pathogen, e.g., S. typhi, and/or that the infection more closely models human pathology, e.g., more closely models a human infection of M. tuberculosis.

In general, there is a need for genetically modified mice that can support maintenance and propagation of human hematopoietic stem cells, and for mice suitable for engraftment that can model or approximate certain aspects of a human hemato-lymphoid system, e.g., in response to a human pathogen.

SUMMARY

Genetically modified non-human animals are provided. The non-human animals include mice that comprise one or more knockouts of endogenous genes and one or more humanized genes (i.e., replacement of an endogenous gene at its endogenous locus with a human ortholog or homolog).

Genetically modified mice with ablated or compromised immune systems are provided (e.g., via irradiation), as well as mice engrafted with human hematopoietic cells or human hematopoietic stem and progenitor cells (HSPC). Genetically modified mice that comprise a human cell derived from a human hematopoietic cell or HSPC are provided, as are mice that comprise a human hemato-lymphoid system.

Genetically modified, irradiated, and engrafted mice are provided that are infectable with a human pathogen that does not infect wild-type mice. Mice are provided that in response to a human pathogen exposure (e.g., M. tuberculosis) mount an immune response having characteristics (e.g., formation of well-defined granulomas, or granulomas comprising human immune cells) that are not observed in wild-type mice.

Genetically modified, irradiated, and engrafted mice for identifying drug-resistant strains of human pathogens, for testing human vaccines, and for developing and testing anti-pathogen drugs are provided, as well as compositions and methods for using them.

Genetically modified mice capable of receiving and propagating human immune cells are provided, including mice that can sustain a human hematopoietic malignancy.

In one aspect, a genetically modified mouse is provided, comprising: (a) a mouse RAG gene knockout; (b) a mouse Il2rgIl2rg gene knockout; and, (c) a humanization of one or more mouse genes selected from (i) a mouse IL-3 (mIL-3) gene, (ii) a mouse GM-CSF (mGM-CSF) gene, and (iii) a mouse thrombopoietin (mTPO) gene.

In one embodiment, the RAG gene knockout is a RAG2 gene knockout.

In one embodiment, the humanization comprises replacement of a mTPO gene with a hTPO gene. In a specific embodiment, the humanization consists essentially of humanization of a mTPO gene with a hTPO gene.

In one embodiment, the humanization comprises replacement of a mIL-3 gene with a human IL-3 (hIL-3) gene and replacement of a mGM-CSF gene with a human GM-CSF (hGM-CSF) gene. In another embodiment, the mouse further comprises replacement of a mTPO gene with a human TPO (hTPO) gene. In a specific embodiment, the humanization consists essentially of humanization of a mIL-3 gene with a hIL-3 gene and humanization of a mGM-CSF gene with a hGM-CSF gene.

In one embodiment, the humanization comprises a replacement of a mGM-CSF gene with a human GM-CSF gene, and in the mouse human GM-CSF is not predominantly expressed in liver and circulation. In one embodiment, human GM-CSF is predominantly expressed in the mouse lung. In one embodiment, human GM-CSF expression is tissue-specific and reflects tissue specific expression in a human.

In one embodiment, the genetically modified mouse is treated so as to eliminate endogenous hematopoietic cells that may exist in the mouse. In one embodiment, the treatment comprises irradiating the genetically modified mouse. In a specific embodiment, newborn genetically modified mouse pups are irradated sublethally. In a specific embodiment, newborn pups are irradiated 2×200 cGy with a four hour interval.

In one embodiment, the genetically modified and treated mouse is engrafted with human hematopoietic cells or human hematopoietic stem cells (HPSCs) to form a genetically modified and engrafted mouse. In one embodiment, the hematopoietic cells are selected from human umbilical cord blood cells and human fetal liver cells. In one embodiment, engraftment is with about 1–2×10$^5$ human CD34+ cells.

In one embodiment, the genetically modified and engrafted mouse gives rise to a human cell selected from a CD34+ cell, a hematopoietic stem cell, a hematopoeitic cell, a myeloid precursor cell, a myeloid cell, a dendritic cell, a monocyte, a granulocyte, a neutrophil, a mast cell, a thymocyte, a T cell, a B cell, a platelet, and a combination thereof. In one embodiment, the human cell is present at 4 months, 5 months, 6 months, 7 months, 8 months, 9 months, 10 months, 11 months, or 12 months after engraftment.

In one embodiment, the genetically modified and engrafted mouse gives rise to a human hemato-lymphoid system that comprises human hematopoietic stem and progenitor cells, human myeloid progenitor cells, human myeloid cells, human dendritic cells, human monocytes, human granulocytes, human neutrophils, human mast cells, human thymocytes, human T cells, human B cells, and human platelets. In one embodiment, the human hemato-lymphoid system is present at 4 months, 5 months, 6 months, 7 months, 8 months, 9 months, 10 months, 11 months, or 12 months after engraftment.

In one embodiment, the genetically modified and engrafted mouse exhibits an inflammatory response mediated by a human cell. In a specific embodiment, the human cell is a macrophage. In a specific embodiment, the macrophage-mediated inflammatory response is mediated by an alveolar macrophage. In a specific embodiment, the response mediated by the alveolar macrophage comprises a granuloma formation. In a specific embodiment, the granuloma comprises a human immune cell. In a specific embodiment, the granuloma is a well-organized granuloma. In a specific embodiment, the granuloma forms following exposure to a mycobacterium, e.g., $M.\ tuberculosis$. In one embodiment, the mouse exhibits an inflammatory response that comprises two or more granulomas. In one embodiment, the genetically modified and engrafted mouse is a model for human $M.\ tuberculosis$ infection.

In one embodiment, the genetically modified and engrafted mouse comprises an $M.\ tuberculosis$ infection characterized at least in part by the formation of a granuloma that comprises a human immune cell. In a specific embodiment, the granuloma is a well-organized granuloma. In a specific embodiment, the $M.\ tuberculosis$ is a drug-resistant or multidrug-resistant strain of $M.\ tuberculosis$ that infects a human population. In one embodiment, the mouse infected with $M.\ tuberculosis$ comprises a granuloma in a lung. In a specific embodiment, the granuloma is a well-developed granuloma. In a specific embodiment, the granuloma in the lung comprises human immune cells. In a specific embodiment the human immune cells of the granuloma are selected from an activated human macrophage, an activated human T cell, and a combination thereof.

In one embodiment, the genetically modified and engrafted mouse exhibits enhanced mucosal immunity as compared with an engrafted mouse that lacks a humanization of one or more of IL-3, GM-CSF, and TPO genes. In a specific embodiment, the enhanced mucosal immunity comprises an enhanced expression of interferon β (IFNβ) following influenza A infection.

In one embodiment, the genetically modified and engrafted mouse comprises an infection selected from a $M.\ tuberculosis$ and a $S.\ typhi$ infection. In one embodiment, the mouse reproduces $S.\ typhi$ or $M.\ tuberculosis$. In one embodiment, the mouse mounts an anti-mycobacterial immune response to a human pathogenic mycobacterium, wherein the response comprises formation of a granuloma mediated by human immune cells and that comprises a human immune cell. In a specific embodiment, the granuloma is a well-developed granuloma.

In one embodiment, the genetically modified and engrafted mouse comprises a humanization that comprises humanization of a mTPO gene to form a hTPO engrafted mouse. In one embodiment, the hTPO engrafted mouse exhibits an increase of human meyloid cells in bone marrow over an engrafted mouse that comprises a mTPO gene but no hTPO gene. In a specific embodiment, the human myeloid cells are increased 1.5-fold, 2-fold, 2.5-fold, or 3-fold over an engrafted mouse that lacks a hTPO gene. In a specific embodiment, the increase in granulocytes is about 1.5-fold, 2-fold, 2.5-fold, or 3-fold. In another embodiment, an increase in peripheral blood monocytes is observed over an engrafted mouse that lacks a hTPO gene, wherein the increase in peripheral blood monocytes is about 1.5-fold, 2-fold, 2.5-fold, or 3-fold. In one embodiment, the genetically modified engrafted mouse comprises a humanization that consists essentially of a hTPO gene that replaces a mTPO gene, wherein the mouse does not express a mouse TPO but expresses a human TPO.

In one aspect, a genetically modified and engrafted mouse is provided, comprising a knockout of a Rag gene, an Il2rgIl2rg knockout, and a humanization of TPO, wherein the mouse is engrafted with human hematopoietic stem cells, or human immune cells, and comprises a human hematopoietic malignancy that originates from an early human hematopoietic cell. In a specific embodiment, the malignancy is selected from a myeloid leukemia and a myeloproliferative neoplasia.

In one embodiment, the mouse further comprises a human IL-3 gene and a human GM-CSF gene, and a knockout of an endogenous mouse IL-3 gene and a knockout of an endogenous mouse GM-CSF gene.

In one aspect, a mouse is provided that comprises a RAG gene knockout, an Il2rg gene knockout, and a genetic modification that provides human myeloid cells with a competitive advantage with respect to mouse myeloid cells. In one embodiment, the genetic modification is a replacement of a mouse gene required for mouse myeloid cell development and/or maintenance with a counterpart human gene. In one embodiment, the genetic modification is selected from a replacement of a mouse IL-3 gene with a human IL-3 gene, replacement of a mouse GM-CSF gene with a human GM-CSF gene, and a combination thereof. In one embodiment, the mouse lacks or substantially lacks endogenous mouse hematopoietic cells and comprises human hematopoietic cells.

In one aspect, a method for making a mouse that is infectable with a human pathogen is provided, comprising genetically modifying and engrafting a mouse as described herein and exposing the genetically modified and engrafted mouse to a human pathogen, and maintaining the mouse under conditions sufficient for the human pathogen to infect the mouse. In one embodiment, the human pathogen is selected from $M.\ tuberculosis$ and $S.\ typhi$. In one embodiment, the human pathogen is a human pathogen that is not pathogenic in a mouse that lacks the genetic modification(s). In one embodiment, the human pathogen is a human pathogen that does not infect a mouse that lacks the genetic modification(s).

In one aspect, a method for determining the effect of a drug on a human pathogen is provided, comprising exposing a genetically modified and engrafted mouse as described herein to a human pathogen, allowing the pathogen to infect the mouse, and measuring a parameter of the infection over time in the presence and in the absence of the drug. In one embodiment, the human pathogen is a pathogen that does not infect a mouse that lacks the genetic modification(s). In one embodiment, the human pathogen is selected from *M. tuberculosis* and *S. typhi*. In one embodiment, the mouse is exposed to a known number of infectious units of the human pathogen, and the parameter of infection is the number of infectious units of the human pathogen in a fluid or tissue of the mouse.

In one embodiment, the parameter of the infection is a titer in a body fluid of the mouse. In one embodiment, the infection is selected from an *M. tuberculosis* infection and a *S. typhi* infection. In a specific embodiment, the infection is an *M. tuberculosis* infection and the parameter is formation of a granuloma. In a specific embodiment, the granuloma is a lung granuloma. In another specific embodiment, the granuloma is a well-defined granuloma.

In one aspect, a genetically modified mouse is provided, comprising: (a) a mouse RAG gene knockout; (b) a mouse Il2rg gene knockout; and, (c) a humanization of (i) a mouse IL-3 (mIL-3) gene, and a (ii) a mouse GM-CSF (mGM-CSF) gene; wherein the mouse following irradiation to ablate endogenous mouse hematopoietic cells and following engraftment with human hematopoietic stem cells maintains the human hematopoietic stem cells and develops from the human hematopoietic stem cells a human immune cell population that comprises functional differentiated human immune cells that include human myeloid progenitor cells, human myeloid cells, human dendritic cells, human monocytes, human granulocytes, human neutrophils, human mast cells, human thymocytes, human T cells, human B cells, and human platelets. In another aspect the mouse further comprises (iii) a humanization of a mouse thrombopoietin (mTPO) gene.

In one embodiment, the mouse maintains a population of human immune cells that is as diverse in cell type as the population of immune cells in a human. In one embodiment, the human immune cells are maintained for at least at 4 months, 5 months, 6 months, 7 months, 8 months, 9 months, 10 months, 11 months, or 12 months after engraftment.

In one embodiment, the mouse upon exposure to a human pathogen or antigen of a human pathogen mounts a cellular and/or humoral immune response that models infection of a human exposed to the pathogen. In one embodiment, the human pathogen is a pathogen that does not infect a wild-type mouse. In another embodiment, the human pathogen is a pathogen that infects a wild-type mouse, wherein the wild-type mouse following infection does not model an immune response that a human mounts in response to the pathogen. In one embodiment, the pathogen is a virus, a mycobacterium, a fungus, or a bacterium. In specific embodiments, the pathogen is a human or porcine or avian influenza virus, *S. typhi*, or *M. tuberculosis*.

Further applications and embodiments of the invention will become apparent to those skilled in the art upon reading this disclosure.

BRIEF DESCRIPTION OF THE DRAWINGS

FIG. 5(*e*) shows a humanization strategy at a mouse IL-3/GM-CSF locus.

FIG. 6(*f*),(*g*) shows ELISA results for mouse and human IL-3 (*f*) and GM-CSF (g) production by activated splenocytes.

FIG. 9(*f*) shows DiffQuick™ staining of BAL cells from non-engrafted m/m or h/h KI mice; magnification 400×; (*g*) PAS staining of lung tissue sections from non-engrafted m/m or h/h KI mice; magnification 400×.

FIG. 11(*d*) shows a targeting construct for replacing mTPO gene with hTPO gene.

FIG. 13(a) shows platelet counts in the blood of adult non-engrafted Rag2$^{-/-}\gamma_c^{-/-}$TPO$^{m/m}$, TPO$^{h/m}$ and TPO$^{h/h}$ mice; (b) representative FACS analysis of mouse (mCD61+) and human (hCD41a+) platelets in the blood of Rag2$^{-/-}\gamma_c^{-/-}$TPO$^{m/m}$ and TPO$^{h/h}$ mice 3 to 4 months after engraftment; (c) human platelet chimerism, determined by FACS, in TPO$^{m/m}$ and TPO$^{h/h}$ mice; (d),(e) counts of mouse (mCD61+, 20d) and human (hCD41a+, 20e) platelets in the blood of TPO$^{m/m}$ and TPO$^{h/h}$ recipients; (f) human megakoryocyte percentages (CD41a+) among human CD45+ cells in the bone marrow.

FIG. 13(g),(h) shows percentages of human CD45+ cells in blood and spleen of Rag2$^{-/-}\gamma_c^{-/-}$TPO$^{m/m}$ and TPO$^{h/h}$ mice; (i) provides total cellularity of the thymi of engrafted TPO$^{m/m}$ and TPO$^{h/h}$ recipients.

DETAILED DESCRIPTION

Figure 1:
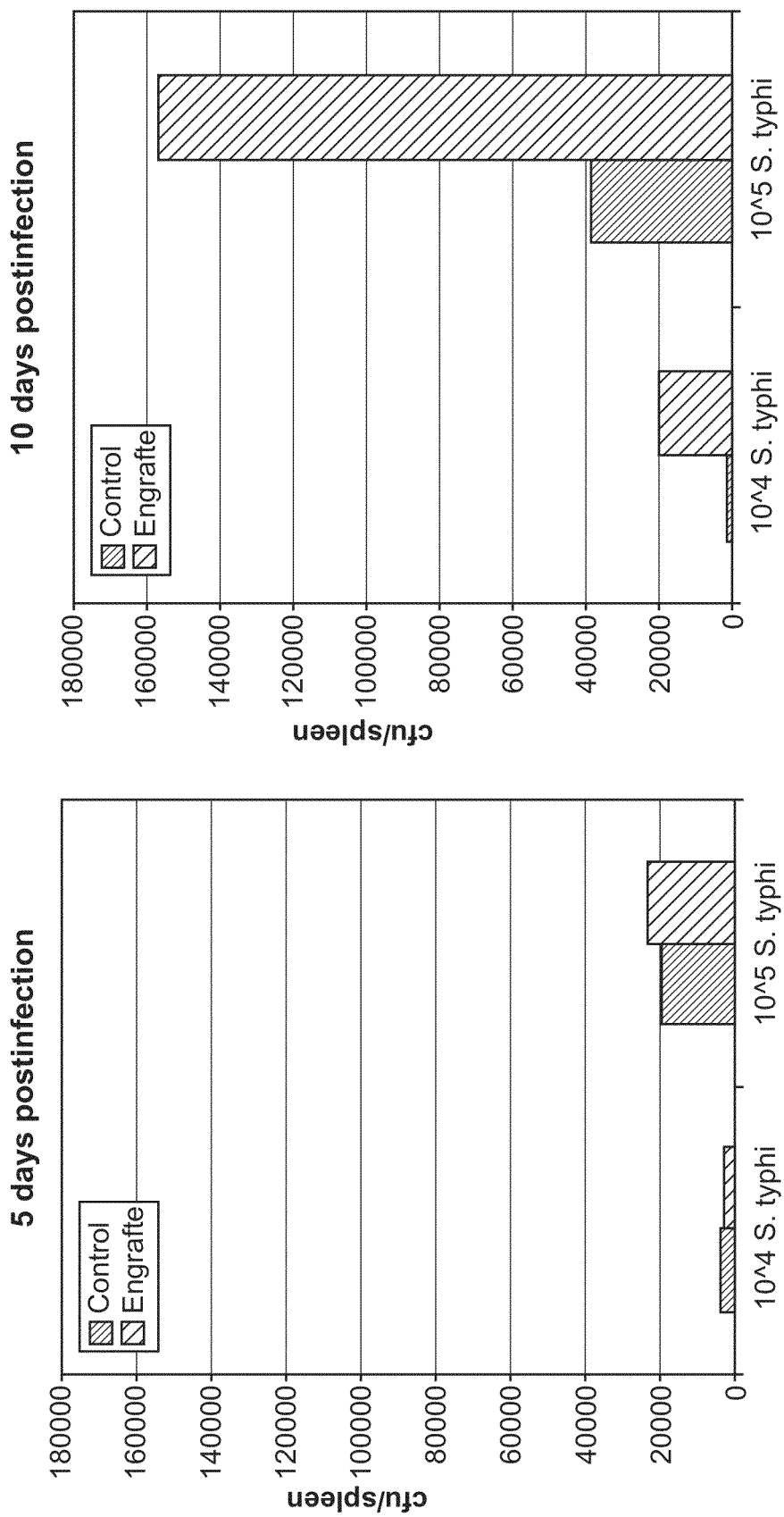
FIG. 1 shows *S. typhi* infection in engrafted RAG KO, Il2rg KO and RAG KO, Il2rg KO, hIL-3/hGM-CSF mice ten days post-infection. Experimental groups: (1) Engrafted: n=9 (4 m/m, 5 h/m); engraftment in blood=6.5-16.7%; (2) Control: n=8; engraftment in blood=0.04-0.4% (reflects flow cytometry background; Control mice were unengrafted).

The invention is not limited to particular embodiments discussed, but is described by the granted claims.

Unless otherwise specified, all technical and scientific terms used herein include the same meaning as commonly understood by one of ordinary skill in the art to which the invention belongs. Although any methods and materials similar or equivalent to those described can be used in making or using the invention, particular embodiments, methods, and materials are now described. All publications mentioned are hereby incorporated by reference. The present disclosure supersedes any disclosure of an incorporated publication to the extent that a contradiction exists.

The singular forms "a", "an", and "the" include plural referents unless the context clearly dictates otherwise. Thus, for example, reference to "a gene" includes a plurality of such genes and reference to "the gene knockout" includes reference to one or more knockouts and equivalents thereof.

Modified Mice that Support Human Immune Cells: hIL-3/GM-CSF Mice

Mice with components of the human immune system (HIS mice) hold great promise for studying the human immune system in vivo and for testing human vaccines and testing and developing drugs to treat human diseases and disorders. HIS mice are generated by transplanting a severely immunodeficient mouse strain (such as recombination-activating gene 2 (Rag2) knockout (KO) interleukin 2 receptor gamma (Il2rg) KO mice) with human hematopoietic stem and progenitor cells. Compared to nonhuman primates, HIS mice have the advantages of a small animal model, i.e., they allow more versatile experimentation, are more accessible to the research community, and are ethically more acceptable than conducting experiments with human subjects. Most importantly, experimental findings derived from HIS mice might be more relevant and applicable to humans, because infection with human-specific pathogens and the study of human-specific immune responses and immunopathologies are now becoming feasible.

Although much progress has been made in recent years, current HIS mice models have several major limitations such as the poor development, maintenance, and function of human myeloid and T cells. As a consequence, human inflammatory and immune responses at mucosal surfaces or robust human T cell-mediated responses, such as delayed-type hypersensitivity (DTH), have rarely been observed. Thus, current HIS mice are not well suited to study infection and pathology caused by the serious human pathogen *Mycobacterium tuberculosis*. Indeed, granulomas—specifically granulomas containing human cells, a hallmark of the human immune response to mycobacteria—have so far not been reported in HIS mice (see, e.g., Manz et al. (2009) Renaissance for mouse models of human hematopoiesis and immunobiology, *Nat. Immunol*. 10:1039-1042).

Current HIS mouse hosts are not well suited to model certain infections, at least in part because current HIS mouse hosts present a non-physiological environment for human cells. Several mouse cytokines, e.g., IL-3 and GM-CSF, do not act on the human cognate receptors. In addition, Rag2 KO Il2rg KO mice have an intact mouse myeloid compartment, and human myeloid cells might have a competitive disadvantage relative to host cells. To overcome these limitations, this disclosure describes generating human cytokine knock-in mice where genes encoding mouse cytokines are replaced by their human counterparts. Criteria for cytokine replacement are: (1) the mouse cytokine does not or weakly act on human cells; (2) the human cytokine does not or weakly act on mouse cells to confer competitive advantage to human cells; (3) the human cytokine is not exclusively produced by hematopoietic (transplanted) cells; (4) lack of the mouse cytokine is not lethal to mouse host, or the human KI cytokine is sufficiently cross-reactive to rescue the mouse KO phenotype. The KI strategy should allow faithful expression in appropriate organs and at physiologic concentrations. Importantly, in homozygous KI mice, human cognate receptor expressing cells should gain a competitive advantage over respective mouse cells.

IL-3 and GM-CSF are two cytokines crucial for myeloid cell development and function. Neither cytokine is cross-reactive between human and mouse. IL-3 stimulates early hematopoietic progenitors in vitro, but is dispensable for steady-state hematopoiesis in vivo. However, together with GM-CSF it is required for effective DTH responses in vivo. IL-3 also specifically stimulates the proliferation of alveolar macrophages (AM) in vitro. GM-CSF is highly expressed in the lung and important for lung homeostasis in vivo, as demonstrated by the fact that GM-CSF KO mice develop pulmonary alveolar proteinosis (PAP) which is characterized by protein accumulation in the lung due to defective surfactant clearance. Alveolar macrophages from GM-CSF KO mice have a defect in terminal differentiation, which leads to impaired innate immunity to pathogens in the lung. GM-CSF also stimulates the proliferation of human AM in vitro. Similar to IL-3, GM-CSF is largely dispensable for steady-state hematopoiesis, and the same applies to mice lacking both cytokines. In contrast, GM-CSF is required for inflammatory responses such as the production of pro-inflammatory cytokines by macrophages and the mobilization and recruitment of monocytes. GM-CSF is also essential for protective immunity against a range of pathogens, including M. tuberculosis. In particular, GM-CSF KO mice infected with M. tuberculosis do not develop granulomas, a hallmark of tuberculosis.

This disclosure is based at least in part on the realization that generating hIL-3/GM-CSF KI mice would be valuable to support human myeloid cell reconstitution and function as well as human innate immune responses to pathogens in mice. Results obtained and described in this disclosure with such KI mice demonstrate that this strategy affords a substantial improvement over current models of HIS mice in terms of human myeloid cell development, human lung mucosal immunity, and also granuloma formation after mycobacterial infection. These and other beneficial properties of such mice are discussed elsewhere in this disclosure.

The ability to study human tissue in an in vivo setting in mice has opened a wide range of possible avenues of research. Major limitations have hindered the application of the approach and of these one of the most important deficiencies has been the inability of mouse factors to support human cells. Indeed, in the immune system, many essential factors required for human immune cell development and function are species-specific and cannot be effectively provided by the mouse. It was therefore decided to follow a strategy of replacing the mouse genes with their human counterparts, enabling the better development and function of human cells and potentially disabling the same of the corresponding mouse cells. By applying this concept to human cytokine KI mice, proof of concept is provided here that replacement of immune genes in the mouse host with human genes improves HIS mice. Specifically, this disclosure supports the notion that inappropriate cytokine crossreactivity between mouse and human, and having to compete with mouse cells, indeed limit engraftment and function of human myeloid cells in current HIS mice.

Human cytokines can be delivered to HIS mice by intravenous injection, e.g., to boost human NK cell and T cell reconstitution by injections of IL-15/IL-15Rα complexes and IL-7, respectively. Another approach is the hydrodynamic injection of plasmid DNA expressing human cytokines, which leads to transient expression in the liver. This approach has very recently been used to improve reconstitution of human DC by hydrodynamic delivery of GM-CSF and IL-4 (see, Chen et al. (2009) Expression of human cytokines dramatically improves reconstitution of specific human-blood lineage cells in humanized mice, *Proc Natl Acad Sci USA*, 106(51): 21783-21788). In contrast to the present disclosure, no functional responses of myeloid cells or in vivo responses to pathogens were reported in these mice. Finally, human cytokines can also be overexpressed as transgenes in HIS mice. This approach has been used to generate human IL-3/GM-CSF/stem cell factor (SCF) transgenic (tg) mice (see, Nicolini et al. (2004) NOD/SCID mice engineered to express human IL-3, GM-CSF and Steel factor constitutively mobilize engrafted human progenitors and compromise human stem cell regeneration, *Leukemia* 18:341-347). In these mice human cytokine expression is driven by the cytomegalovirus promoter, which leads to ubiquitous expression. However, hIL-3/GM-CSF/SCF tg HIS mice are hampered by reduced maintenance of human hematopoietic stem cells in bone marrow and expanded terminal myelopoiesis. Again, unlike the present disclosure, improved myeloid cell function or in vivo responses were not described. By contrast, in the system described here, physiologic expression of the targeted genes in steady state and inflammation enables appropriate development and function of the appropriate cell type only. Importantly, the approach described in this disclosure generates strains of mice that can be maintained and propagated under highly reproducible conditions and made available worldwide for studies.

The hIL-3/GM-CSF KI mice described in this disclosure represent a considerable improvement over previous HIS mice and the alternative approaches discussed above. First, delivery of human IL-3 and GM-CSF by the KI strategy described here leads to long-term cytokine expression, which circumvents the need for repeated injections of expensive cytokines. Second, faithful expression in organs where IL-3 and GM-CSF are normally expressed is achieved. Under physiological conditions, GM-CSF is mainly expressed in the lung (FIG. 5a). In contrast, hydrodynamic delivery leads to predominant expression in the liver and in the circulation. In both organs GM-CSF is not expressed in steady-state conditions. Third, physiological amounts of IL-3 and GM-CSF are expressed in KI mice in contrast to delivery by hydrodynamic injection or ubiquitous overexpression in hIL-3/GM-CSF/SCF tg mice. It has been demonstrated that physiological levels of GM-CSF are important for a protective immune response against M. tuberculosis. Thus, transgenic mice with local overexpression of GM-CSF in the lung show defective granuloma formation and increased susceptibility to M. tuberculosis. Similarly, intravenous administration of GM-CSF also leads to impaired control of M. tuberculosis infection in mice. Fourth, homozygous hIL-3/GM-CSF KI mice allow the simultaneous impairment of the mouse myeloid compartment since mouse IL-3 and GM-CSF are not expressed in homozygous mice. This leads to a competitive advantage for human myeloid cells as shown in the present disclosure.

Tuberculosis caused by infection with M. tuberculosis results in 1.7 million deaths per year. Therefore, novel effective preventive and therapeutic measures are urgently needed. While mice can be infected with M. tuberculosis, they do not represent an ideal model for human tuberculosis. This is due to species-specific differences in the immune response to M. tuberculosis. For example, infected mice do not develop well-organized granulomas. Granulomas are the hallmark of the immune response in humans with tuberculosis and contain activated macrophages that fuse to form epithelioid and multinucleated giant cells, and activated T cells. Granulomas play an important role in limiting bacterial replication and in controlling spread of mycobacteria. GM-CSF promotes the differentiation of AM into multinucleated giant cells in vitro. Studies in transgenic mice also revealed a role for GM-CSF in the fusion of macrophages to form multinucleated giant cells in vivo. Furthermore, GM-CSF is essential for granuloma formation after mycobacterial infection. Absence of granulomas in GM-CSF KO mice infected with M. tuberculosis is associated with increased bacterial replication and reduced survival. Finally, humans with PAP, caused by defective GM-CSF signaling, show increased susceptibility to mycobacterial infections.

Human anti-mycobacterial immune responses, particularly formation of granulomas by human cells, have not been previously reported in HIS mice. This is likely due to weak human macrophage and T cell responses. In this disclosure, an antigen-specific T cell response to mycobacteria was detected in a subset of mice engrafted with human cells. In addition, given the prominent role of GM-CSF in granuloma biology, it is hypothesized that engrafted hIL-3/GM-CSF KI mice would be a better host to support granuloma formation. This was indeed the case in at least a subset of mice infected with BCG. Importantly, lung granulomas in these mice contained human T cells and human macrophages, although the granulomas had the loose architecture typical of mouse granulomas. Future efforts should aim to further boost human T cell and macrophage responses in HIS mice. This should lead to the development of a small animal model that allows the study of human immune responses to $M.$ $tuberculosis$ in vivo. hIL-3/GM-CSF KI mice could also be useful in other settings to study the human immune response in vivo. This includes infection with pulmonary pathogens, autoimmunity, and human cancers. In summary, the hIL-3/GM-CSF KI mice presented in the current disclosure represent a considerable improved HIS mouse model that should serve as a versatile tool for future studies.

Modified Mice that Support Human Immune Cells: hTPO

Hematopoietic stem cells (HSCs) are characterized by two major properties: life-long self-renewal, and differentiation capacity to all mature hematopoietic lineage cells. To ensure HSC pool homeostasis, it is believed that upon cell division, HSCs generate one functional HSC while the other offspring cell might undergo a highly organized program of differentiation and cellular expansion, during which multiple lineages of committed progenitors, and ultimately terminally differentiated cells are produced.

Mouse hematopoiesis has been extensively studied during the past decades, leading to the identification and functional characterization of immuno-phenotypically defined cellular populations, highly enriched in stem and progenitor cells in vivo. However, prospective experimental in vivo studies of human hematopoiesis have been limited by obvious practical and ethical restrictions.

To circumvent this limitation, several xenogeneic transplantation models for in vivo human hematopoiesis studies have been developed. Of these, transplantation of human hematopoietic cells into immunodeficient mice has been broadly established in experimental hematopoiesis laboratories. The models most commonly used today rely on the BALB/c Rag2$^{-/-}\gamma_c^{-/-}$ or NOD-SCID $\gamma_c^{-/-}$ strains of mice. Both strains are highly immunodeficient, lacking B, T and NK cells, and their genetic background is permissive for human hematopoietic engraftment and differentiation. Upon human CD34$^+$ hematopoietic stem and progenitor cell transplantation, most human hematopoietic populations (including B cells, T cells, monocytes, dendritic cells, erythrocytes and platelets) can develop and are detectable in these models. However in those chimeric animals, there is a bias towards lymphoid development with initially high B cell counts that typically represent up to 80% of human cells, myelo-monocytic development is minor, and engraftment levels usually start to decline 4-6 months after transplantation. Moreover, the xenogenic engraftment of human cells into mice requires transplantation of large numbers of cells compared to numbers sufficient for the optimal engraftment of mouse hematopoietic stem and progenitor cells into mice, or human cells into humans, respectively. Furthermore, in contrast to mouse HSCs transplanted into mouse recipients, human HSCs do not expand, nor are they maintained, in the xenogeneic mouse environment. Thus the mouse background does not provide an optimal environment to study the physiology of human HSCs. This might be due to absence or limited cross-reactivity of growth factors, required to support the function and maintenance of HSCs.

Thrombopoietin (TPO) was initially identified as a growth factor that promotes the development of megakaryocytes and platelets. TPO is constitutively produced by the liver and the kidneys and released into the blood circulation. The receptor for TPO, c-Mpl, is expressed by hematopoietic stem and progenitor cells in the bone marrow. C-Mpl is also expressed on circulating platelets. However, the binding of TPO on platelets does not activate any signaling pathway. Thus, thrombocytes act as a sink or scavengers for TPO and via this mechanism contribute to negative regulation of thrombopoiesis. Subsequently, TPO has been recognized for its important function to support the expansion and self-renewal of HSCs. TPO deficiency leads to reduced numbers of HSCs in adult mice, and the presence of TPO is needed to maintain adult HSCs in quiescence. Furthermore, TPO is required to support post-transplantation expansion of HSCs, necessary to replenish the hematopoietic compartment of irradiated hosts. Interestingly, it has been demonstrated that osteoblastic cells involved in forming the HSC niche in the bone marrow produce TPO, critical for HSC function and maintenance.

Although mouse and human TPO are both-sided cross-reactive to the respective cognate receptors when used at supraphysiological doses in vitro, affinity and biologic activity might differ when the cytokine acts at limiting, physiological doses in context of an in vivo environment. Thus, mouse TPO might not provide an appropriate stimulus to the human c-Mpl receptor in vivo, and therefore could account for the impaired properties of human HSCs in the mouse environment. To correct this potential defect, the gene encoding mouse TPO was replaced by its human counterpart in Rag2$^{-/-}$ $\gamma_c^{-/-}$ mice.

This disclosure is based at least in part on the realization that generating hTPO KI mice in a RAG2$^{-/-}\gamma_c^{-/-}$ background would be valuable to support human myeloid cell reconstitution and function as well as human innate immune responses to pathogens in mice, in the mice themselves and in the progeny of such mice bred with hIL-3/GM-CSF mice. Results obtained from hTPO KI mice in a RAG2$^{-/-}\gamma_c^{-/-}$ background are described in this disclosure. Homozygous hTPO KI mice had significantly increased levels of human engraftment in bone marrow, and multilineage differentiation of hematopoietic cells was improved over mTPO mice, the hTPO KI mice displaying an increased ratio of myelomonocytic vs. lymphoid lineages. Both the number and self-renewal capacity of human stem and progenitor cells were improved, as demonstrated by serial transplantation. Thus, among other applications, hTPO KI mice are useful for propagation of human cells by serial transplantation.

Breeding a hIL-3/GM-CSF Mouse and a hTPO Mouse

Progeny of hIL-3/GM-CSF and hTPO mice described herein are expected to have at least the same relevant characteristics and display at least the same benefits as parental lines (La, hIL-3/GM-CSF mice and hTPO mice). For example, human cell populations from either parental strain, or both, or such a progeny can be isolated and serially transplanted into either a hTPO mouse or a progeny of an hIL-3/GM-CSF and hTPO mouse. Thus, in one aspect, a genetically modified mouse is provided that is a progeny of a hIL-3/GM-CSF mouse and a hTPO mouse as described herein (including progeny that are bred to homozygosity with respect to each relevant gene) and wherein the genetically modified mouse exhibits the benefits and characteristics of both a hIL-3/GM-CSF mouse and a hTPO mouse. In one aspect, such a progeny mouse is provided that comprises an ablated immune system (e.g., an irradiated mouse), and is suitable for engraftment and/or serial transplantation from any engrafted mouse (e.g., an engrafted mouse as described herein).

Engrafting Genetically Modified Mice

A genetically modified mouse in accordance with the invention finds one use as a recipient of human hematopoietic cells that is capable of developing human immune cells from engrafted human hematopoietic cells. In one embodiment, human hematopoietic cells or human hematopoietic stem and progenitor cells (HSPC) are placed (engrafted) in a genetically modified and irradiated mouse in accordance with the invention. The human hematopoietic cells or human hematopoietic stem cells give rise in the genetically modified mouse to a cell selected from a human CD34-positive cell, a human hematopoietic stem cell, a human hematopoietic cell, a myeloid precursor cell, a myeloid cell, a dendritic cell, a monocyte, a neutrophil, a mast cell, and a human hemato-lymphoid system (including human hematopoietic stem and progenitor cells, human myeloid progenitor cells, human myeloid cells, human dendritic cells, human monocytes, human granulocytes, human neutrophils, human mast cells, human thymocytes, human T cells, human B cells, human platelets), and a combination thereof.

The genetically modified mice can be irradiated to eliminate endogenous hematopoietic cells that may be present, and the mouse can be engrafted with any suitable source of human hematopoietic cells. One suitable source of hematopoietic cells known in the art is human umbilical cord blood cells, in particular CD34-positive cells. Another source of hematopoietic cells is human fetal liver.

In one embodiment, engraftment of a mouse in accordance with the invention with human hematopoietic cells results in a mouse that exhibits an enhanced number of human hematopoietic cells than an immune-compromised mouse that lacks the humanization of a TPO gene, lacks humanization of a IL-3 and a GM-CSF gene, or lacks humanization of a TPO gene and a IL-3 and a GM-CSF gene.

In one embodiment, engraftment of a mouse in accordance with the invention with human hematopoietic cells results in a mouse that exhibits an enhanced number of human blood cells (e.g., mature hematopoietic cells) as compared with an immune-compromised mouse that lacks the humanization(s). In a specific embodiment, the human hematopoietic cells are selected from human CD34-positive cells, hematopoietic stem cells, hematopoietic cells, myeloid precursor cells, myeloid cells, dendritic cells, monocytes, granulocytes, neutrophils, mast cells, and a human hemato-lymphoid system (including human hematopoietic stem and progenitor cells, human myeloid progenitor cells, human myeloid cells, human dendritic cells, human monocytes, human granulocytes, human neutrophils, human mast cells, human thymocytes, human T cells, human B cells, human platelets), and a combination thereof.

Nonlimiting Applications of Genetically Modified Engrafted Mice

A genetically modified mouse engrafted with human hematopoieitic cells is a useful animal in which to study pathogens that do not normally infect mice. One such example is the causative agent of typhoid fever, S. typhi.

Typhoid fever afflicts over 21 million people around the world—principally in the developing world—including about 400 cases/year in the United States. Typhoid fever has been treated with the drugs amoxicillin, ampicillin, cefotaxime, ceftriaxone, ceftazidime, chloramphenicol, ciprofloxacin, co-trimoxazole, ertapenem, imipenem, fluoroquinolones (e.g., ciprofloxacin, gatifloxacin, ofloxacin), streptomycin, sulfadiazine, sulfamethoxazole, tetracycline, and combinations thereof. Recurrent infections are common, which limits disease management by antibiotic therapy. Further, multi-drug resistance is also prevalent with S. typhi infections.

New therapeutics, new vaccines, and new ways of testing efficacy of therapeutics and vaccines are needed. A mouse capable of being infected by S. typhi, for example, would be useful to identify new therapeutics and new vaccines. New therapeutics and new vaccines could be testing in such a mouse by, e.g., determining the amount of S. typhi in the mouse (in blood or a given tissue) in response to treatment with a putative anti-S. typhi agent, or by inoculating the mouse with a putative vaccine followed by exposure to an infective administration of S. typhi, and observing any change in infectivity due to inoculation by the putative vaccine as compared to a control not inoculated with the vaccine but infected with S. typhi.

A genetically modified and engrafted mouse in accordance with the invention is useful to make a mouse that is infectable by a human pathogen that does not infect mice. For example, the mouse is useful as a non-human animal infectable by S. typhi. In one embodiment, the genetically modified and engrafted mouse displays an enhanced engraftment of human cells as compared to an engrafted mouse that lacks the genetic modification(s), wherein the enhancement is sufficient to maintain a S. typhi infection. In a specific embodiment, maintenance of a S. typhi infection includes the ability of S. typhi to reproduce in the mouse. In a specific embodiment, the S. typhi infection includes the ability of the infected mouse to reproduce S. typhi. In a specific embodiment, the mouse is capable of reproducing S. typhi at least a week, 10 days, two weeks, three weeks, or four weeks following an initial introduction or infective exposure of S. typhi.

A method for identifying an anti-S. typhi agent, is also provided, wherein the method employs a mouse as described herein that is infectable by S. typhi. Wild-type mice, and other known immune-compromised mice (e.g., RAG1/RAG2 gene knockout mice) are not capable of being infected by S. typhi.

A genetically modified mouse comprising an Il2rg gene knockout and a RAG gene knockout (e.g., a RAG 2 gene knockout) (first type) and also comprising a replacement of the endogenous mouse IL-3 gene with a human IL-3 gene and the endogenous mouse GM-CSF gene with a human GM-CSF gene (second type) is provided, wherein the genetically modified mouse when engrafted with human hematopoietic cells is capable of infection with S. typhi.

The data shown in FIG. 1 is representative of both the first and the second type of mouse. Genetic modifications of the mice in FIG. 1 comprise: (a) a mouse RAG gene knockout; and (b) a mouse Il2rg gene knockout. The FIG. 1 mice also comprise an engraftment of human hematopoietic cells. The mice may be further modified by two further modifications to create the second type of mouse, which are: (c) replacement of an endogenous mouse IL-3 gene with a human IL-3 gene; and (d) replacement of a mouse GM-CSF gene with a human GM-CSF gene.

Figure 2:
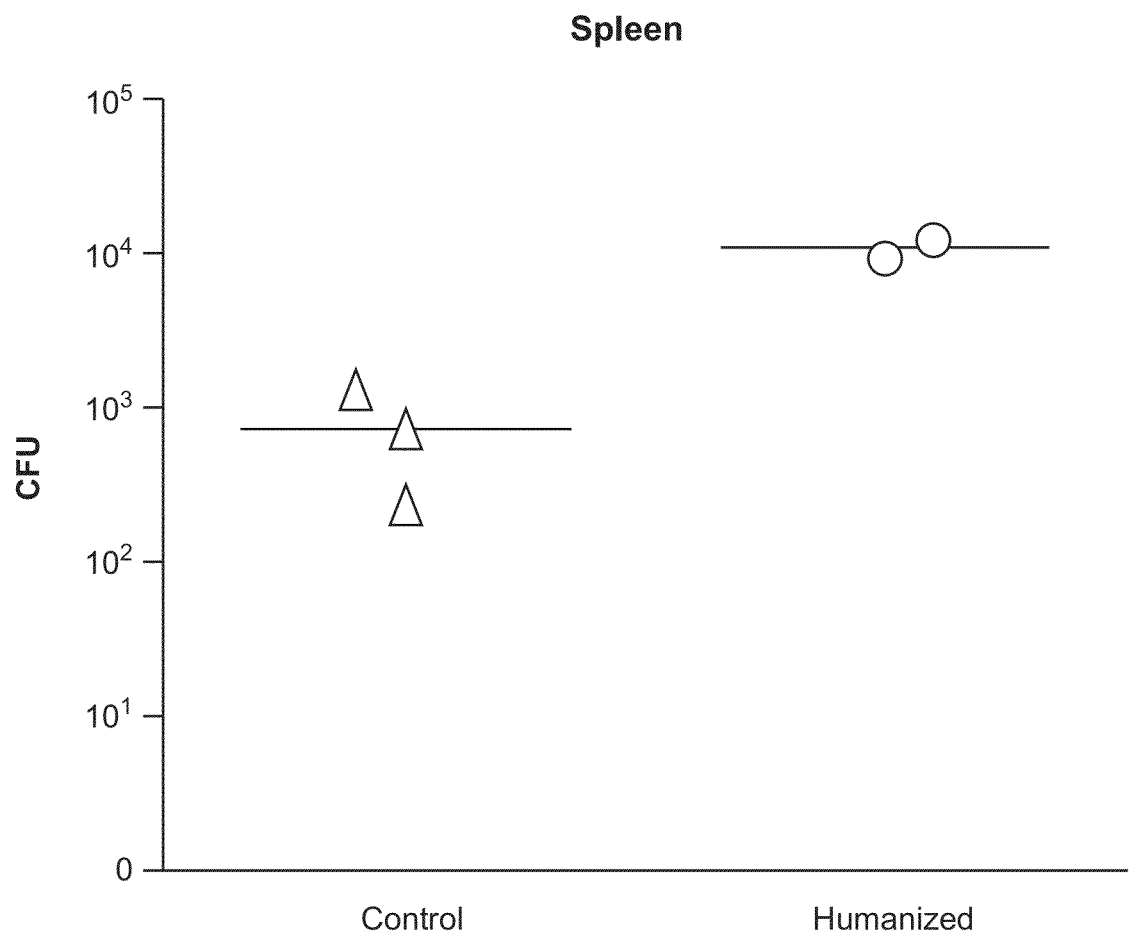
FIG. 2 shows *S. typhi* infection in spleens of engrafted RAG KO, Il2rg KO mice a week post-infection with $1 \times 10^3$ *S. typhi*.
Figure 3:
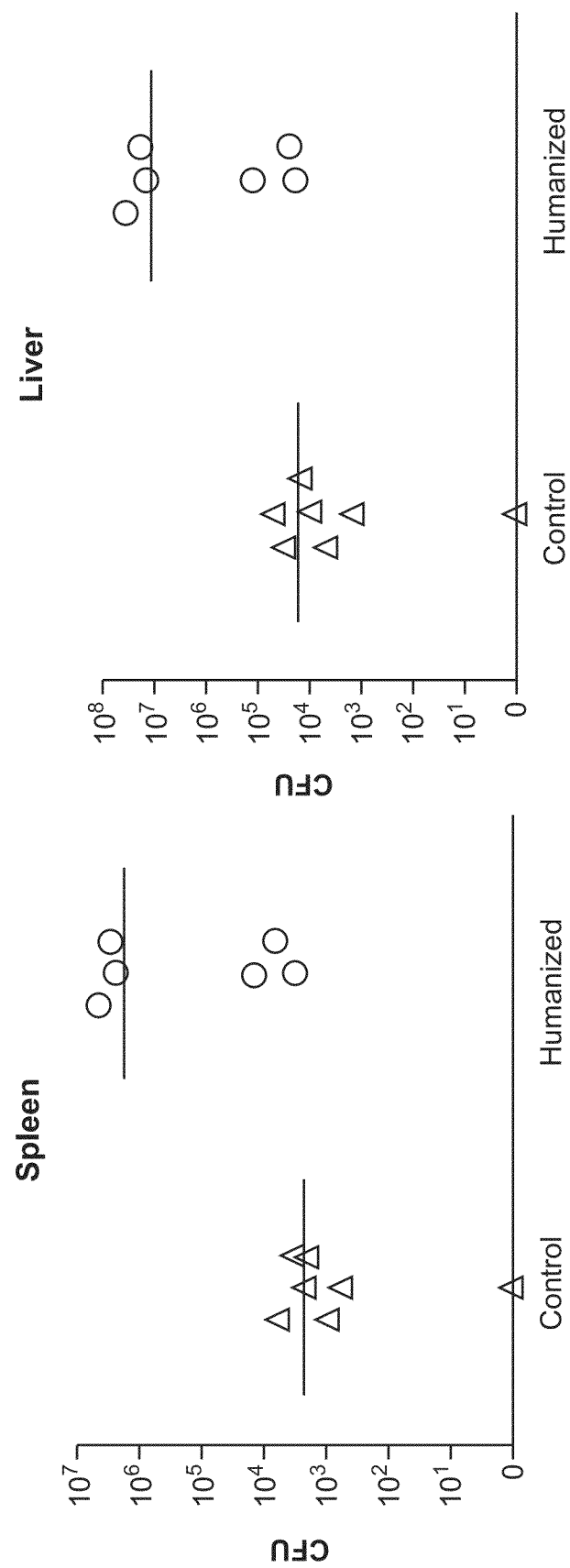
FIG. 3 shows *S. typhi* infection in spleens and livers of engrafted RAG KO, Il2rg KO mice 4 weeks post-infection with $1 \times 10^4$ *S. typhi*, wherein the mice were engrafted with CD34-positive fetal liver cells.
Figure 4:
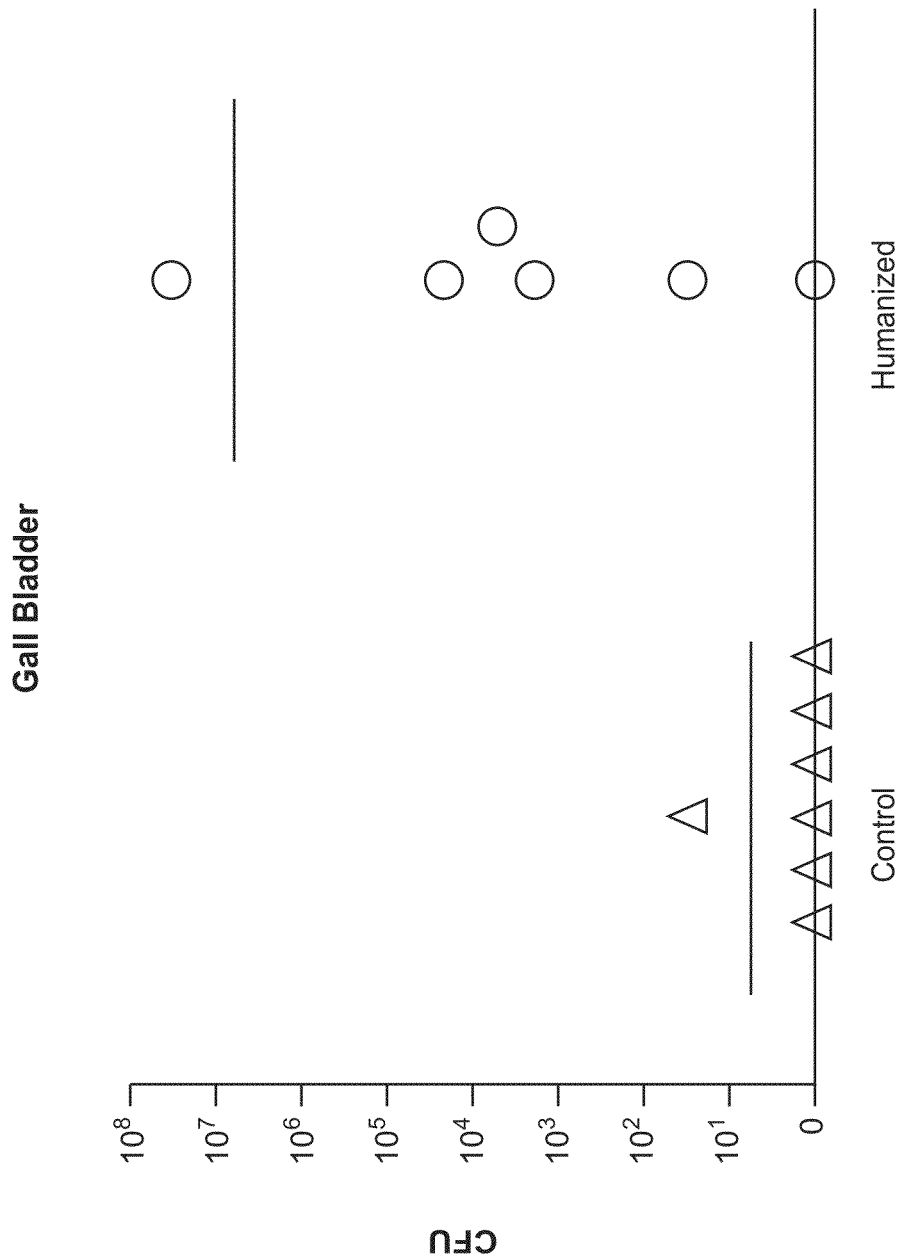
FIG. 4 shows *S. typhi* infection in gall bladders of RAG KO, Il2rg KO mice 4 weeks post-infection with $1 \times 10^4$ *S. typhi*, wherein the mice were engrafted with CD34-positive fetal liver cells.

FIGS. 2, 3 and 4 were obtained using only the first type of modified mice (comprising the modifications (a) a mouse RAG gene knockout; and (b) a mouse Il2rg gene knockout; and engraftment with human hematopoietic cells).

In various embodiments, the S. typhi-infected genetically modified mouse comprises a productive infection of S. typhi.

In one embodiment, the mouse is capable of harboring and reproducing S. typhi in one or more of its cells. In one embodiment, the mouse is capable of maintaining a S. typhi titer or level in its blood or in at least one tissue for at least a week, 10 days, two week, three weeks, or four weeks following an infective exposure to S. typhi.

In one embodiment, the method comprises administering an agent to a genetically modified mouse in accordance with the invention, wherein the genetically modified mouse is infected with S. typhi; detecting a level of S. typhi in blood or a tissue of a mouse following administration of the agent, and, optionally, determining if administration of the agent decreases the level of S. typhi in the blood or tissue of the mouse. In one embodiment, the agent is a vaccine. In another embodiment, the agent is an antibiotic or an agent that is suspected to have antibiotic properties. In one embodiment, the agent is antigen-binding protein, in a specific embodiment an antibody. In one embodiment, the agent is an approved pharmaceutical for use in a human.

In one embodiment, the method comprises infecting a genetically modified and engrafted mouse in accordance with the invention with a known amount of S. typhi, administering an agent to the infected mouse, and determining the amount of S. typhi in the genetically modified and engrafted mouse following administration of the agent. In one embodiment, the agent is determined to be an anti-S. typhi agent if it reduces the amount of S. typhi in blood or a tissue of the mouse by at least half following a single administration or two or more administrations of the agent over a selected period of time.

In one aspect, a method is provided for determining if a S. typhi isolate or strain of interest is drug resistant or multi-drug resistant, comprising administering a drug or a combination of drugs employed to treat S. typhi to a genetically modified and engrafted mouse according to the invention, wherein the mouse is infected with the S. typhi isolate or strain of interest. The method includes determining the effect, if any, of the drug or combination of drugs on (a) the titer of the S. typhi isolate or strain of interest in the blood or tissue of the mouse at a point in time after administration of the drug or combination of drugs, (b) the ability of the S. typhi isolate or strain of interest to maintain an infection in the mouse or a level of S. typhi in a tissue of the mouse after one or more administration(s) of the drug or combination of drugs, or (c) the ability of the S. typhi isolate or strain of interest to reproduce in the mouse at a point in time after administration of the drug or combination of drugs. In a specific embodiment, the drug is selected from the group consisting of amoxicillin, ampicillin, cefotaxime, ceftriaxone, ceftazidime, chloramphenicol, ciprofloxacin, co-trimoxazole, ertapenem, imipenem, fluoroquinolones (e.g., ciprofloxacin, gatifloxacin, ofloxacin), streptomycin, sulfadiazine, sulfamethoxazole, tetracycline, and a combination thereof. In a specific embodiment, the administration of the drug or combination of drugs is at least a week, 10 days, two week, three weeks, or four weeks after an infection-producing exposure to S. typhi.

In various aspects and embodiments, level of S. typhi in blood or tissue is measured by ascertaining the number of colony forming units per unit (e.g., weight or volume) of blood or tissue.

In one embodiment, a genetically modified and human hematopoietic cell-engrafted mouse in accordance with the invention has a S. typhi level, as measured by colony forming units (cfu's), of at least 100-, 1,000-, or 10.000-fold over a mouse that is not engrafted with human hematopietic cells.

Methods and compositions useful for ascertaining the efficacy of an anti-S. typhi vaccine. In one aspect, a method for ascertaining the efficacy of an anti-S. typhi vaccine is provided, comprising exposing a genetically modified and engrafted mouse in accordance with the invention to an anti-S. typhi vaccine, and thereafter exposing the genetically modified and engrafted mouse to S. typhi, and determining whether or to what extent the genetically modified and engrafted mouse is infectable by S. typhi.

In one embodiment, the anti-S. typhi vaccine comprises a S. typhi cell surface protein or immunogenic fragment thereof. In one embodiment, the vaccine comprises a membrane fraction of a S. typhi strain. In one embodiment, the vaccine comprises a recombinant S. typhi protein or immunogenic fragment thereof. In one embodiment, the vaccine comprises an expression vector that encodes a S. typhi protein or immunogenic fragment thereof. In one embodiment, the vaccine comprises an inactivated S. typhi strain or inactivated mixture of S. typhi strains.

Genetically modified and engrafted mice described in this disclosure are also useful for modeling human pathogen infections more closely than existing mice. For example, infection by M. tuberculosis. Genetically modified and engrafted mice described herein are useful for modeling a human infection of a mycobacterium, for example, by providing a M. tuberculosis mouse model that develops granulomas, including granulomas that comprise human immune cells and well-defined granulomas. The methods for drug and vaccine testing mentioned in connection with S. typhi infection of genetically modified and engrafted mice described are also applicable to M. tuberculosis applications, e.g., identifying drug-resistant strains, testing efficacy of an M. tuberculosis vaccine, testing anti-M. tuberculosis agents, measuring cfu's in response to an anti-M. tuberculosis agent, etc.

Genetically modified and engrafted mice described in this disclosure are also useful for modeling a human hematopoietic malignancy that originates from an early human hematopoietic cell, e.g. from a human hematopoietic or progenitor cell. Further applications of the genetically modified and engrafted mice described in this disclosure will be apparent to those skilled in the art upon reading this disclosure.

Thrombopoietin and Engraftment

Thrombopoietin (TPO) was initially identified as a growth factor that promotes the development of megakaryocytes and platelets (Wendling, F. et al. (1994) cMpl ligand is a humoral regulator of megakaryocytopoiesis, Nature 369:571-574; Kaushansky, K. et al. (1994) Promotion of megakaryocyte progenitor expansion and differentiation by the c-Mpl ligand thrombopoietin, Nature 369:568-571; Lok, S. et al. (1994) Cloning and expression of murine thrombopoietin cDNA and stimulation of platelet production in vivo, Nature 369:565-568; de Sauvage, F. J. et al. (1994) Stimulation of megakaryocytopoiesis and thrombopoiesis by the c-Mpl ligand, Nature 369:533-538; Bartley, T. D. et al. (1994) Identification and cloning of a megakaryocyte growth and development factor that is a ligand for the cytokine receptor Mpl, Cell 77:1117-1124; Kaushansky, K. (1998) Thrombopoietin, N Engl J Med 339:746-754; Kaushansky, K. (2005) The molecular mechanisms that control thrombopoiesis, J Clin Invest 115:3339-3347; Kaushansky, K. (2008) Historical review: megakaryopoiesis and thrombopoiesis, Blood 111:981-986).

TPO is constitutively produced by the liver and the kidneys and released into the blood circulation. The receptor for TPO, c-Mpl, is expressed by hematopoietic stem and progenitor cells in the bone marrow. C-Mpl is also expressed on circulating platelets. However, the binding of TPO on platelets does not activate any signaling pathway. Thus, thrombocytes act as a sink or scavengers for TPO and via this mechanism contribute to negative regulation of thrombopoiesis (Kuter, D. J. & Rosenberg, R. D. (1995) The reciprocal relationship of thrombopoietin (c-Mpl ligand) to changes in the platelet mass during busulfan-induced thrombocytopenia in the rabbit, *Blood* 85:2720-2730). Subsequently, TPO has been recognized for its important function to support the expansion and self-renewal of HSCs (Fox, N., et al. (2002) Thrombopoietin expands hematopoietic stem cells after transplantation, *J Clin Invest* 110, 389-3894; Kirito, K. et al. (2003) Thrombopoietin stimulates Hoxb4 expression: an explanation for the favorable effects of TPO on hematopoietic stem cells, *Blood* 102:3172-3178).

TPO deficiency leads to reduced numbers of HSCs in adult mice, and the presence of TPO is needed to maintain adult HSCs in quiescence (Yoshihara, H. et al. (2007) Thrombopoietin/MPL signaling regulates hematopoietic stem cell quiescence and interaction with the osteoblastic niche, *Cell Stem Cell* 1, 685-697; Qian, H. et al. (2007) Critical role of thrombopoietin in maintaining adult quiescent hematopoietic stem cells, *Cell Stem Cell* 1:671-684). Furthermore, TPO is required to support post-transplantation expansion of HSCs, necessary to replenish the hematopoietic compartment of irradiated hosts. Interestingly, it has been demonstrated that osteoblastic cells involved in forming the HSC "niche" in the bone marrow produce TPO, critical for HSC function and maintenance.

Although mouse and human TPO are both-sided cross-reactive to the respective cognate receptors when used at supraphysiological doses in vitro, affinity and biologic activity might differ when the cytokine acts at limiting, physiological doses in context of an in vivo environment. The inventors hypothesized that mouse TPO might not provide an appropriate stimulus to the human c-Mpl receptor in vivo, and therefore could account for the impaired properties of human HSCs in the mouse environment. To correct this potential defect, the inventors replaced the gene that encodes mouse TPO by its human counterpart in $Rag2^{-/-}\gamma_c^{-/-}$ mice. It was hypothesized that such a mouse would have an improved ability to sustain differentiation and function of a human hemat-lymphopoietic system.

Significant progress has been achieved in the development of mice that sustain differentiation and function of the human hemato-lymphopoietic system since the publication of the first models more than two decades ago. However, several limitations remain, including (i) the transient human cell engraftment, not lasting for the life of recipient mice, (ii) the unphysiologic bias towards lymphoid lineage and poor differentiation of myeloid cells, and (iii) the variability of engraftment levels between different animals, even when groups of mice are transplanted with cells from a single human donor. These limitations might be due to non-physiologic location of human cells, residual xenoreactivity of the immunodeficient host, different composition of hemato-lymphoid cells in mouse and human species, and/or due to lack or insufficient mouse to human cross-reactivity of hematopoiesis supporting factors, leading to preferential mouse cell support. Thus, providing physiologic levels of human growth factors and deleting respective mouse homologues in the host might further favor the development and survival of human cell populations. Here, we describe a novel strain of recipient mice in which we humanized the gene encoding thrombopoietin, a cytokine with important functions in the maintenance and self-renewal of hematopoietic stem cells.

Upon engraftment of these humanized thrombopoietin mice with human CD34+ hematopoietic stem and progenitor cells, a significant improvement was observed compared to previously available models on all three limitations listed above: bone marrow chimerism was higher and was maintained for at least six months; multilineage, in particular myeloid lineage differentiation was enhanced; and variability in engraftment levels was reduced.

A major difference between the mouse and human immune systems is the fraction of granulocytes present in the blood. Lymphocytes are preponderant in mice, while human blood is rich in granulocytes, a species difference unclear in its significance. Interestingly, the presence of human TPO improved differentiation of human granulocytes (FIG. 14). Thus, the presence of human TPO in recipient mice favors a balance between granulocytes and lymphocytes that reflects better the human physiological condition, a finding possibly due to better maintenance and/or differentiation of human myeloid progenitor cells.

More importantly, the results show that TPO humanization favors the maintenance of secondary recipient repopulating human hematopoietic stem and progenitor cells in the mouse environment (FIG. 15). Hence, the $Rag2^{-/-}\gamma c^{-/-}TPO^{h/h}$ mouse represents a novel model to study various aspects of human stem and progenitor cell function in vivo.

Nevertheless, although a better balance between the myeloid and lymphoid lineages in the blood was observed, no significant effect of TPO humanization on the overall engraftment levels in peripheral lymphoid tissues (including spleen, blood and thymus) was observed (FIG. 13($g$)-($i$)). This could be explained by different factors. First, although the recipient mice are sub-lethally irradiated before transplantation, a large population of mouse myeloid cells is still present. Among those cells, macrophages are able to phagocyte human cells and limit the overall engraftment levels in the periphery. Thus, the genetic depletion of mouse macrophages, or their functional inactivation, might permit higher levels of peripheral engraftment. Second, human cells may require additional human growth factors to favor their terminal differentiation, egress from the bone marrow and/or their survival in the periphery. A diverse panel of cytokines can be considered for each lineage. Finally, although secondary lymphoid organs are formed in humanized mice, their structure is not optimal compared to human tissues. This partially defective structure might represent a limit to the number of human cells that can survive in these organs.

Additional gene replacements can be used to further improve the mouse recipients. To achieve this, the technology used in this study, based on the knock-in replacement of a mouse gene by its human homolog, presents two main advantages compared to classical transgenic approaches. First, as it maintains most of the regulatory sequences of mouse origin, it ensures that the humanized gene is faithfully expressed in the mouse host. Second, as the knock-in strategy replaces the mouse cytokine by its human homolog, it can affect the population(s) of cells of mouse origin that depend on this cytokine, in the case that the human cytokine is not fully cross-reactive on the mouse receptor. This can provide a further competitive advantage to the human cell population(s) after transplantation. Indeed, this seems to be the case for human TPO, as the homozygous replacement of TPO leads to a reduction in mouse platelets and HSCs in non-engrafted animals (FIGS. 13($a$), 15($a$) and 15($b$)).

With human TPO knock-in mice, an improved model is provided that can be useful to study in vivo physiology of human hematopoiesis in general and human hematopoietic stem and progenitor cells in particular. Moreover, these mice sustain in vivo human hematopoietic malignancies that originate from early hematopoietic cells, such as, e.g., myeloid leukemias and myeloproliferative neoplasias.

EXAMPLES

The following examples are not intended to limit the scope of what the inventors regard as their invention. Unless indicated otherwise, parts are parts by weight, molecular weight is weight average molecular weight, temperature is in the Celsius scale, and pressure is at or near atmospheric.

Example 1

Making Human IL-3/GM-CSF and Human TPO Mice hIL-3/GM-CSF Targeting. A targeting construct for replacing a mouse IL-3 gene with a human IL-3 gene and a mouse GM-CSF gene with a human GM-CSF gene in a single targeting step was constructed using VELOCIGENE® technology (see, e.g., U.S. Pat. No. 6,586,251 and Valenzuela et al. (2003) "High-throughput engineering of the mouse genome coupled with high-resolution expression analysis," *Nat Blot* 21(6):652-659; hereby incorporated by reference) employing gap repair cloning.

Mouse sequences were obtained from bacterial artificial chromosome (BAC) RPCI-23, clone 5E15. The human sequences were obtained from Caltech D library (CTD), BAC clone 2333J5.

A gap repair donor vector containing a p15 origin of replication was constructed by cloning a 5' mouse homology arm immediately upstream of the mIL-3 ATG, a human 5' IL-3 homology arm extending from the hIL-3 ATG to about 274 nts into the hIL-3 gene, a poly linker, a 3' hGM-CSF beginning about 2.9 kb downstream of the polyA sequence of the hGM-CSF gene (about 233 bases), and a loxed drug selection cassette followed by a mouse 3' homology arm having sequence downstream (about 2.9 kb downstream) of the mGM-CSF polyA sequence. The gap repair vector was linearized and inserted into *E. coli* strain DH10B containing the human CTD BAC clone 2333J5 and a recombination enzyme vector as described in Valenzuela et al.

Cells were grown in drug selection medium. Individual clones were grown, gap repair donor vector DNA was extracted, and portions of the vector were sequenced for proper mouse-human junctions. Pulsed field gel electrophoresis was used to establish insert size and expected restriction fragment length.

Captured donor containing mouse upstream and downstream homology boxes flanking the hIL-3 gene, the hGM-CSF gene, and the loxed drug selection cassette was obtained from repair donor vector, the captured donor was linearized, and linearized captured donor was introduced into *E. coli* DH10B containing RPCI23 clone 5E15 and pABG vector. Cells were grown in drug selection medium. Individual clones containing captured donor DNA in RPCI23 clone 5E15 DNA (to form the targeting vector) were isolated, targeting vector DNA was extracted, and portions of the vector were sequenced for proper mouse-human junctions. Pulsed field gel electrophoresis was used to establish insert size and expected restriction fragment length.

Electroporation. The targeting vector was linearized and used to electroporate mouse ES cells as described in Valenzuela et al. Electroporated mouse ES cells containing the targeting vector were further electroporated with a transient Cre-expressing vector to remove the loxed drug selection cassette. The targeting vector was electroporated into Rag2 HET Il2rg y/– ES cells. The parental ES cell line in which the RAG2 gene and Il2rg gene knockout was made was a commercially available V17 ES cell (BALB/c×129 heterozygote). ES cells targeted with the hIL-3 and hGM-CSF genes were used to introduce into mouse embryos.

hIL-3/GM-CSF Mice. Targeted donor ES cells are introduced into an 8-cell stage mouse embryo by the VELOCI-MOUSE® method (see, e.g., U.S. Pat. No. 7,294,754 and Poueymirou et al. (2007) "F0 generation mice that are essentially fully derived from the donor gene-targeted ES cells allowing immediate phenotypic analyses," *Nat Blot* 25(1):91-99; hereby incorporated by reference). VELOCIMICE® (F0 mice fully derived from the donor ES cell) bearing the humanized IL-3 and GM-CSF, constructs are identified by genotyping for loss of mouse allele and gain of human allele using a modification of allele assay (see, e.g., Valenzuela et al.). These mice are first bred with BALB/cAnNCR and then mice heterozygous for Rag2 and Il2rg plus the human IL-3/GM-CSF KI are bred with Rag2/Il2rg double KO mice for engraftment studies.

Phenotyping hIL-3/GM-CSF Mice. Humanized mice were tested for production of human GM-CSF by RT-PCR using hGM-CSF-specific primers. The expression pattern of human GM-CSF for the tissues tested matched that of mouse GM-CSF (primarily expression in lung). ELISAs of splenocytes stimulated with ConA and IL-2 for 48 hours from the humanized mice were done to detect the presence of hIL-3 and hGM-CSF; splenocytes were positive for expression of both hIL-3 and hGM-CSF.

hTPO Targeting. A targeting construct (FIG. 11(*d*)) for replacing the mouse Tpo (mTpo) with the human TPO (hTPO) gene in a single targeting step was constructed using VELOCIGENE® technology employing gap repair cloning (Valenzuela et al.). The vector was designed to replace the sequence encompassing the open reading frame of Tpo, but to maintain the promoter and 5'UTR of mouse origin. Mouse sequences were obtained from bacterial artificial chromosome (BAC) RPCI-23, clone 98H7. Human sequences were obtained from BAC RPCI-11, clone 63m3. A gap repair donor vector containing a p15 origin of replication was constructed by cloning a 5' mouse homology arm immediately upstream of the mTpo ATG, a human 5' TPO homology arm extending from the hTPO ATG to about 275 nts into the hTPO gene, a poly linker, a 3' hTPO homology arm beginning about 1.5 kb downstream of the polyA sequence of the hTPO gene, and a loxed drug selection cassette followed by a mouse 3' homology arm having sequence downstream (about 3.5 kb downstream) of the mTpo polyA sequence. The gap repair vector was linearized and inserted into *E. coli* strain DH10B containing the human BAC clone RPCI-11, 63m3 and a recombination enzyme vector. Cells were grown in drug selection medium. Individual clones were grown, gap repair donor vector DNA was extracted, and portions of the vector were sequenced for proper mouse-human junctions. Pulsed field gel electrophoresis was used to establish insert size and expected restriction fragment length. Captured donor containing mouse upstream and downstream homology boxes flanking the hTPO gene and the loxed drug selection cassette was obtained from repair donor vector, the captured donor was linearized, and linearized captured donor was introduced into *E. coli* DH10B containing RPCI-23 clone 98H7 and pABG vector. Cells were grown in drug selection medium. Individual clones containing captured donor DNA in RPCI-23 clone 98H7 DNA (to form the targeting vector) were isolated, targeting vector DNA was extracted, and portions of the vector were sequenced for proper mouse-human junctions. Pulsed field gel electrophoresis was used to establish insert size and expected restriction fragment length. The targeting vector was linearized and used to electroporate mouse embryonic stem (ES) cells. The targeting vector was electroporated into RAG2+/–γcY/– ES cells. The parental RAG2$^{+/-}$γc$^{Y/-}$ ES cell line was made from a commercially available V17 ES cell line (BALB/c×129 heterozygote). Correctly targeted ES cells were further electroporated with a transient Cre-expressing vector to remove the loxed drug selection cassette. ES cells targeted with the hTPO gene and without selection cassette were introduced into an 8-cell stage mouse embryo by the VELOCIMOUSE® method (Poueymirou et al.). Rag2$^{-/-}\gamma_c^{-/-}$ mice with wild-type Tpo (TPO$^{m/m}$), heterozygous (TPO$^{h/m}$) or homozygous (TPO$^{h/h}$) TPO gene replacement were obtained.

Example 2 hIL-3/GM-CSF Mice: Engraftment

Isolation of Human Hematopoietic Stem Cells. Human umbilical cord blood and fetal liver samples were obtained under approval from the Yale University Human Investigation Committee from Yale-New Haven Hospital and Albert Einstein Medical College New York, respectively. CD34+ cells were isolated from human umbilical cord blood or fetal liver by density gradient centrifugation and immunomagnetic selection using CD34 microbeads (Miltenyi Biotec). Purity of isolated CD34-positive cells was verified by flow cytometry. Purified human CD34-positive cells were cryopreserved and stored in liquid nitrogen before use.

Engraftment of Mice with Human Hematopoietic Stem Cells. Engraftment was done as previously described (Traggiai et al. (2004) Development of a human adaptive immune system in cord blood cell-transplanted mice, *Science* 304: 104-107). Briefly, on the day of birth pups from RAG2 gene knockout/Il2rg gene knockout background (with or without hIL-3/hGM-CSF) were sublethally irradiated (2×200 cGy with a 4 hour interval). After irradiation newborn pups received 1-2×10$^5$ human CD34+ cells (resuspended in 25 microliters of PBS) by intrahepatic injection using a 30-gauge needle. Controls were injected with PBS only. Mice were weaned at 3-4 weeks of age and maintained under specific pathogen-free conditions. Mice received prophylactic antibiotics (Sulfatrim) in the drinking water to prevent opportunistic infections. All animal work was approved by Yale University Institutional Animal Care and Use Committee (IACUC) and conducted in accordance with IACUC regulations.

Analysis of Engrafted Mice. Engraftment with human hematopoietic cells was determined 8-12 weeks post-transplantation. Blood samples were obtained from the retro-orbital sinus and lysis of red blood cells was performed using ACK lysis buffer (Lonza). Samples were then stained with fluorescently labeled monoclonal antibodies against mouse CD45, human CD45, human CD3, and human CD14 (all from BD Biosciences) and analyzed by flow cytometry on a FACScalibur™ (BD Biosciences). Mice used for infection experiments had blood engraftment levels of >4% hCD45+ cells unless indicated otherwise. Matched mice, i.e., mice engrafted with the same batch of CD34+ cells, were used for experiments. Unless indicated otherwise, experiments were performed with mice engrafted with CD34+ cells from FL.

Flow Cytometry. For hIL-3/GM-CSF studies, cell suspensions were prepared from lung, BAL, bone marrow, thymus, spleen and blood of mice 10-14 weeks post-transplantation. Lysis of RBC was performed using ACK lysis buffer (Lonza). Samples were then stained with fluorochrome-labeled monoclonal antibodies (mAbs) against mouse and human cell surface antigens. The following mAbs were used: (1) Anti-human: CD3 (UCHT1), CD4 (RPA-T4), CD8 (HIT8a), CD11c (B-ly6), CD14 (MoP9), CD19 (HIB19), CD33 (WM53), CD45 (H130 and 2D1), CD56 (NCAM 16.2), CD66 (B1.1), CD116 (4H1), CD123 (9F5). (2) Anti-mouse: CD45 (30-F11), F4/80 (BM8). CD116, CD45 (30-F11), and F4/80 mAbs were from eBioscience. All other mAbs were from BD Biosciences. Samples were analyzed on a FACSCalibur™ or LSRII™ flow cytometer (BD Biosciences).

Methylcellulose CFU Assay. For hIL-3/GM-CSF studies, human CD34+ bone marrow cells from engrafted mice were purified by cell sorting. Sorted cells (1-1.5×10$^5$) were cultured in Iscove's modified Dulbecco's medium (IMDM, GIBCO) based methylcellulose medium (Methocult™ H4100, StemCell Technologies) that was supplemented with 20% FBS, 1% BSA, 2 mM L-glutamine, 55 µM 2-mercaptoethanol and the following human cytokines: stem cell factor (10 ng/ml), FLT3 ligand (10 ng/ml), thrombopoietin (50 ng/ml), IL-3 (20 ng/ml), IL-6 (10 ng/ml), IL-11 (10 ng/ml), GM-CSF (50 ng/ml), and erythropoietin (4 U/ml) (all R & D Systems). Cells were incubated in 60 mm Petri dishes at 37° C./5% $CO_2$. The number of colonies was determined by microscopy after 12-14 days.

Inflammatory Response to LPS. Mice received two i.p. injections of Ultrapure LPS *E. coli* 0111:B4 (Invivogen) 48 h apart (35 and 17.5 µg). Sera were harvested 2-3 h after each injection. Serum concentrations of human IL-6 were determined by ELISA (R&D Systems). Mice were sacrificed 72 h after the first LPS injection, blood collected by cardiac puncture and used for flow cytometry.

Intracellular Cytokine Staining. For hIL-3/GM-CSF studies, overlapping peptides covering the whole TB10.4 protein (Skjot et al. (2002) Epitope mapping of the immunodominant antigen TB10.4 and the two homologous proteins TB10.3 and TB12.9, which constitute a subfamily of the esat-6 gene family, *Infect. Immun.* 70:5446-5453) were synthesized by the W. M. Keck Facility of Yale University. Splenocytes from BCG-infected mice (2×10$^6$/well) were incubated with mixed peptides (each peptide at 5 µg/ml) in a total volume of 200 µl/well in 96-well U-bottom microtiter plates (Becton Dickinson) for 5 h at 37° C./5% $CO_2$. RPMI 1640 medium (Invitrogen) supplemented with 10% FCS, 1% penicillin-streptomycin, 1% L-glutamine, and 55 µM 2-mercaptoethanol was used for cell culture. Intracellular cytokine staining was performed using the Cytofix/Cytoperm™ kit (BD Biosciences) according to the manufacturer's instructions. The following mAbs were used for intracellular staining (all BD Biosciences): Anti-human IFNγ (B27), anti-mouse IFNγ (XMG1.2). Isotype-matched mAbs were used as controls.

Histology and Immunohistochemistry. For hIL-3/GM-CSF studies, organs were harvested and fixed in 10% neutral-buffered formalin or Zinc Fixative (BD Biosciences) for histological analysis. Paraffin-embedded tissues sections were prepared, stained with H&E or PAS, or processed for immunohistochemistry by the Yale Pathology Tissue Services. The following anti-human Abs were used for immunohistochemistry (all from Dako): CD45 (2B11+PD7/26), CD3 (F7.2.38), CD68 (PG-M1). Scoring of tissue sections for the presence of granulomas was performed in a blinded fashion.

Statistical Analysis. For hIL-3/GM-CSF studies, the non-parametric Mann-Whitney U test was used to determine statistical significance between two groups ($\alpha$=0.05). For multigroup comparisons, we applied one-way ANOVA with post hoc testing using Tukey's Multiple Comparison Test ($\alpha$=0.05). Only statistically significant P values (P<0.05) are shown.

Example 3 hIL-3/GM-CSF Engrafted Mice: Infection

*S. typhi* ISP2825 (Galán J.E. & Curtiss, R. (1991) Distribution of the invA, -B, -C, and -D genes of *S. thyphimurium* among other *S. serovars*: invA mutants of *S. typhi* are deficient for entry into mammalian cells, *Infect. Immun.* 59(9): 2901-2908, hereby incorporated by reference), a clinical isolate from a patient suffering from typhoid fever, was grown overnight in LB broth. On the following day, 40 microliters of the bacterial cell culture was transferred into 2 mL of fresh LB broth containing 0.3M NaCl and grown for ~3 hrs at 37° C. until the culture reached an $OD_{600}$ of ~0.9. The bacterial culture was spun down, resuspended in buffered saline solution, and used for infections. Nine to twelve week old humanized mice and control mice were inoculated on day 0 intraperitoneally with $1\times10^3$ or $1\times10^4$ or $1\times10^5$ of *S. typhi*. The infected mice were closely monitored and sacrificed at 4 weeks post infection. Spleen, liver, and gallbladder were aseptically removed and mechanically homogenized in 3-5 mL of sterile PBS containing 0.05% sodium deoxycholate. The tissue homogenate was serially diluted, plated on LB agar plates, and incubated overnight at 37° C. for colony counts. Colonies were counted and the number of total colony-forming units recovered was calculated. Mouse data are provided in FIGS. 1-4. In FIG. 1, "Control" mice are unengrafted genetically modified mice (RAG KO, Il2rg KO/hIL-3, hGM-CSF). In FIGS. 2-4, "Control" mice are unengrafted mice with a RAG KO and an Il2rg KO (i.e., they lack humanization of IL-3 and GM-CSF, but instead have endogenous mouse IL-3 and endogenous mouse GM-CSF). "Control" mice were injected with PBS instead of human CD34+cells.

As shown in FIG. 1, *S. typhi* infection in spleen is detected in the two genetically modified mice (RAG KO, Il2rg KO/hIL-3, hGM-CSF) at 10 days post-infection.

As shown in FIG. 2, at one week post-infection with $1\times10^3$ *S. typhi*, genetically modified mice (RAG KO, Il2rg KO) with percent engraftments of 3.8 and 3 showed infection in spleen ($p<0.01$), at about a thousand-fold higher than control mice. The p value for difference between Control and Humanized was $p<0.01$.

As shown in FIG. 3, genetically modified mice (RAG KO, Il2rg KO) engrafted with CD34-positive cells from fetal liver and infected with $1\times10^4$ *S. typhi* at four weeks post-infection showed *S. typhi* infection in both spleen (an average of about 1,000- to about 10,000-fold) and liver (an average of about 1,000-fold). Individual mice in the cohort tested for spleen *S. typhi* had (from top to bottom in the "Humanized" cohort in the left panel of FIG. 3) percent engraftment of human cells of 23.5, 40.1, 16.5, 50, 26, and 51.7. Individual mice in the cohort tested for liver *S. typhi* had (from top to bottom in the "Humanized" cohort in the right panel of FIG. 3) percent engraftment of human cells of 16.5, 40.1, 23.5, 26, 50, and 51.7. The p value for difference between Control and Humanized in spleen was $p<0.01$; in liver $p<0.03$.

As shown in FIG. 4, genetically modified mice (RAG KO, Il2rg KO) engrafted with CD34-positive cells from fetal liver and infected with $1\times10^4$ *S. typhi* at four weeks post-infection showed *S. typhi* infection in gall bladder, with a *S. typhi* cfu of, on average, a million-fold higher than the control mouse. Individual mice in the cohort tested for gall bladder *S. typhi* had (from top to bottom in the "Humanized" cohort in FIG. 3) percent engraftment of human cells of 23.5, 16.5, 40.1, 50, 26, and 51.7. The p value for difference between Control and Humanized was $p<0.03$.

The results establish that the genetically modified mice (RAG KO, Il2rg KO/hIL-3, hGM-CSF) can be colonized by *S. typhi* after systemic infection.

Example 4 hIL-3/GM-CSF Engrafted Mice: Validation of Mouse Model for Human Inflammatory Responses to Lung Pathogens The genes encoding GM-CSF (Csf2) and IL-3 are closely linked (<10 kb) on chromosomes 5 and 11 in humans and mice, respectively. This allowed replacement of the mouse with the human loci for both genes to generate hIL-3/GM-CSF KI mice (FIG. 5(*e*)). While the human Il3 KI allele is under the control of mouse regulatory elements, the human Csf2 KI allele remains under the control of its human regulatory elements. Expression of mouse and human GM-CSF mRNA was analyzed by RT-PCR in hIL-3/GM-CSF KI mice expressing one allele of each mouse and one allele of each human gene, referred to as IL-3/GM-CSF "human/mouse" (h/m) mice. Wild-type mice that only have the mouse alleles of IL-3 and GM-CSF are referred to as IL-3/GM-CSF "mouse/mouse" (m/m) mice.

RT-PCR and ELISA Analysis of hIL-3/GM-CSF KI Mice. Total RNA was extracted from homogenized tissues with TRIzol™ reagent (Invitrogen) according to the manufacturer's instructions. Equal amounts of DNase-treated RNA were used for cDNA synthesis with the SuperScript™ First-Strand Synthesis System (Invitrogen). Conventional RT-PCR was performed with the following primers: (1) Mouse Csf2: forward, CCAGTCCAAA AATGAGGAAG C (SEQ ID NO:7); reverse, CAGCGTTTTC AGAGGGCTAT (SEQ ID NO:8). (2) Human Csf2: forward, GGCGTCTCCT GAACCTGAGT (SEQ ID NO:9); reverse, GGGGATGACA AGCAGAAAGT (SEQ ID NO:10). (3) Mouse Rpl13: forward, GTACGCT-GTG AAGGCATCAA (SEQ ID NO:11); reverse, ATC-CCATCCA ACACCTTGAG (SEQ ID NO:12). Quantitative RT-PCR was performed on a 7500 Fast Real-Time PCR system with primer-probe sets purchased from ABI. Expression values were calculated using the comparative threshold cycle method and normalized to mouse or human HPRT. Mouse and human IL-3 and GM-CSF protein were detected with species-specific ELISA kits from R&D Systems according to the manufacturer's instructions. Splenocytes were activated with 5 µg/ml Concanavalin A (ConA) and 100 U/ml IL-2 and supernatants harvested for ELISA after 48 h of stimulation.

Expression in hIL-3/GM-CSF KI Mice. Human GM-CSF mRNA was expressed in a similar pattern to its mouse counterpart with highest expression in the lung (FIG. 5(*a*)). IL-3 is expressed mainly by activated T cells that also produce GM-CSF. Therefore, ELISA was performed on supernatants from activated splenocytes isolated from h/m mice; both human IL-3 and GM-CSF protein could be detected (FIG. 6(*f*)f, 6(*g*)). To confer a competitive advantage to human hematopoietic cells, generated homozygous KI mice were generated that express two alleles of human IL-3 and GM-CSF, referred to as IL-3/GM-CSF "human/human" (h/h) mice. Conventional and quantitative RT-PCR analysis of lung tissue showed that h/h mice express only human—but not mouse—GM-CSF mRNA (FIG. 5(*b*), 5(*c*)). Human GM-CSF protein could be detected by ELISA in the bronchoalveolar lavage (BAL) fluid of h/h mice (FIG. 5(*d*)). The results show that hIL-3/GM-CSF KI mice faithfully express human GM-CSF (and IL-3).

FIG. 5(*a*)-(*d*) shows validation of human GM-CSF expression in non-engrafted hIL-3/GM-CSF KI mice. FIG. 5(*a*) shows representative RT-PCR analysis of GM-CSF mRNA expression in various tissues from KI mice with one allele of human and one allele of mouse Csf2 (h/m). Li, liver; Br, brain; Lu, lung; Mu, muscle; Sp, spleen; Th, thymus; LN, lymph node; BM, bone marrow. Bottom, specificity of primers to detect human GM-CSF was verified by RT-PCR analysis of tissues from control mice (m/m). Ribosomal protein L13 (Rpl13) served as an endogenous control. FIG. 5(b) shows RT-PCR analysis of GM-CSF mRNA expression in lungs from m/m mice or homozygous KI mice expressing two alleles of human Csf2 (h/h) (each n=5). Rpl13 served as an endogenous control; NTC, no template control. FIG. 5(c) shows quantitative RT-PCR analysis of GM-CSF mRNA expression as in (b); GM-CSF expression was normalized to mouse Hprt (each n=5). FIG. 5(d) shows ELISA of human GM-CSF protein in BAL fluid recovered from m/m or h/h KI mice (each n=6); results are representative of two independent experiments; each dot represents one mouse; horizontal bars indicate mean values.

Figure 5E:
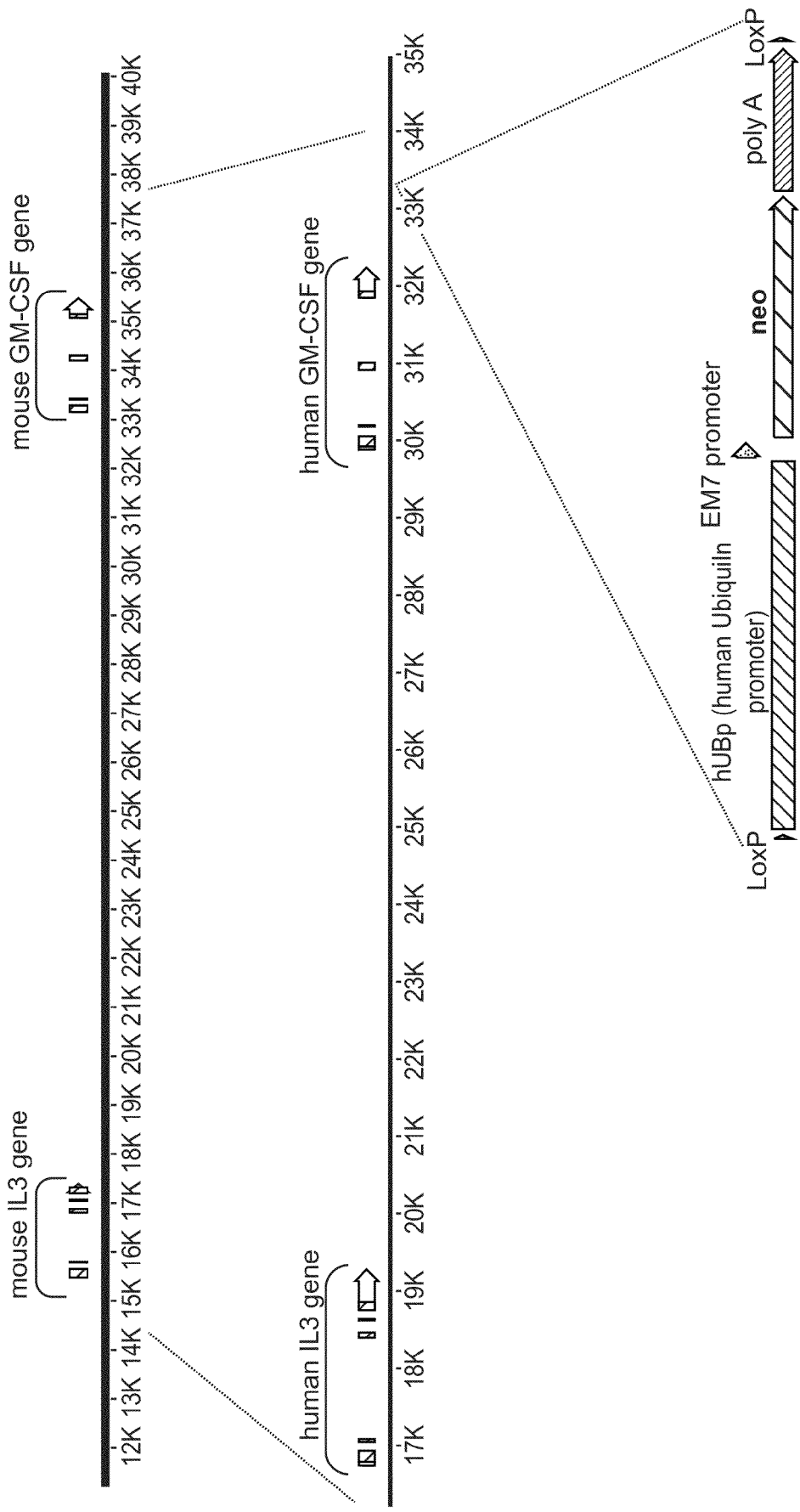
FIG. 5 (*a*)-(*d*) shows results of validation studies of hGM-CSF expression in hon-engrafted hIL-3/hGM-CSF mice.
Figure 6E:
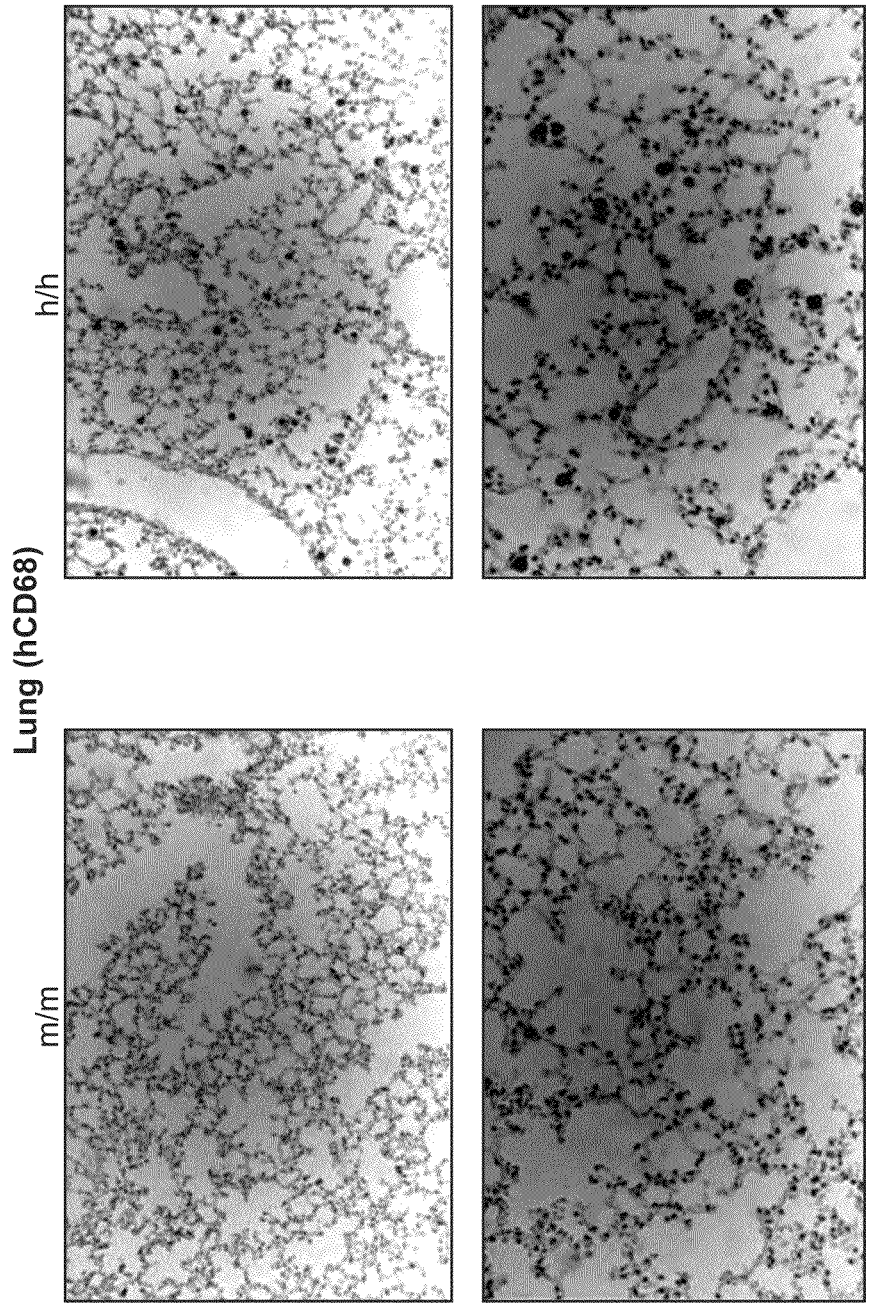
FIG. 6(*a*)-(*e*) shows results of lung studies of engrafted humanized (hIL-3/hGM-CSF) mice.

FIG. 5(e) shows a strategy to generate hIL-3/GM-CSF KI mice; genomic organization of mouse (top) and human (bottom) Il3 and Csf2 loci are shown on chromosomes 11 and 5, respectively. Mouse loci were replaced with human loci as described in this disclosure.

Figure 6F:
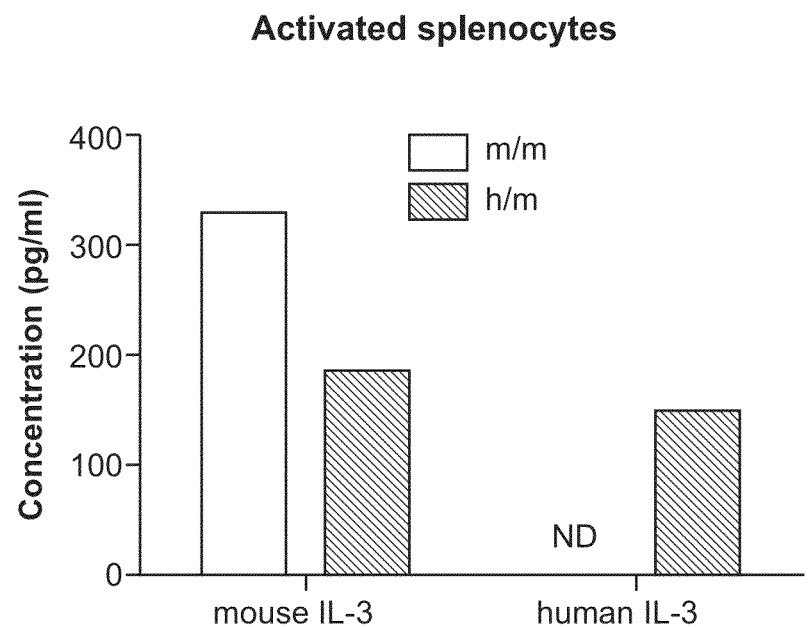
Figure 6G:
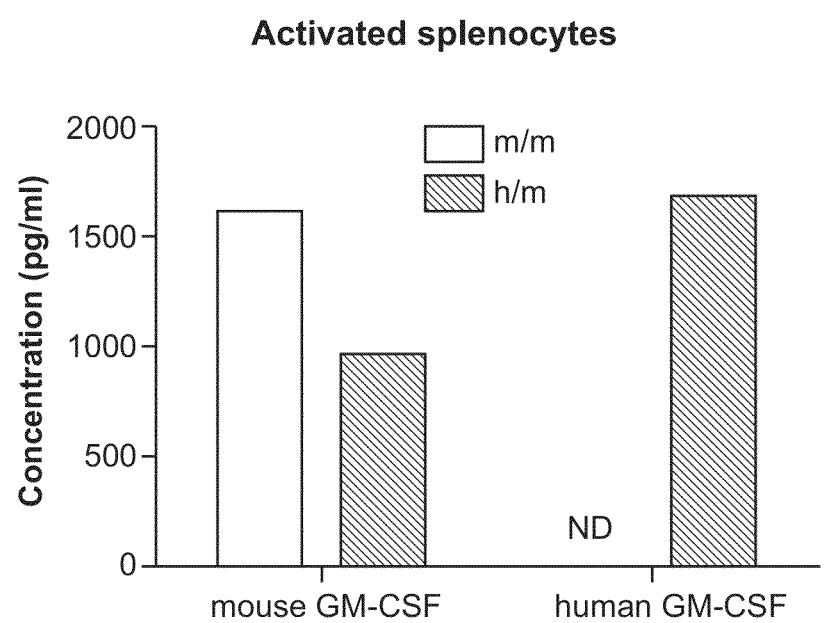

FIG. 6(f),(g) shows expression of human IL-3 and GM-CSF in non-engrafted hIL-3/GM-CSF KI mice. ELISA results for mouse and human IL-3 (f) and GM-CSF (g) production by activated splenocytes are presented. Splenocytes from either m/m (open bars) or h/m KI mice (filled bars) were stimulated with ConA and IL-2 for 48 h and supernatants harvested (each n=1). Human IL-3 and GM-CSF were not detectable (ND) in m/m mice.

Example 5 hIL-3/GM-CSF Engrafted Mice: Enhanced Human Inflammatory Responses hIL-3/GM-CSF KI mice were generated from embryonic stem (ES) cells with one allele of both Rag2 and Il2rg already deleted. Breeding onto the Rag2 KO Il2rg KO background then allowed engraftment with human CD34+ hematopoietic cells. Overall human CD45+ hematopoietic cell chimerism and distribution of T, B, and natural killer (NK) cells in bone marrow, thymus, spleen, and blood was not significantly increased in hIL-3/GM-CSF KI mice (data not shown). Also, the frequencies of total human CD33+ myeloid cells, CD66+ granulocytes, CD14+ monocytes/macrophages, CD14loCD16+ non-classical monocytes, CD11c+ dendritic cells (DC), and CD123+CD11c− plasmacytoid DC were not significantly increased in hIL-3/GM-CSF KI mice (data not shown). This applied to both h/m and h/h mice under steady-state conditions. Finally, human bone marrow cells from engrafted hIL-3/GM-CSF KI mice had a similar capacity to form myeloid colonies in methylcellulose in vitro (data not shown). These findings are consistent with results from KO mouse studies showing that both IL-3 and GM-CSF are largely dispensable for steady-state myelopoiesis in the organs analyzed here.

In contrast, GM-CSF plays an important role in mediating inflammatory responses. GM-CSF expression is induced by inflammatory stimuli, which leads to the production of inflammatory cytokines (such as IL-6 and TNFα) by monocytes/macrophages and to their recruitment to sites of inflammation. Human CD14+ monocytes from engrafted hIL-3/GM-CSF KI mice had the highest expression of the GM-CSF receptor α-chain (CD116) (FIG. 8(d)). Therefore, the analysis of engrafted hIL-3/GM-CSF KI mice focused on human monocytes/macrophages. First, the inflammatory response of human monocytes in engrafted hIL-3/GM-CSF KI mice was analyzed. Systemic inflammation was induced by intraperitoneal (i.p.) injection of lipopolysaccharide (LPS). The frequency of circulating human CD14+ monocytes was significantly increased in h/m compared to control m/m mice after LPS injection (FIG. 8(e),(f)). Enhanced mobilization of human monocytes in h/m mice was associated with increased serum concentrations of human IL-6 after one and two injections of LPS (FIG. 8(g)). LPS-induced production of human TNFα was also increased in h/m mice, but this result did not reach statistical significance. These data indicate that hIL-3/GM-CSF KI mice engrafted with human hematopoietic cells have enhanced human inflammatory responses mediated by human myelo-monocytic cells.

Figure 8A:
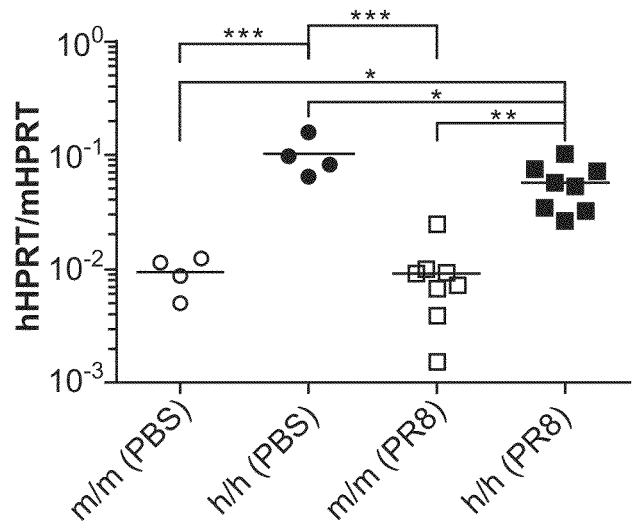
FIG. 8(*a*) shows expression of human Hprt normalized to mouse Hprt; (*b*) expression of human IFNγ normalized to mouse Hprt; (*c*) expression of human IFNγ normalized to human Hprt FIG. 8(*d*) shows flow cytometry analysis of human bone marrow cells from engrafted hIL-3/GM-CSF h/m KI mice in steady state; (*e*) flow cytometry analysis of human blood cells from CB-engrafted m/m or h/m KI mice 72 h after two i.p. injections of LPS; (*f*) frequency of human CD14+ blood cells in engrafted m/m or h/m KI mice 72 h post-LPS injections; (*g*) ELISA of human IL-6 in sera from engrafted m/m or h/m KI mice 2-3 h after first (top) and second (bottom) LPS injection.
Figure 8B:
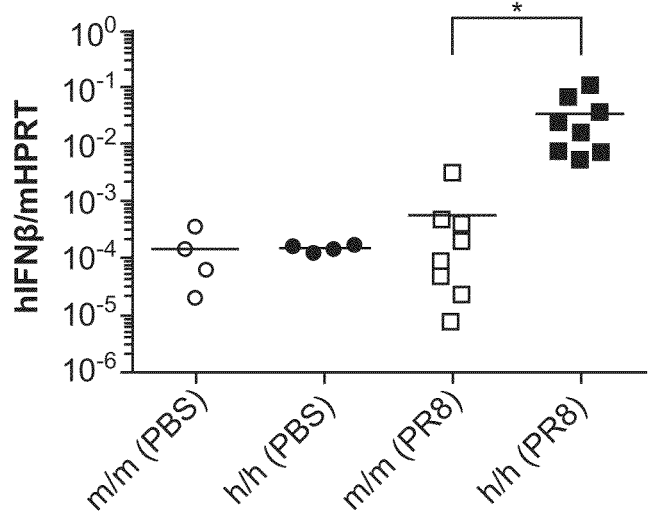
Figure 8C:
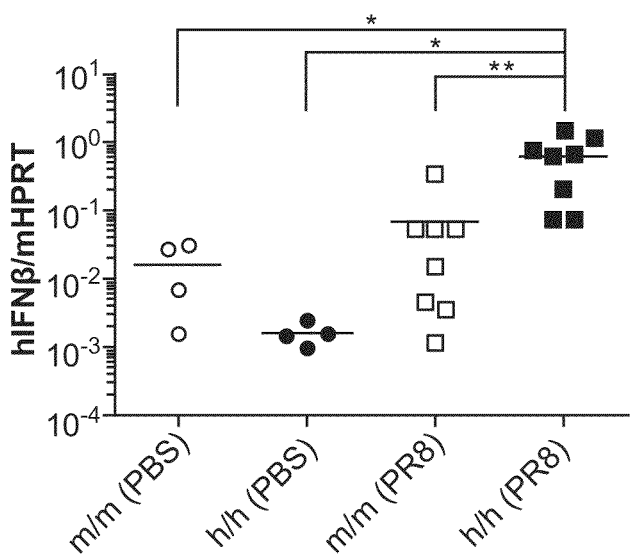
Figure 8D:
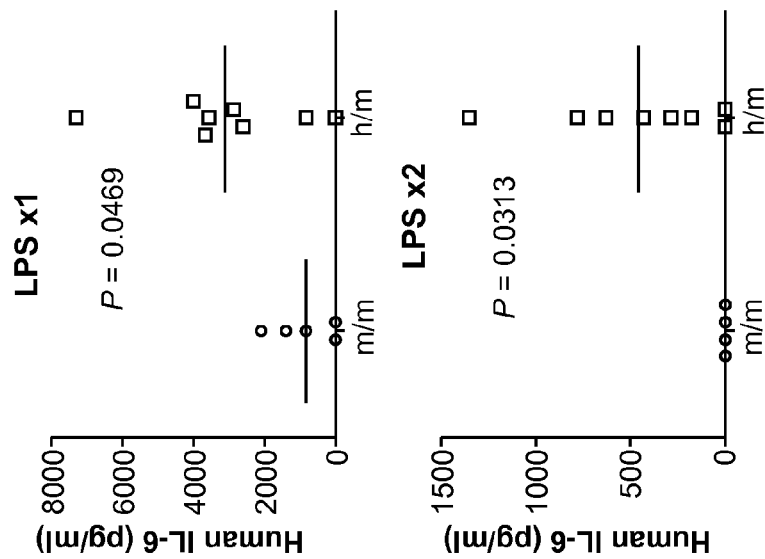
Figure 8E:
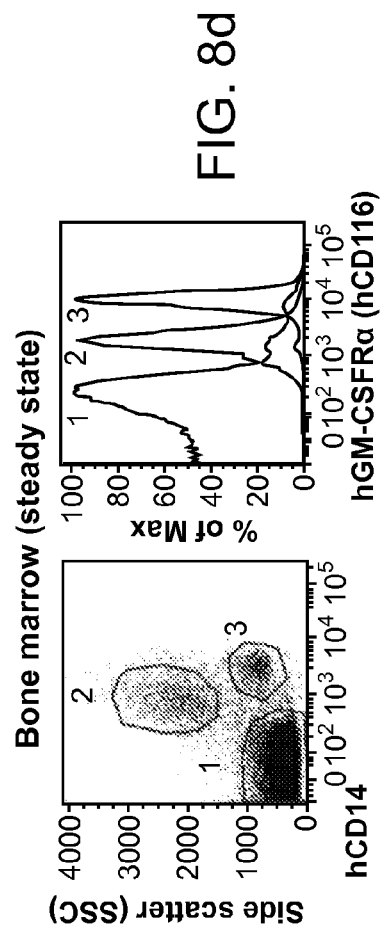
Figure 8F:
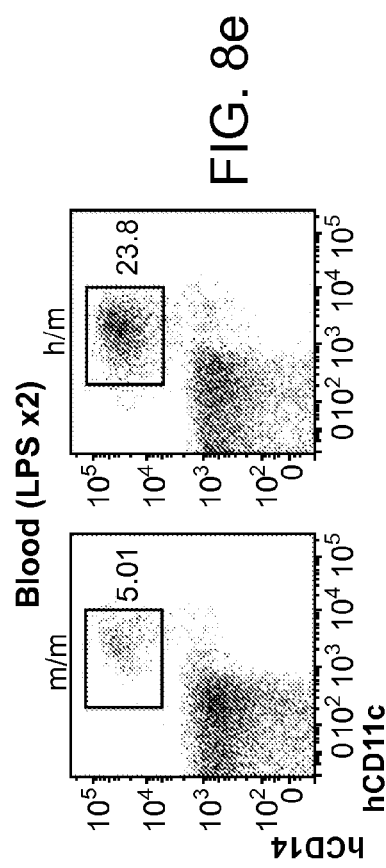
Figure 8G:
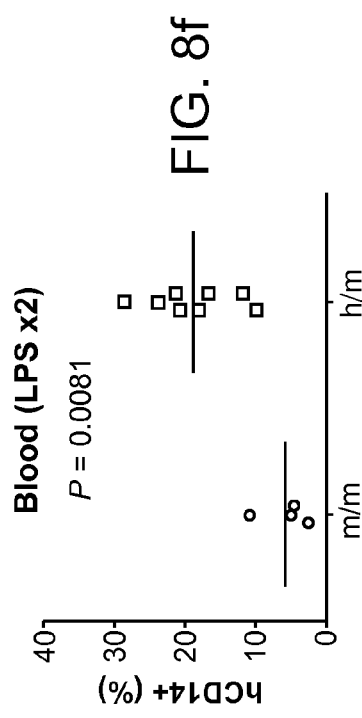

FIG. 8(d)-(g) illustrates enhanced human inflammatory responses in engrafted hIL-3/GM-CSF KI mice. FIG. 8(d) shows flow cytometry analysis of human bone marrow cells from engrafted hIL-3/GM-CSF h/m KI mice in steady state; the dot plot (left) is gated on hCD45+mCD45− cells. The histogram (right) shows GM-CSF receptor α (CD116) expression on CD14-cells (population 1), CD14mid/SSChi granulocytes (population 2), and CD14hi monocytes (population 3). One representative example from a total of 12 mice analyzed is shown. FIG. 8(e) contains a representative flow cytometry analysis of human blood cells from CB-engrafted m/m or h/m KI mice 72 h after two i.p. injections of LPS. Plots are gated on hCD45+mCD45-cells. Numbers next to boxed areas indicate the percentages of human CD14+ cells. FIG. 8(f) illustrates the frequency of human CD14+ blood cells in engrafted m/m (n=4) or h/m KI mice (n=8) 72 h post-LPS injections. FIG. 8(g) shows ELISA results for human IL-6 in sera from engrafted m/m (n=4-5) or h/m KI mice (n=8) 2-3 h after first (top) and second (bottom) LPS injection. One m/m mouse died after the first LPS injection. Each dot represents one mouse. Horizontal bars indicate mean values. Results are representative of two independent experiments.

Example 6 hIL-3/GM-CSF Engrafted Mice: Enhanced Human Macrophage Engraftment in Lung

BAL Analysis. Brochoalveolar analyses for hIL-3/GM-CSF studies were conducted in the following manner. Lungs were inflated with 1 ml PBS via a catheter inserted into the trachea. This was repeated twice and the recovered lavage pooled. After centrifugation, cell-free supernatants were saved for determination of GM-CSF protein concentration by ELISA or for total protein content with the BCA Protein Assay Kit (Pierce) according to the manufacturer's instructions. After red blood cell (RBC) lysis with ACK lysis buffer (Lonza), cell pellets were counted and either used for flow cytometry or for cytospin preparations. Cells were spun onto slides and stained with Diff-Quik™ Stain Set (Dade Behring) according to the manufacturer's instructions.

Enhanced Macrophage Engraftment. The absence of mouse GM-CSF leads to impairment of mouse alveolar macrophages (AM), which should favor reconstitution with human macrophages in homozygous hIL-3/GM-CSF KI mice. In support of this, human GM-CSF is highly expressed in the lung and BAL of h/h mice, while mouse GM-CSF is lacking.

Figure 9A:
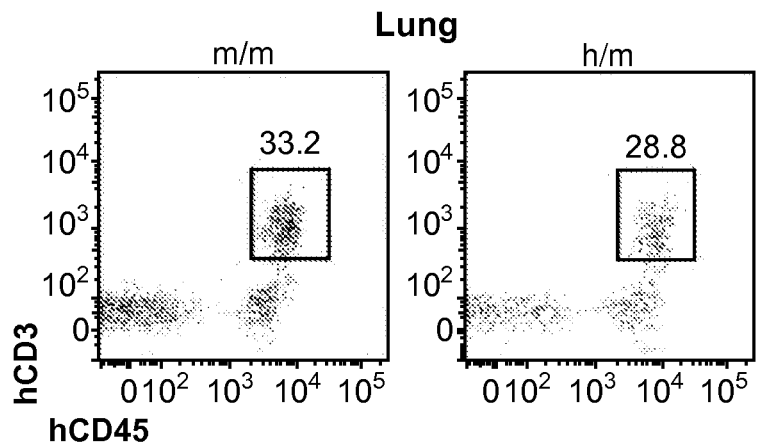
FIG. 9(*a*) shows frequency of human T cells (hCD45+ hCD3+) in the lung; (*b*) distribution of human CD4 and CD8 T cells in the lung; (*c*) ratio of human CD4 to CD8 T cells in lung; (*d*) flow cytometry analysis of splenocytes from BALB/c mice, engrafted m/m mice, and engrafted h/m KI mice four weeks after BCG infection; (*e*) quantitative RT-PCR analysis of human IFNγ (left) and TNFα (right) gene expression in lung tissue from BALB/c mice, non-engrafted (non) m/m mice, engrafted m/m mice, and engrafted h/m KI mice four weeks after BCG infection.
Figure 9B:
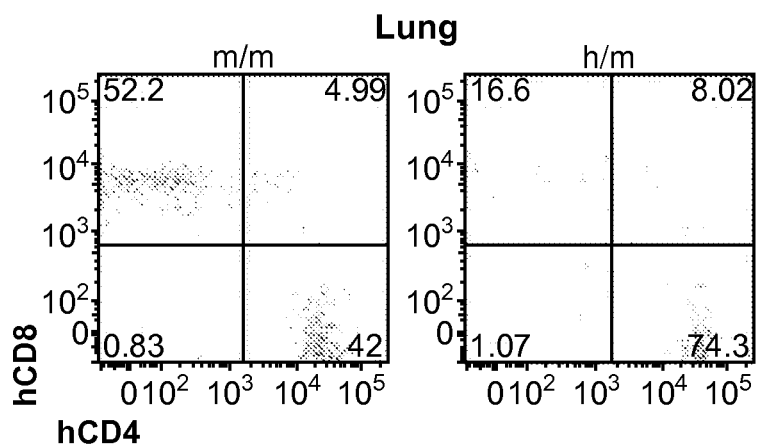
Figure 9C:
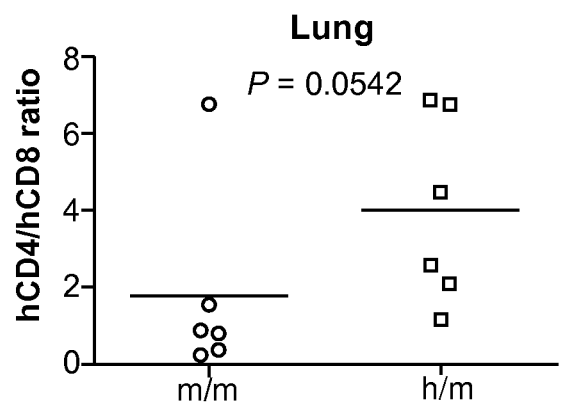
Figure 9D:
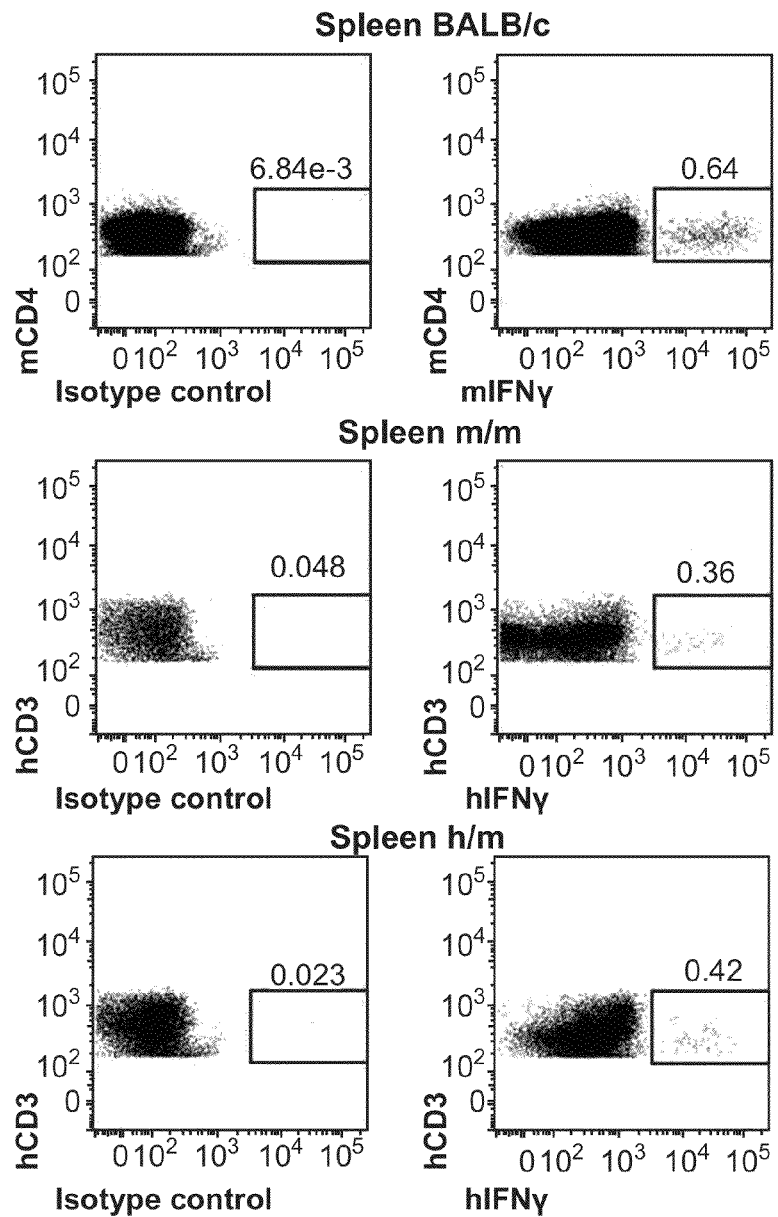
Figure 9E:
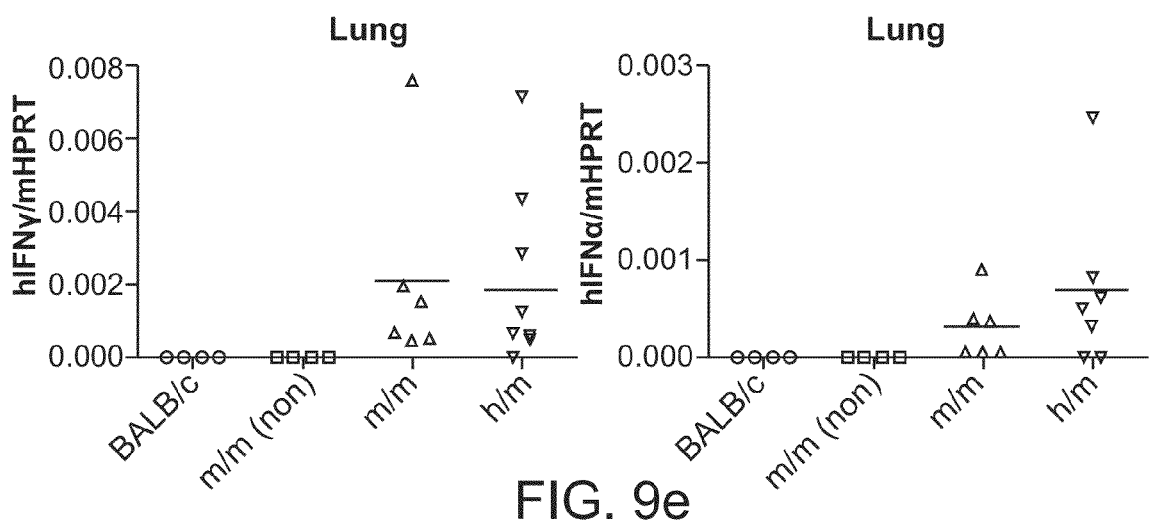
Figure 9F:
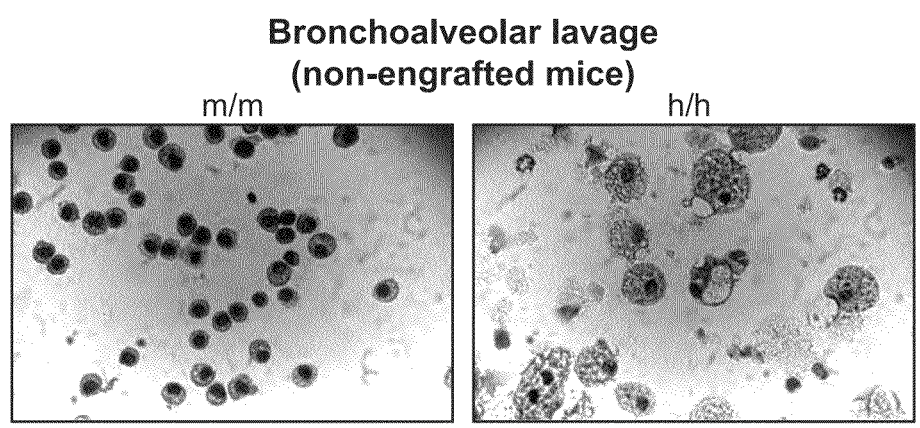

Mouse AM from non-engrafted h/h mice were enlarged and had the typical "foamy" appearance (FIG. 9(f)) which has been described for AM from GM-CSF KO mice. GM-CSF KO mice develop PAP due to a defect in surfactant clearance by AM that have a block in terminal differentiation. Similarly to what has been reported for GM-CSF KO mice, non-engrafted h/h mice developed features of PAP such as the subpleural accumulation of AM full of Periodic acid-Schiff (PAS)-positive material (FIG. 9(g)). It was therefore concluded that non-engrafted h/h mice show impaired differentiation of mouse AM and develop PAP, and are therefore functionally equivalent to GM-CSF KO mice.

Figure 9G:
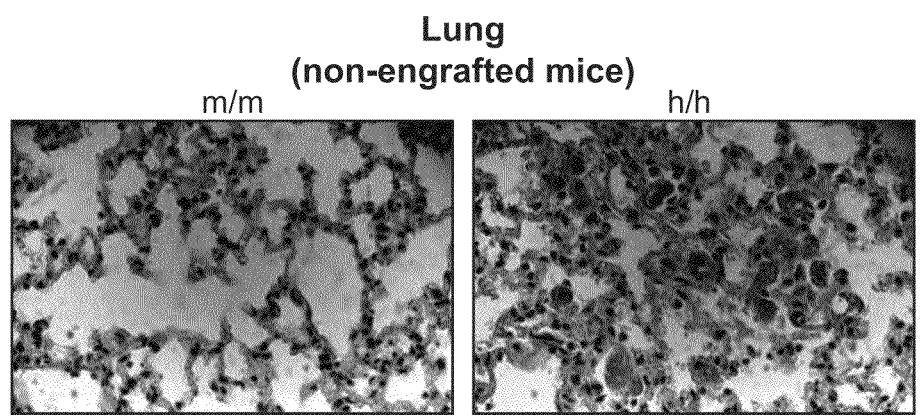

FIG. 9(f),(g) shows PAP development in non-engrafted homozygous hIL-3/GM-CSF KI mice. FIG. 9(f) shows Diff-Quick™ staining of BAL cells from non-engrafted m/m or h/h KI mice (magnification 400×); one representative example of a total of six mice analyzed per group is shown. FIG. 9(g) shows PAS staining of lung tissue sections from non-engrafted m/m or h/h KI mice (magnification 400×); one representative example of a total of 12 mice analyzed per group is shown.

Next, the lung compartment of h/h mice after engraftment with human hematopoietic cells was examined. FACS analysis showed that h/h mice had considerably more human CD45+ cells in the BAL (FIG. 6(a),(b)). Quantitative RT-PCR of lung tissue revealed that this increase in human cells consisted mainly of cells expressing mRNA for the human myeloid markers CD33, CD11b, CD11c, and CD14 (FIG. 6(c)). Furthermore, mRNA expression of human CD68, a mature macrophage marker that is mainly expressed intracellularly, was markedly increased in engrafted h/h mice (FIG. 6(d)). This increase in h/h mice was associated with higher expression of two transcription factors that are expressed by AM, namely PU.1 (Spit) and peroxisome proliferator-activated receptor-γ (PPARγ) (FIG. 6(d)). PU.1 is highly expressed in terminally differentiated AM in a GM-CSF-dependent manner. Importantly, transduction of GM-CSF KO AM with PU.1 in vitro reverses their functional impairment. PPARγ is also highly expressed in AM and, similarly to GM-CSF KO mice, PPARγ KO mice develop PAP. Immunohistochemical staining of lung sections revealed the presence of numerous hCD68+ cells with a typical intra-alveolar location, consistent with human AM, in engrafted h/h mice (FIG. 6(e)). In contrast, very few human AM could be detected in engrafted m/m control mice. In summary, lungs of CD34+ hematopoietic cell transplanted h/h mice show markedly improved engraftment of human macrophages.

FIG. 6(a)-(e) show that homozygous hIL-3/GM-CSF KI mice have better human macrophage engraftment in the lung. FIG. 6(a) shows representative flow cytometry analysis of BAL cells from engrafted m/m and h/h KI mice. Numbers next to outlined areas indicate the percentages of hCD45+ and mCD45+ hematopoietic cells. mCD45+hCD45+ cells have high autofluorescence and constitute F4/80+ mouse AM. FIG. 6(b) provides the numbers of human hematopoietic (hCD45+) cells in BAL from engrafted m/m and h/h KI mice (results are combined from three independent experiment (total n=15 per group)). FIG. 6(c) shows results of quantitative RT-PCR analysis of human lymphoid and myeloid gene expression in lung tissue from engrafted m/m and h/h KI mice (each n=4). Expression was normalized to mouse HPRT (*, P<0.05). FIG. 6(d) shows quantitative RT-PCR analysis of human macrophage gene expression in lung tissue from engrafted m/m and h/h KI mice (each n=4). Expression was normalized to mouse HPRT (*, P<0.05). Each dot represents one mouse. Horizontal bars indicate mean values. FIG. 6(e) shows immunohistochemistry of lung tissue sections stained for human CD68 from engrafted m/m and h/h KI mice (magnification 100× (top) and 200× (bottom)). One representative example of a total of 10 mice analyzed per group is shown.

Example 7 hIL-3/GM-CSF Engrafted Mice: PAP Alleviated by Human Hematopoietic Cells

It was investigated whether the increased engraftment of h/h mice with human macrophages leads to better human immune function in the lung. First, it was investigated whether human macrophages can rescue the PAP syndrome that is found in non-engrafted h/h mice. Although both type II alveolar epithelial cells and AM can respond to GM-CSF, PAP can be rescued by bone marrow transplantation. This indicates that hematopoietic cells, specifically AM, are the main cell type being able to reverse PAP. Therefore, it was hypothesized that h/h mice engrafted with human hematopoietic cells should have less severe PAP. As expected, non-engrafted h/h mice showed intra-alveolar accumulation of PAS-positive material (FIG. 7(a)), which is a hallmark of PAP. Consistent with the hypothesis, engrafted h/h mice had less severe protein accumulation in the lung, with the lungs of some h/h mice resembling (non-engrafted or engrafted) m/m control mice (FIG. 7(a)). In addition, engrafted h/h mice had significantly lower amounts of total protein in the BAL fluid than non-engrafted h/h mice (FIG. 7(b)). These results indicate that engrafted human hematopoietic cells (presumably AM) are capable of alleviating PAP in homozygous hIL-3/GM-CSF KI mice.

Figures 7A, 7B:
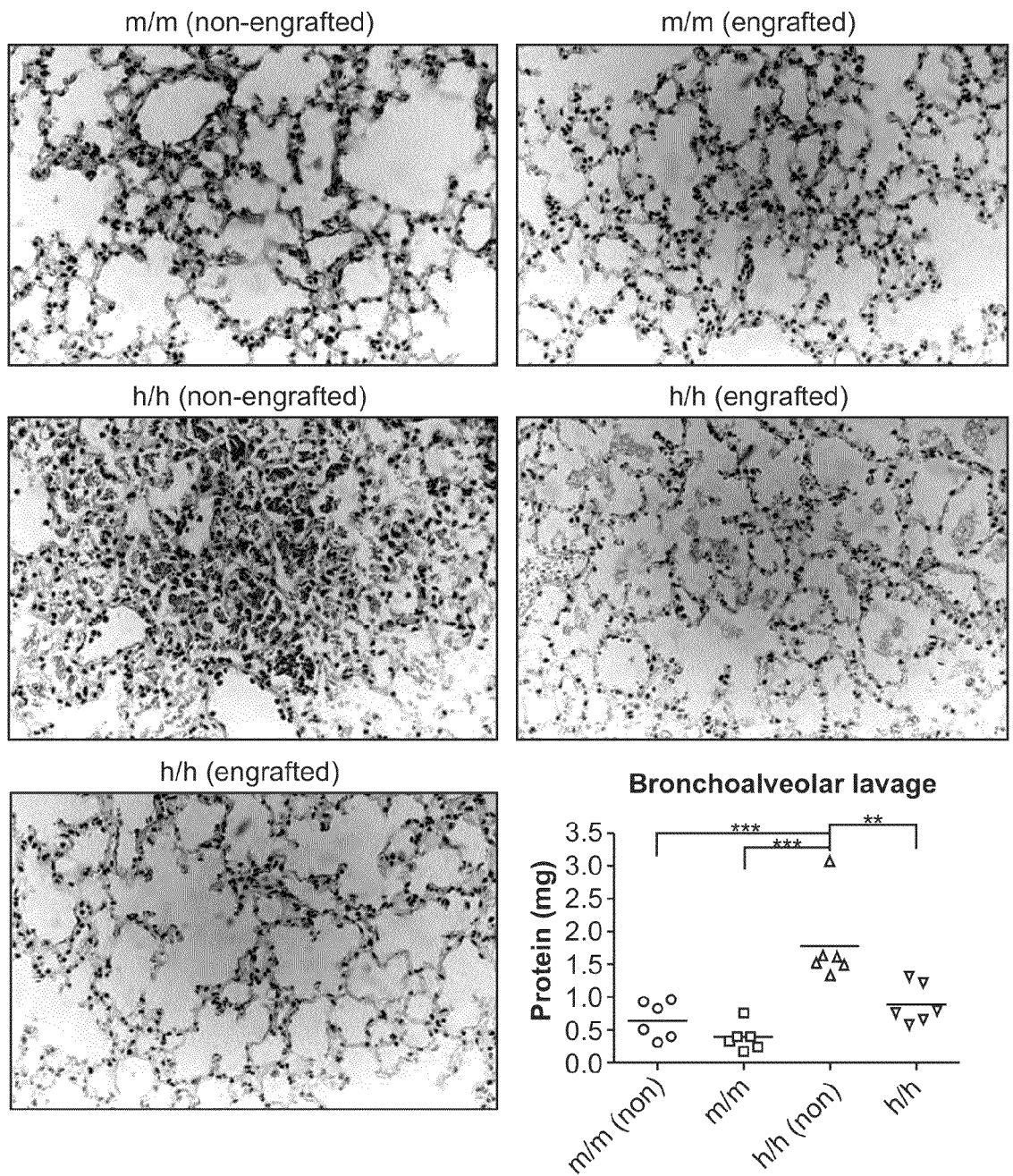
FIG. 7(*a*) shows PAS staining of lung tissue sections from non-engrafted or engrafted m/m or h/h KI mice; (*b*) quantification of total protein in BAL fluid from non-engrafted (non) or engrafted h/h KI mice or m/m control mice (n=6 per group).

FIG. 7(a)-(e) show that human hematopoietic cells alleviate PAP in homozygous hIL-3/GM-CSF KI mice. FIG. 7(a) shows PAS staining of lung tissue sections from non-engrafted or engrafted m/m or h/h KI mice. Lung sections from two different engrafted h/h KI mice are shown (magnification 400×). Representative examples of a total of 10-12 mice analyzed per group are shown. FIG. 7(b) shows quantification of total protein in BAL fluid from non-engrafted (non) or engrafted h/h KI mice or m/m control mice (n=6 per group). P<0.0001 (one-way ANOVA testing). Values of P as determined by Tukey's Multiple Comparison Test are indicated by asterisks (, P<0.01; *, P<0.001).

Example 8 hIL-3/GM-CSF Engrafted Mice: A stronger Human Type I IFN Response to Influenza A Influenza A infection. Mice (9-10 weeks old) were infected with $2 \times 10^4$ plaque-forming units of influenza A/PR8 (H1N1) virus via the intranasal route. Infection was performed by the intranasal application of 50 µl virus stock diluted in PBS (or an equal volume of PBS as a control) to mice that had been deeply anesthetized with Anafane™ (Ivesco). Lungs were harvested 24 h after infection for RNA extraction and quantitative RT-PCR analysis as described above.

In addition to their role in lung homeostasis, AM are essential for host defense in the lung. Numerous studies have shown that GM-CSF KO mice are more susceptible to a variety of pathogens in the lung. To assess the functional response of engrafted human AM to a lung pathogen, engrafted h/h mice were infected with influenza A/PR8 (H1N1) virus via the intranasal route. AM are the main producers of type I interferons (IFN) after infection with pulmonary viruses and AM are required for an effective innate response to influenza A. Expression of human hypoxanthine phosphoribosyltransferase (HPRT) mRNA was significantly higher in the lungs of engrafted h/h compared to control m/m mice (FIG. 8(a)), indicating better human immune cell chimerism. Engrafted m/m mice showed no significant induction of human IFNβ mRNA expression after influenza A infection when compared to engrafted m/m mice that had received PBS intranasally (FIG. 8(b)). In contrast, engrafted h/h mice expressed significantly more human IFNβ mRNA than both non-infected h/h mice and infected m/m mice (FIG. 8(b)). The increased expression of human IFNβ mRNA in h/h mice compared to m/m mice was still significant when normalized to human HPRT, i.e., to the number of human cells in the lung (FIG. 8(c)). Taken together, homozygous hIL-3/GM-CSF KI mice allow better human macrophage chimerism and function in the lung that leads to enhanced human mucosal immunity to viral infection.

FIG. 8(a)-(g) shows that homozygous hIL-3/GM-CSF KI mice mount a stronger human type I IFN response to influenza A infection. FIG. 8(a)-(c) show quantitative RT-PCR analysis of gene expression in lung tissue from m/m and h/h KI 24 h after intranasal infection with influenza A (PR8) (each n=8). Intranasal application of PBS was used as a control (PBS) (each n=4). FIG. 8(a) shows expression of human Hprt normalized to mouse Hprt. P<0.0001 (one-way ANOVA testing). FIG. 8(b) shows expression of human IFNγ normalized to mouse Hprt. P=0.0171 (one-way ANOVA testing). FIG. 8(c) shows expression of human IFNγ normalized to human Hprt. P=0.0032 (one-way ANOVA testing). Values of Pas determined by Tukey's Multiple Comparison Test are indicated by asterisks (*, P<0.05; , P<0.01; *, P<0.001). Each dot represents one mouse. Horizontal bars indicate mean values. Results are representative of two independent experiments.

Example 9 hIL-3/GM-CSF Engrafted Mice: Granulomas with Human Cells after Mycobacterial Infection The potential of hIL-3/GM-CSF KI mice to support human inflammatory responses to a second pathogen with tropism for the lung, where macrophages play a central role in the pathogen-specific immune response, was investigated. Granuloma formation after infection with mycobacteria was selected. The granuloma represents a specialized local inflammatory response that is the hallmark of infection with mycobacteria. It is a classic example of a DTH response and its formation is dependent on the interaction between activated T cells and macrophages. Both IL-3 and GM-CSF are required for optimal DTH responses and, importantly, GM-CSF KO mice do not form granulomas when infected with mycobacteria.

Engrafted hIL-3/GM-CSF h/m KI mice were infected by intravenous injection with *Bacillus* Calmette-Guérin (BCG), an attenuated strain of *M. bovis* that is used as a vaccine against tuberculosis in humans. Mice used for BCG infection experiments had blood engraftment levels of >20% hCD45+ cells with >8% of hCD45+ cells being T cells (hCD3+). Mice were 9-10 weeks old at the time of infection. Mice were infected with $1 \times 10^5$ colony-forming units of BCG (Statens Serum Institute Copenhagen) in a volume of 0.1 ml by tail vein injection.

Since T cells are essential for granuloma formation, first the human T cell response to BCG four weeks after infection was examined. Flow cytometry clearly demonstrated the presence of human T cells in the lungs of both engrafted m/m and h/m mice (FIG. 9(a)). In fact, T cells were the predominant human hematopoietic cell type in BCG-infected lungs. Compared to m/m control mice, h/m mice infected with BCG had a higher average ratio of human CD4 to CD8 T cells in the lungs although this difference did not quite reach statistical significance (FIG. 9(b), 9(c)). There was no difference in the splenic hCD4/hCD8 T cell ratio between the two groups of mice.

Next, the expression of two T cell-derived cytokines was analyzed, namely IFNγ and TNFα, both of which are crucial for the protective immune response against mycobacteria. BCG-specific IFNγ production by intracellular cytokine staining after restimulation of splenocytes from infected mice with peptides derived from the immunodominant mycobacterial antigen TB10.4 was examined. As expected, a population of IFNγ-producing mouse T cells could be detected among splenocytes from BALB/c mice (FIG. 9(d)). In addition, a human BCG-specific T cell response was found in a subset of engrafted h/m and m/m mice (FIG. 9(d)). Finally, the majority of engrafted h/m and m/m mice expressed human IFNγ and TNFα mRNA in the lung after BCG infection (FIG. 9(e)). These results show that a subset of engrafted mice are capable of mounting a pathogen-specific human T cell response to BCG, although this response was not enhanced in hIL-3/GM-CSF KI mice. Consistent with this, the bacterial burden was not different between h/m and m/m mice.

Next, granuloma formation was assessed in lung and liver by histology four weeks post-infection. Non-engrafted m/m mice (lacking T cells) did not develop granulomas (Table 1), which is consistent with the requirement for T cells for granuloma formation. Similarly, m/m mice engrafted with human cells did not show any granulomas in either lung or liver (Table 1). In contrast, the majority of h/m mice had small lesions or granulomas in either lung (FIG. 10(a)) or liver or in both organs (Table 1). In general, the observed granulomas were small and had the loose organization more typical of granulomas in mice than in humans. However, lung granulomas in hIL-3/GM-CSF KI mice contained human hematopoietic cells (hCD45+) as demonstrated by immunohistochemistry (FIG. 10(b)). The majority of these cells were human T cells (hCD3+) with a few centrally located human macrophages (hCD68+) (FIG. 10(b). In summary, engrafted hIL-3/GM-CSF KI mice are capable of developing granulomas that contain human T cells and human macrophages in response to mycobacterial infection, which has not been previously reported in HIS mice. Table 1 lists lesions/granulomas found in liver and lung tissue sections from BALB/c, non-engrafted m/m (non), engrafted m/m, and engrafted hIL-3/GM-CSF h/m KI mice four weeks after BCG infection.

TABLE 1

Granulomas in BCG-Infected Engrafted hIL-3/GM-CSF KI

| Mouse # | IL-3/GM-CSF | Liver | Lung |
|---|---|---|---|
| 1 | m/m (non) | No lesions | No lesions |
| 2 | m/m (non) | No lesions | No lesions |
| 3 | m/m (non) | No lesions | No lesions |
| 4 | m/m (non) | Small lesions | No lesions |
| 1 | m/m | No lesions | No lesions |
| 2 | m/m | No lesions | No lesions |
| 3 | m/m | No lesions | No lesions |
| 4 | m/m | No lesions | No lesions |
| 5 | m/m | No lesions | No lesions |
| 6 | m/m | No lesions | No lesions |
| 1 | h/m | No lesions | No lesions |
| 2 | h/m | Neutrophilic lesion | Granulomas |
| 3 | h/m | Small lesions | No lesions |
| 4 | h/m | Small lesions | No lesions |
| 5 | h/m | Small lesions | No lesions |
| 6 | h/m | No lesions | Granulomas |
| 7 | h/m | Granulomas | No lesions |
| 1 | BALB/c | No lesions | No lesions |
| 2 | BALB/c | Small lesions | No lesions |
| 3 | BALB/c | Small lesions | No lesions |
| 4 | BALB/c | Granulomas | No lesions |

FIG. 9(a)-(g) shows human T cell response to BCG in engrafted hIL-3/GM-CSF KI mice. FIG. 9(a)-(c) shows flow cytometry analysis of lung cells from engrafted m/m and h/m KI mice four weeks after BCG infection. FIG. 9(a) shows frequency of human T cells (hCD45+hCD3+) in the lung.

Numbers next to boxed areas indicate percentages of cells. FIG. 9(b) shows the distribution of human CD4 and CD8 T cells in the lung. Dots plots are gated on hCD45+hCD3+ cells. Numbers in quadrants indicate percentages of cells. FIG. 9(c) shows the ratio of human CD4 to CD8 T cells in lung (each n=6). Each dot represents one mouse. Horizontal bars indicate mean values. FIG. 9(d) shows flow cytometry analysis of splenocytes from BALB/c mice, engrafted m/m mice, and engrafted h/m KI mice four weeks after BCG infection. Splenocytes were restimulated in vitro with a pool of overlapping peptides covering the TB10.4 protein as described herein. Dot plots show the frequencies of mouse IFNγ+ CD4 T cells (mCD4+) or human IFNγ+ T cells (hCD3+) as determined by intracellular cytokine staining. Staining with isotype-matched abs was used as a control. FIG. 9(e) shows the results of quantitative RT-PCR analysis of human IFNγ (left) and TNFα (right) gene expression in lung tissue from BALB/c mice, non-engrafted (non) m/m mice, engrafted m/m mice, and engrafted h/m KI mice four weeks after BCG infection (n=4-7 per group). Each dot represents one mouse. Horizontal bars indicate mean values.

Figure 10A:
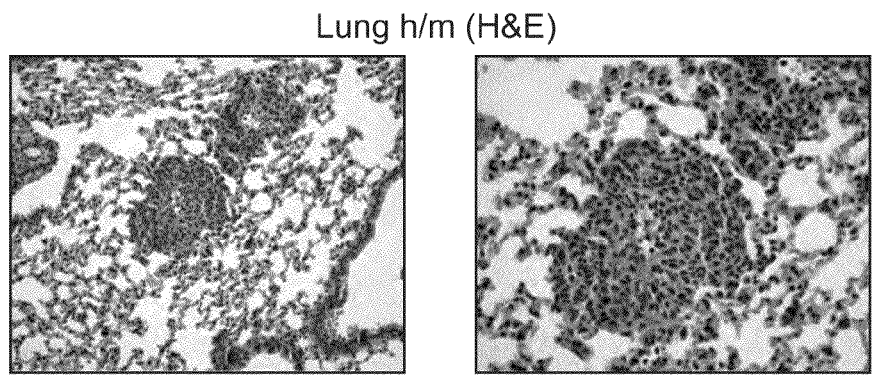
FIG. 10(*a*) shows hematoxylin and eosin (H&E) staining of lung tissue sections from engrafted h/m KI mice four weeks after BCG infection; magnification 100× (left) and 200× (right); (*b*) lung tissue sections stained for human CD45, CD3, or CD68 from engrafted h/m KI mice four weeks after BCG infection; magnification 200×.
Figure 10B:
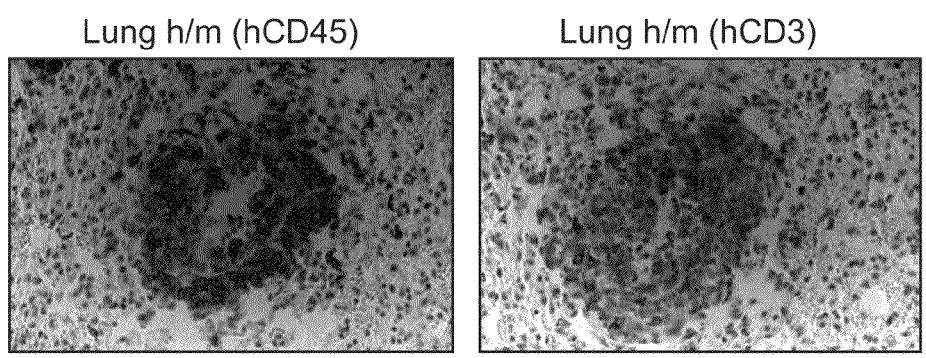
Figure 10B:
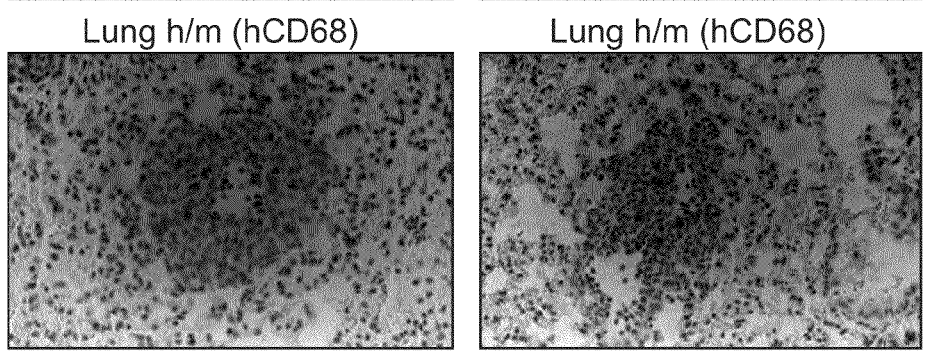

FIG. 10(a),(b) show that engrafted hIL-3/GM-CSF KI mice develop granulomas containing human cells after BCG infection. FIG. 10(a) shows hematoxylin and eosin (H&E) staining of lung tissue sections from engrafted h/m KI mice four weeks after BCG infection (magnification 100× (left) and 200× (right)). FIG. 10(b) shows immunohistochemistry of lung tissue sections stained for human CD45, CD3, or CD68 from engrafted h/m KI mice four weeks after BCG infection (magnification 200×). One representative example of two mice with lung granulomas is shown.

Example 10 hTPO Mice: Engraftment and Analysis

Transplantation into TPO Mice. Recipient mice were engrafted with human hematopoietic progenitors as described in Traggiai et al. Cord blood samples were collected from healthy full-term newborns, under approval from the Yale human investigations committee (Department of Labor and Birth, Yale New Haven Hospital, New Haven, Conn.). Fetal liver samples were obtained from the Human Fetal Tissue Repository at Albert Einstein College of Medicine, Bronx, N.Y.; and from Advance Biosciences Resources, Inc., Alameda, Calif.

Fetal liver samples were cut in small fragments, treated for 45 minutes at 37° C. with Collagenase D (100 ng/ml, Roche) and a cell suspension was prepared. Human CD34+ cells were purified from fetal liver samples or from cord blood by density gradient centrifugation (Lymphocyte Separation Medium, MP Biomedicals) followed by positive immunomagnetic selection using anti-human CD34 microbeads according to the manufacturer's instructions (Miltenyi Biotec). Cells were either frozen in 10% DMSO containing FBS or injected directly.

Newborn pups (within first day of life) were sublethally irradiated (X-ray irradiation, 2×150 cGy 4 hours apart) and 100,000 to 200,000 CD34+ cells in 20 microliters of PBS were injected into the liver using a 22-gauge needle (Hamilton Company, Reno, Nev.).

All experiments were performed in compliance with Yale University Human Investigation Committee protocol and Yale Institutional Animal Care and Use Committee protocols.

TPO Expression. Serum concentrations of mouse and human TPO protein were measured by species-specific ELISA (RayBiotech) following the manufacturer's protocol.

To measure the expression of mouse and human mRNA encoding TPO, tissues were isolated from adult animals and total RNA was purified using TRIzol (Invitrogen) following the manufacturer's instructions. Contaminating genomic DNA was eliminated by treatment with RNase-Free DNase I (Roche) and the RNA was reverse-transcribed using SuperScript II reverse transcriptase (Invitrogen) and oligo-dT primers. The following primers were used for PCR amplification: mTpo forward, CCACCACCCA TGGATCTC (SEQ ID NO:1); mTpo reverse, AAAGCAGAAC ATCTGGAGCA G (SEQ ID NO:2); hTPO forward, CAGGACTGAA AAGGGAATCA (SEQ ID NO:3); hTPO reverse, CGTTGGAAGG CCTTGAATTT (SEQ ID NO:4); mRpl13a forward, GTACGCTGTG AAGGCATCAA (SEQ ID NO:5); mRpl13a reverse, ATCCCATCCA ACACCTTGAG (SEQ ID NO:6).

Figure 11D:
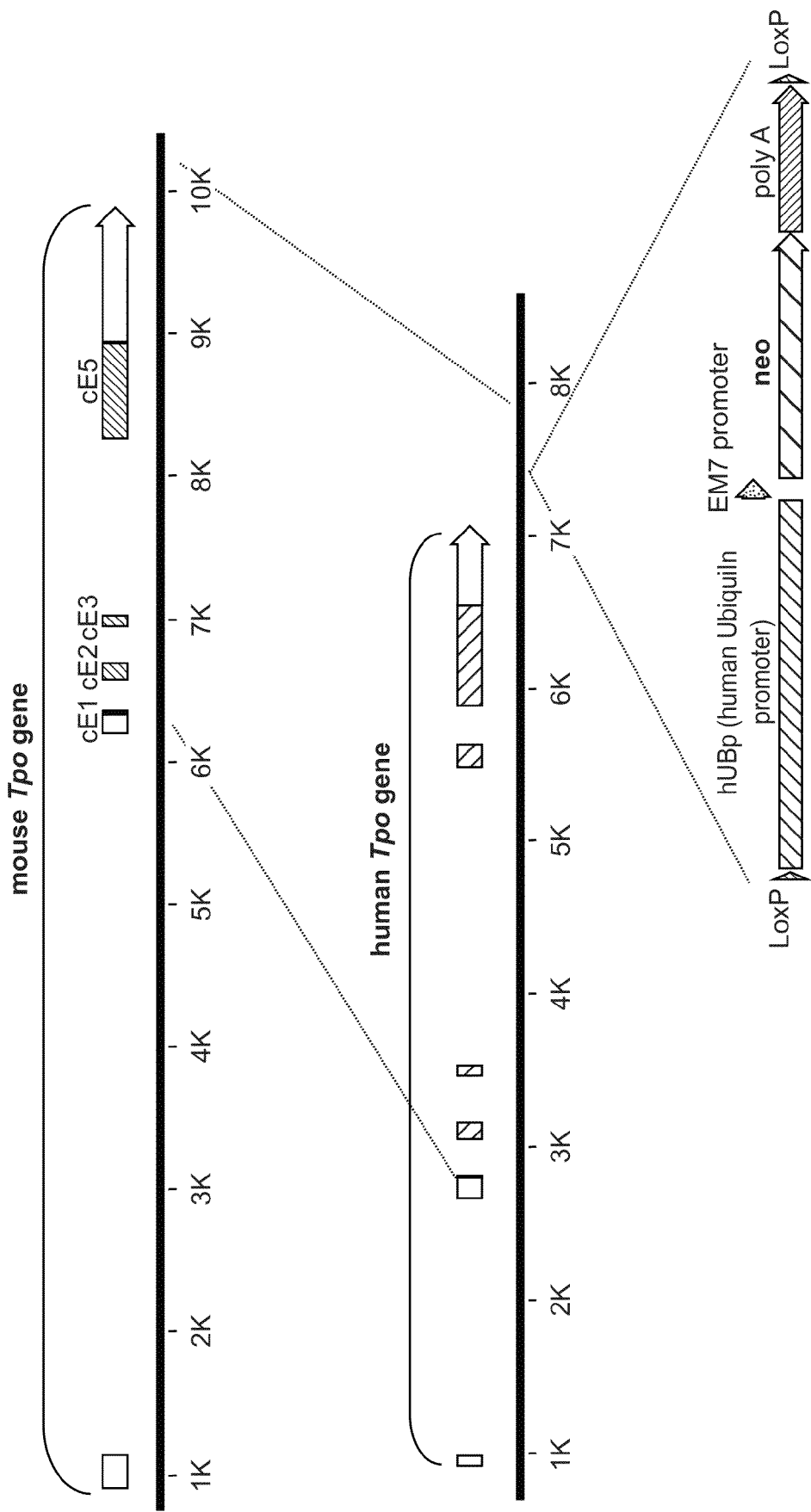
FIG. 11(*a*) shows RT-PCR analysis of mouse TPO (mTpo) and human TPO (hTPO) expression in different tissues of a $Rag2^{+/-}\gamma_c^{y/-}TPO^{h/m}$ mouse; (*b*) RT-PCR analysis of mTpo and hTPO expression in liver, kidney and mesenchymal multipotent stromal cells (MSCs) of $Rag2^{-/-}\gamma_c^{-/-}TPO^{m/m}$, $TPO^{h/m}$ and $TPO^{h/h}$ mice; (*c*) concentrations of mouse and human TPO proteins measured by ELISA in serum of $TPO^{m/m}$, $TPO^{h/m}$ and $TPO^{h/h}$ mice.

To determine whether human TPO is faithfully expressed in these mice, total RNA was extracted from a variety of organs from a TPO$^{h/m}$ mouse, and a similar pattern of expression for both mouse and human mRNA encoding TPO by RT-PCR was observed (FIG. 11(a)). Next, the expression in three tissues or cell types known to express TPO (liver, kidney and mesenchymal multipotent stroma cells) from TPO$^{m/m}$, TPO$^{h/m}$ and TPO$^{h/h}$ mice were compared. The expression of mouse Tpo in samples from TPO$^{m/m}$ and TPO$^{h/m}$ mice was detected, while human TPO was expressed in TPO$^{h/m}$ and TPO$^{h/h}$ (FIG. 11(b)). The concentrations of TPO protein in the serum of the targeted mice were also measured. Mouse TPO was detected in TPO$^{m/m}$ and TPO$^{h/m}$ animals, and human TPO in TPO$^{h/m}$ and TPO$^{h/h}$ (FIG. 11(c)). The concentrations measured for human TPO were approximately 10-fold lower than mouse TPO. However, this difference is compatible with the physiological concentrations reported in healthy human and mouse (FIG. 11(c)), and might be due to species-specific differences of cytokine half lives.

FIG. 11 shows (a) RT-PCR analysis of mouse TPO (mTpo) and human TPO (hTPO) expression in different tissues of a Rag2$^{+/-}$γ$_c^{y/-}$TPO$^{h/m}$ mouse; mouse Rpl13a was used as housekeeping gene; (b) RT-PCR analysis of mTpo and hTPO expression in liver, kidney and mesenchymal multipotent stromal cells (MSCs) of Rag2$^{-/-}$γ$_c^{-/-}$TPO$^{m/m}$, TPO$^{h/m}$ and TPO$^{h/h}$ mice;

(c) concentrations of mouse and human TPO proteins measured by ELISA in serum of TPO$^{m/m}$, TPO$^{h/m}$ and TPO$^{h/h}$ mice (in pg/ml, mean±S.D., n=7-9). ND: not detected; the normal ranges indicated are from R&D Systems, Thrombopoietin Quantikine kits.

Mesenchymal Multipotent Stroma Cell Isolation. For TPO studies, femur and tibia of mice were harvested and the bone marrow cells were flushed out. Bones were cut into small pieces and digested with collagenase P and D (10 μg/ml) for 45 minutes at 37° C. Bone associated cells were collected by repeated pipeting. Cells were cultured in the presence of MSC medium with stimulatory supplements (Stemcell Technologies) for 14 days. Hematopoietic lineage cells were removed from the culture through immunomagnetic cell sorting (MACS, Miltenyi Biotec) using CD45 and Ter119 antibodies. Non-hematopoietic cells (CD45-Ter119-) were cultured for 5 more days and MSC phenotype (CD45-Ter119-Sca1+ CD90+) was confirmed by FACS (Diminici et al. (2006) Minimal criteria for defining multipotent mesenchymal stromal cells, The International Society for Cellular Therapy position statement, *Cytotherapy* 8:315-317).

Analysis of Hematopoietic Cell Populations in TPO Mice. The mice were bled 8-12 weeks after transplantation. Red blood cells were lysed three times using ACK (Lonza), and the cells were stained with anti-mouse CD45 and anti-human CD45 antibodies. Animals in which at least 1% of CD45+ cells were of human origin, were used for further analysis. Approximately 80% of the transplanted mice reached this engraftment threshold, and no difference was noticed between the TPOm/m and TPOh/h groups.

The mice were sacrificed at 3-4 or 6-7 months after engraftment. Single cell suspensions were prepared from the bone marrow (flushed from 2 femurs and 2 tibias), spleen and thymus. Red blood cells were eliminated by ACK lysis and cells were stained for FACS analysis using the following antibodies. For overall hematopoietic engraftment: anti-mouse CD45-eFluor450 (30-F11, eBioscience) and anti-human CD45-APC-Cy7 (2D1). For human hematopoietic stem and progenitor cells and hematopoietic lineages: anti human CD14-PerCP (MoP9), CD19-APC (HIB19), CD33-APC (WM53), CD34-PE (AC136, Miltenyi Biotec), CD38-FITC (HIT2), CD41a-APC (HIPS) and CD66-FITC (B1.1).

For mouse stem and progenitor cell analysis, the anti-lineage cocktail contained biotinylated antibodies against CD3ε (145-2C11), CD11b (M1/70), CD11c (HL3), CD19 (1D3), Gr1 (RB6-8C5) and Ly-76 (Ter119). Cells were subsequently stained with streptavidin-APC-Cy7, anti cKit-APC (2B8) and anti Sca1-PE-Cy7 (D7).

All the antibodies were obtained from BD Biosciences, except otherwise specified. The data were acquired on a FACSCalibur™ or LSRII™ flow cytometer (BD Biosciences) and analyzed using the FlowJo™ software.

Functional Characterization of Human Hematopoietic Stem and Progenitor Cells in TPO Mice. Bone marrow cells from 3 to 7 engrafted mice were pooled and human CD34+ cells were purified by MACS depletion of mouse CD45+ cells (Miltenyi Biotec) followed by FACS sorting of human CD45+ CD34+ cells on a FACSAria™ flow cytometer (BD Biosciences).

To assess the colony forming capacity of human CD34+ cells, IMDM was supplemented with 20% FCS, 2 mM L-glutamine, 55 µM 2-mercaptoethanol (all reagents from GIBCO) mixed with Methocult™ H4100, 1% BSA (Stemcell Technologies) and the following human cytokines were added: SCF (10 ng/ml), FLT3l (10 ng/ml), TPO (50 ng/ml), IL-3 (20 ng/ml), IL-6 (10 ng/ml), IL-11 (10 ng/ml), GM-CSF (50 ng/ml), EPO (4 U/ml) (all from R&D systems). 100,000 to 150,000 sorted cells were plated on 60 mm petri dishes and incubated at 37° C., 5% $CO_2$ for 12-14 days. The number of colonies at 12-14 days was counted and categorized into specific myeloid lineage by microscopy.

For secondary transplantation experiments, 100,000 CD34+ cells purified from $TPO^{m/m}$ or $TPO^{h/h}$ primary recipients were injected into sublethally irradiated (2×200 cGy) $Rag2^{-/-}\gamma c^{-/-}TPO^{m/m}$ secondary recipients, as described above. These mice were sacrificed 8 weeks later and the percentage of human CD45+ cells in bone marrow was determined by FACS.

Statistical Analysis of TPO Mice Data. Data were compared using two-tailed unpaired t-test. When more than 2 samples were compared, one-way ANOVA followed by Tukey post hoc tests was performed. The proportions of engrafted mice in the secondary transplantation experiment were compared using Pearson's Chi squared test. Differences were considered significant when the p values were lower than 0.05.

Example 11 hTPO Engrafted Mice: Improved Human Engraftment Levels in $TPO^{h/h}$ Recipient Mice Bone Marrow Phenotyping of Bone Marrow of Humanized and Engrafted Mice. Cells isolated from bone marrow of humanized mice were analyzed by flow cytometry and showed statistically significant improvements in engraftment of total human hematopoietic cells, human hematopoietic stem cells, human myeloid cells, human and granulocytes relative to engraftment of non-humanized mice (La, RAG and Il2rg knockouts lacking humanization of TPO gene). See FIGS. 12 & 14.

$Rag2^{-/-}\gamma_c^{-/-}$ mice with wild-type Tpo ($TPO^{m/m}$), heterozygous ($TPO^{h/m}$) or homozygous ($TPO^{h/h}$) TPO gene replacement were prepared as described. Irradiated (2×1.5 Gy) newborn $Rag2^{-/-}\gamma_c^{-/-}TPO^{m/m}$ and $TPO^{h/h}$ mice were engrafted with human CD34+ cells purified from cord blood or fetal liver and analyzed engraftment in bone marrow 3-4 months or 6-7 months later.

FIG. 12 shows results of engraftment studies. FIG. 12(a) shows representative FACS analysis of human and mouse CD45+ cells in bone marrow of $Rag2^{-/-}\gamma_c^{-/-}TPO^{m/m}$ and $TPO^{h/h}$ mice 3 to 4 months after engraftment with human CD34+ cells. Results of two representative mice are shown for each genotype. Percentages of mouse and human CD45+ cells among the total (mouse+human) CD45+ cell populations are indicated. FIG. 12(b) shows percentages of human CD45+ cells in the bone marrow 3 to 4 months (left, n=42-53) or 6 to 7 months (right, n=20-25) after transplantation. Each symbol represents an individual mouse, horizontal bars indicate mean values. FIG. 12(c) shows absolute numbers of human CD45+ cells in the bone marrow of the same animals as in (b). P values indicate statistical significance.

Figure 12A:
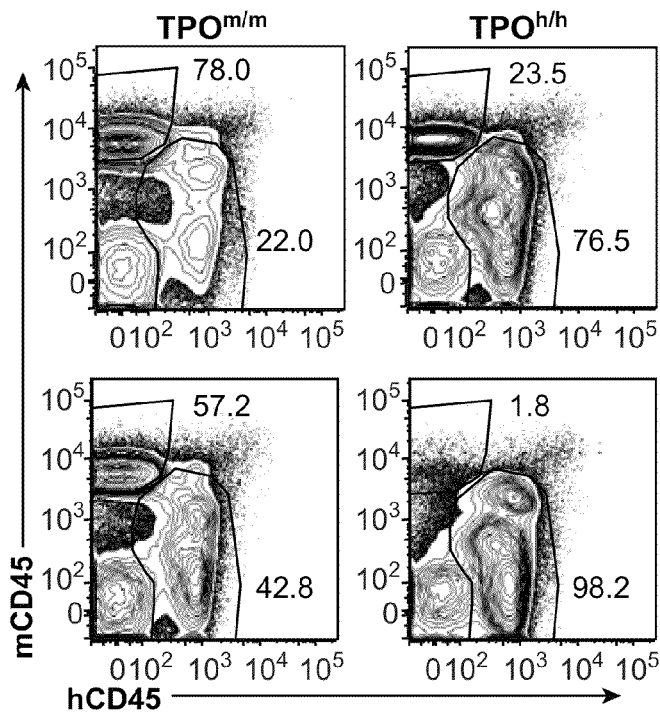
FIG. 12(*a*) shows FACS analysis of human and mouse CD45+ cells in bone marrow of $Rag2^{-/-}\gamma_c^{-/-}TPO^{m/m}$ and $TPO^{h/h}$ mice 3 to 4 months after engraftment with human CD34+ cells; (*b*) percentages of human CD45+ cells in the bone marrow 3 to 4 months (left) or 6 to 7 months (right) after transplantation; (c) absolute numbers of human CD45+ cells in the bone marrow of the same animals as in (b).
FIG. 12(d) shows the percentages of human CD45+ cells in the bone marrow of Rag2$^{-/-}\gamma_c^{-/-}$TPO$^{m/m}$ and TPO$^{h/h}$ mice, engrafted with human CD34+ cells isolated from cord blood (CB) or fetal liver (FL).
Figure 12B:
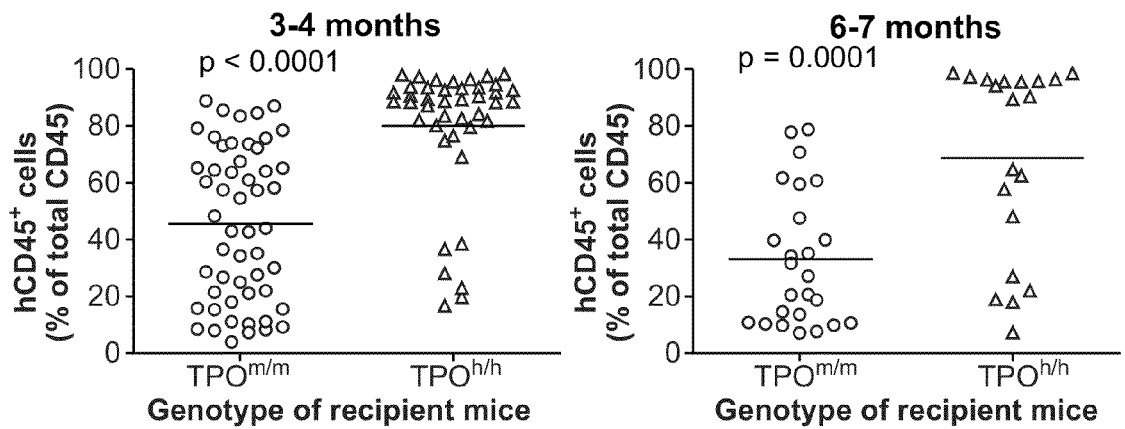
Figure 12C:
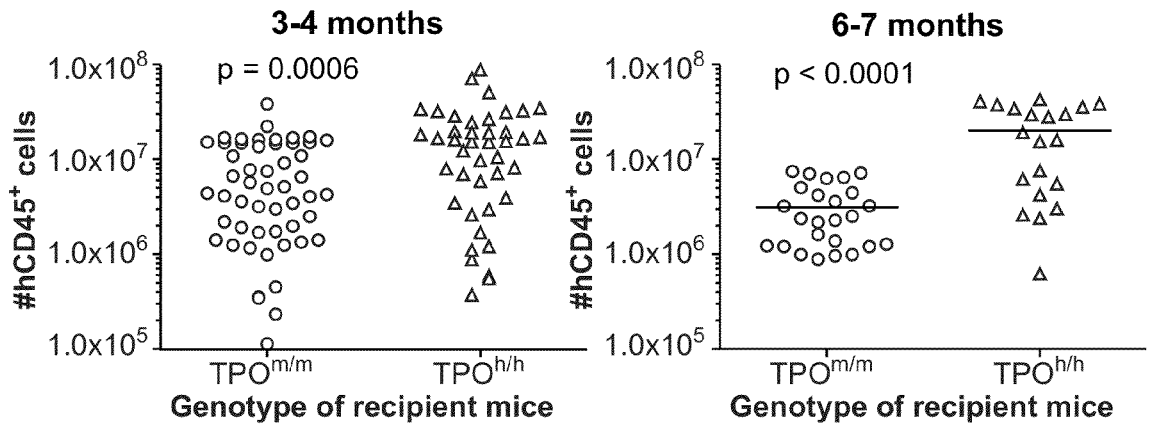
Figure 12D:
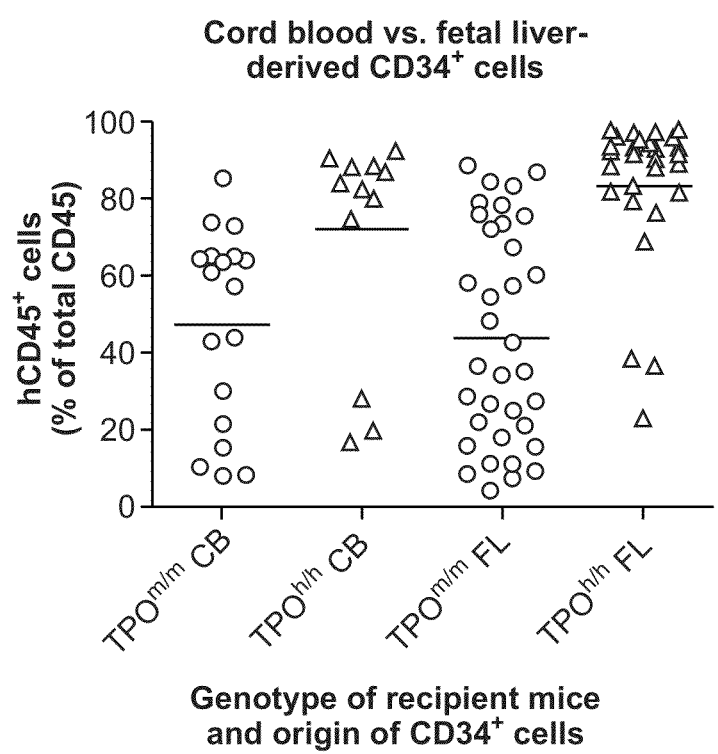

A significant increase was observed in the percentages (FIGS. 12(a) and 12(b)) and absolute numbers (FIG. 12(c)) of human hematopoietic cells (hCD45+) in bone marrow of $TPO^{h/h}$ compared to $TPO^{m/m}$ recipients at both time points. Furthermore, $TPO^{h/h}$ recipients displayed a lower engraftment variability, with an at least 80% human chimerism in 75% of the mice at 3-4 months (FIG. 12(b)). The source of the CD34+ cells did not affect this result, as a similar increase in chimerism in $TPO^{h/h}$ hosts was observed with cells derived from cord blood and from fetal liver (FIG. 12(d)). Interestingly, while numbers of human cells declined in $TPO^{m/m}$ hosts between the early and later time points, they remained constant in $TPO^{h/h}$ animals (FIG. 12(c)). These results are consistent with previously described functions of TPO in the mouse. First, TPO favors the expansion of HSCs after transplantation into irradiated recipient mice, leading to increased engraftment levels; second, it favors the maintenance of adult HSCs, leading to sustained hematopoiesis throughout adult life.

Example 12 hTPO Engrafted Mice: Effect of TPO Humanization on Mouse and Human Platelets

Platelet Analysis in TPO Mice. Platelet counts in peripheral blood were measured using a Hemavet™ 950FS machine (Drew Scientific). Blood samples were then stained with anti-mouse CD61-PE (2C9.G2) and anti-human CD41a-APC (HIPS), and the percentages of mouse and human platelets were determined by flow cytometry, without placing any gate on the size (FSC) or granulosity (SSC) of the cells. The absolute mouse and human platelet counts were calculated by multiplying these respective percentages with the absolute platelet counts.

As TPO is well known for its crucial function on thrombopoiesis, it was investigated whether TPO humanization affected platelet development. Humanization of both alleles of the TPO gene led to an approximately two-fold reduction in blood platelet counts of non-engrafted Rag2$^{-/-}$γ$_c$$^{-/-}$ mice (FIG. 13(a)). After engraftment with human cells, the counts of mouse platelets in TPO$^{h/h}$ mice were further decreased, to less than 25% of normal values (FIG. 13(d)). The ratio of human to mouse platelets (FIG. 13(b), 13(c)), as well as the absolute counts of human platelets (FIG. 13(e)), tended to be higher in TPO$^{h/h}$ mice than in TPO$^{m/m}$, but none of these differences reached statistical significance. Furthermore, the percentage of bone marrow megakaryocytes (CD41a$^+$ cells) among human cells was comparable in both strains (FIG. 13(f)). These results demonstrate that levels or biologic activity of human TPO reached by the knock-in strategy are not sufficient to fully replace mouse TPO function, and furthermore suggest that human TPO on its own is not sufficient to support human thrombopoiesis in the mouse environment.

FIG. 13(a) shows platelet counts in the blood of adult non-engrafted Rag2$^{-/-}$γ$_c$$^{-/-}$ TPO$^{m/m}$, TPO$^{h/m}$ and TPO$^{h/h}$ mice. p<0.0001 (one way ANOVA, n=7-17; the indicated p-values were calculated with the Tukey post hoc test). Each symbol represents an individual mouse, horizontal bars indicate mean values; (b) representative FACS analysis of mouse (mCD61$^+$) and human (hCD41a$^+$) platelets in the blood of Rag2$^{-/-}$γ$_c$$^{-/-}$TPO$^{m/m}$ and TPO$^{h/h}$ mice 3 to 4 months after engraftment. The numbers indicate percentages among total events; (c) human platelet chimerism, determined by FACS, in TPO$^{m/m}$ and TPO$^{h/h}$ mice (n=19-22). Only mice with a percentage of human CD45$^+$ cells in the blood higher than 5% were included in this analysis; (d),(e) counts of mouse (mCD61$^+$, (d)) and human (hCD41a$^+$, (e)) platelets in the blood of TPO$^{m/m}$ and TPO$^{h/h}$ recipients; (f) human megakaryocyte percentages (CD41a$^+$) among human CD45$^+$ cells in the bone marrow.

FIG. 13(g)-(i) show human engraftment levels in secondary lymphoid organs. FIG. 13 (g),(h) provides percentages of human CD45$^+$ cells in blood (20 g; n=43-53) and spleen (13 h; n=35-36) of Rag2$^{-/-}$γ$_c$$^{-/-}$TPO$^{m/m}$ and TPO$^{h/h}$ mice (each symbol represents an individual mouse, horizontal bars indicate mean values); (i) shows total cellularity of the thymi of engrafted TPO$^{m/m}$ and TPO$^{h/h}$ recipients (n=24-34). More than 90% of the cells found in the thymus were of human origin (hCD45$^+$).

Example 13 hTPO Engrafted Mice: Multi-lineage Hematopoiesis in TPO-Humanized Mice

Phenotyping of Blood Cells of Humanized and Engrafted Mice. Cells isolated from blood of humanized mice were analyzed by flow cytometry and showed statistically significant improvements in engraftment of human monocytes and granulocytes relative to engraftment of non-humanized mice (i.e., RAG and Il2rg knockouts lacking humanization of TPO gene). See FIG. 14.

It was investigated whether human TPO could favor multilineage differentiation of human hematopoietic stem and progenitor cells in vivo. As previously reported (Traggiai et al.; Ishikawa et al. (2005) Development of functional human blood and immune systems in NOD/SCID/IL2 receptor gamma chain(null) mice, *Blood* 106:1565-1573)), the engrafted human cells gave rise mostly to B cells (CD19$^+$) in wild-type Rag2$^{-/-}$γ$_c$$^{-/-}$ hosts (61.51±4.71% of the human cells in the spleen, mean±sem, n=32), with only a small fraction of myeloid cells. When TPO$^{m/m}$ and TPO$^{h/h}$ recipients were compared, a significant increase in frequency of CD33+ myeloid cells in the bone marrow of TPO$^{h/h}$ mice was observed (FIGS. 14(a) and 14(b)). Interestingly, this increase was mostly due to granulocytes (CD33$^+$CD66$^{hi}$SSC$^{hi}$ cells), while the fraction of monocytes (CD33$^{hi}$CD66$^{lo}$CD14$^+$) was similar in both strains (FIG. 14(a),(c),(d),(e)). The percentage of myeloid cells (both granulocytes and monocytes) was also significantly increased in the peripheral blood of TPO$^{h/h}$ animals (FIG. 14(a),(f), and (g)).

Figure 14A:
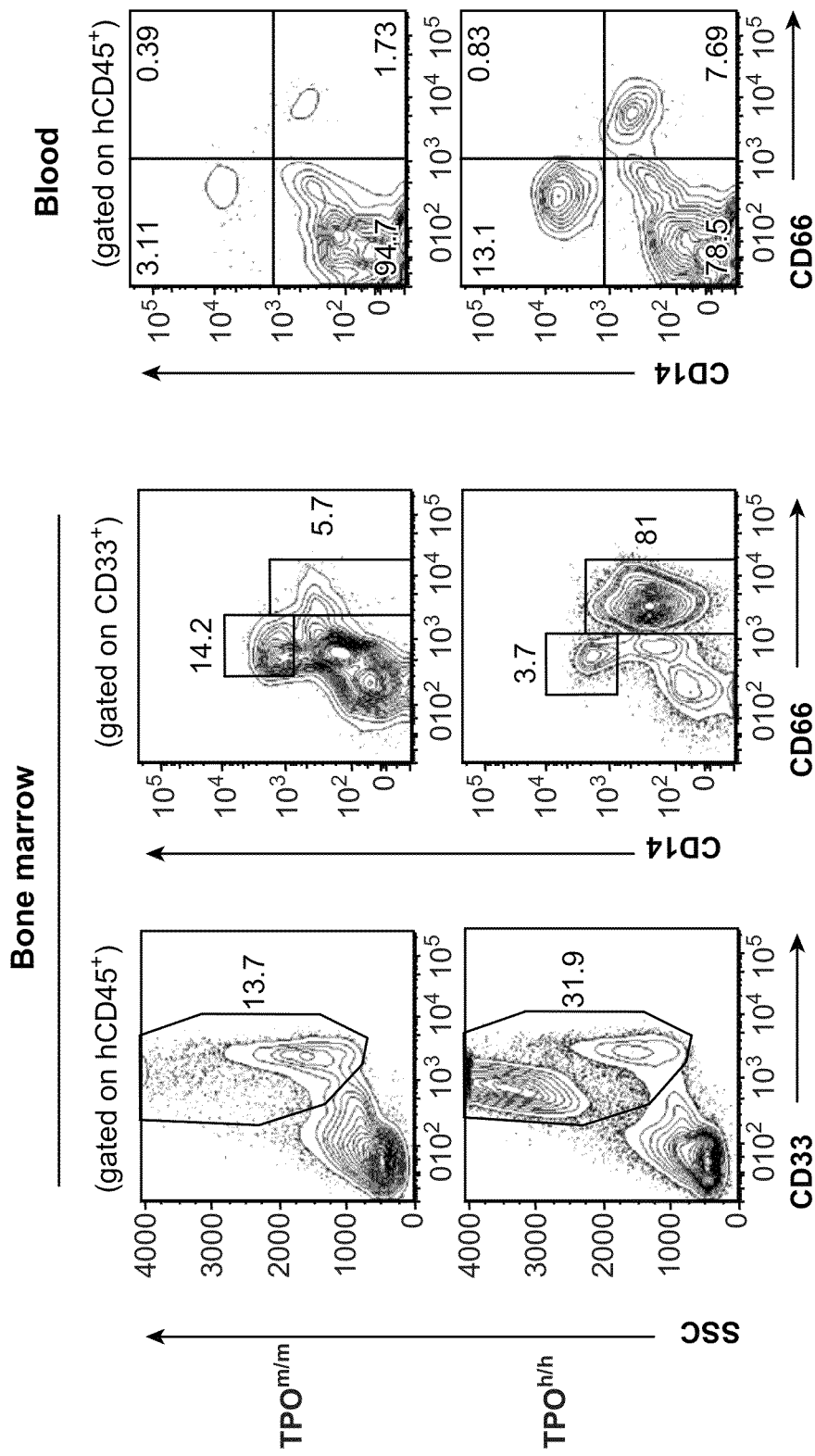
FIG. 14(a) shows FACS analysis of human myeloid cell populations in bone marrow and blood of Rag2$^{-/-}\gamma_c^{-/-}$TPO$^{m/m}$ and TPO$^{h/h}$ mice 3 to 4 months after engraftment; (b) total myeloid populations (CD33+ cells); (c) granulocytes (CD33+CD66$^{hi}$); (d) DiffQuick™ staining of hCD45+SS-C$^{hi}$CD33+CD66$^{hi}$ cells purified from the bone marrow of TPO$^{h/h}$ recipients; (e) monocytes (CD33+CD66$^{lo}$CD14+); (f),(g) analysis of human myeloid cell populations relative to total human CD45+ cell chimersim in blood of Rag2$^{-/-}\gamma_c^{-/-}$TPO$^{m/m}$ and TPO$^{h/h}$ recipients; (f) granulocytes (CD66+); (g) monocytes (CD14+).

FIG. 14(a)-(g) depicts improved multilineage hematopoiesis in hTPO mice as measured by CD33$^+$, CD66$^+$, CD14$^+$ cells in engrafted TPO$^{m/m}$ and TPO$^{h/h}$ mice. FIG. 14(a) shows representative FACS analysis of human myeloid cell populations in bone marrow and blood of Rag2$^{-/-}$γ$_c$$^{-/-}$TPO$^{m/m}$ and TPO$^{h/h}$ mice 3 to 4 months after engraftment. The numbers indicate the percentages among the indicated gated cell populations. FIGS. 14(b)-(e) show analysis of human myeloid cell populations relative to total human CD45$^+$ cell chimerism in bone marrow of Rag2$^{-/-}$γ$_c$$^{-/-}$TPO$^{m/m}$ and TPO$^{h/h}$ recipients (n=19). FIG. 14(b) provides total myeloid populations (CD33+ cells). FIG. 14(d) provides granulocytes (CD33$^+$ CD66$^{hi}$), FIG. 14(c) shows Diff-Quick™ staining of hCD45$^+$ SSC$^{hi}$CD33$^+$CD66$^{hi}$ cells purified from the bone marrow of TPO$^{h/h}$ recipients. FIG. 14(e) shows monocytes (CD33$^+$ CD66$^{lo}$CD14$^+$). Each symbol represents an individual mouse, horizontal bars indicate mean values. FIGS. 14(f) and (g) show analysis of human myeloid cell populations relative to total human CD45$^+$ cell chimersim in blood of Rag2$^{-/-}$γ$_c$$^{-/-}$TPO$^{m/m}$ and TPO$^{h/h}$ recipients (n=6-7); FIG. 14(f): granulocytes (CD66$^+$); FIG. 14(g): monocytes (CD14$^+$).

Example 14 hTPO Engrafted Mice: Humanization Effect on Mouse and Human Hematopoietic Stem and Progenitor Cells The effect of human TPO on the number and function of HSCs and progenitor cells themselves was analyzed. Genetic deletion of TPO leads to a reduction of HSCs in adult mice. To determine whether TPO humanization could affect the mouse population immunophenotypically defined as containing mouse HSCs, the percentages of lineage-negative Sca1$^+$ c-Kit$^+$ cells in bone marrow of non-engrafted TPO$^{m/m}$, TPO$^{h/m}$ and TPO$^{h/h}$ adult mice were compared.

Figures 15F, 15G, 15H:
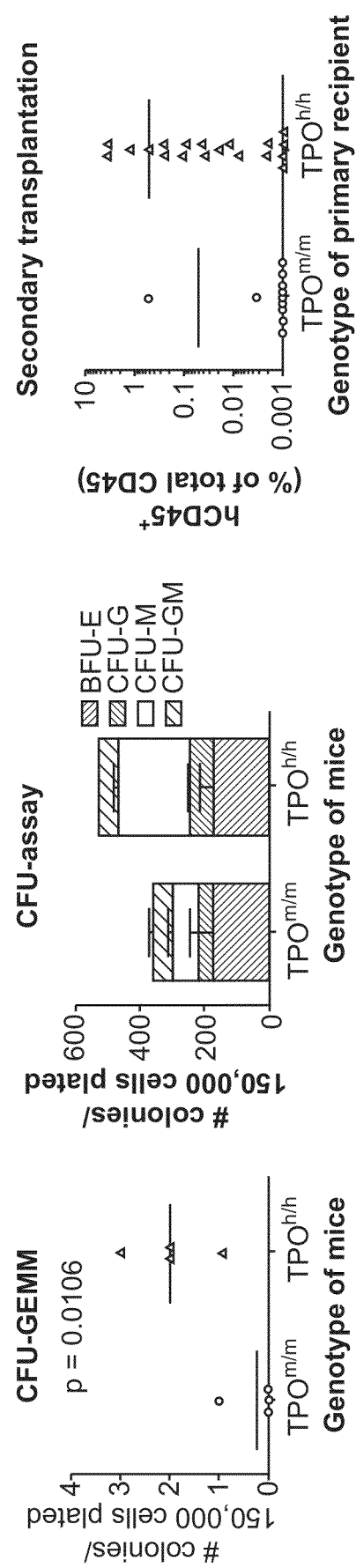
FIG. 15(a) shows FACS analysis of mouse Lin− Sca1+ c-Kit+ stem and progenitor cells in the bone marrow of non-engrafted Rag2$^{-/-}\gamma_c^{-/-}$TPO$^{h/m}$ and TPO$^{h/h}$ mice compared to WT TPO (TPO$^{m/m}$) Rag2$^{-/-}\gamma_c^{-/-}$ mice; (b) quantitative analysis of the results presented in (a); (c) FACS analysis of human CD34+CD38− cells in the bone marrow of Rag2$^{-/-}\gamma_c^{-/-}$TPO$^{m/m}$ and TPO$^{h/h}$ mice 3 to 4 months after engraftment; (d) quantitative analysis of the percentages of CD38− cells in the human CD45+CD34+ population in TPO$^{m/m}$ and TPO$^{h/h}$ recipient mice; (e) human CD34+CD38− cells in the bone marrow of the same mice as in 15(d); (f),(g) methylcellulose colony formation assay with human CD45+CD34+ cells purified from Rag2$^{-/-}\gamma_c^{-/-}$TPO$^{m/m}$ and TPO$^{h/h}$ recipients; (f) is CFU-GEMM, (g) is BFU-E (black), CFU-G (white), CFU-M (gray) and CFU-GM (dashed); (h) human CD45+ chimerism in secondary transplant of human CD45+CD34+ cells from Rag2$^{-/-}\gamma_c^{-/-}$TPO$^{m/m}$ and TPO$^{h/h}$ mice into newborn Rag2$^{-/-}\gamma_c^{-/-}$ mice.

FIG. 15 shows decreased mouse lin$^-$ c-Kit$^+$Sca1$^+$ cells and increased number and self-renewal potential of human stem and progenitor cells in bone marrow of human TPO knock-in mice. FIG. 15(a) shows representative results of FACS analysis of mouse Lin$^-$Sca1+ c-Kit$^+$ stem and progenitor cells in the bone marrow of non-engrafted Rag2$^{-/-}$γ$_c$$^{-/-}$TPO$^{h/h}$ and TPO$^{h/h}$ mice compared to WT TPO (TPO$^{m/m}$) Rag2$^{-/-}$γ$_c$$^{-/-}$ mice. Numbers indicate the percentage of Sca1+ c-Kit$^+$ cells among the Lin$^-$ population. FIG. 15(b) shows quantitative analysis of the results presented in (a). p=0.0006 (one way ANOVA; the indicated p-values were calculated with the Tukey post hoc test; n=5/per genotype and the presented results are representative of 2 independent experiments). Each symbol represents an individual mouse, horizontal bars indicate mean values. FIG. 15(c) shows representative FACS analysis of human CD34$^+$CD38$^-$ cells in the bone marrow of Rag2$^{-/-}$γ$_c$$^{-/-}$TPO$^{m/m}$ and TPO$^{h/h}$ mice 3 to 4 months after engraftment. The numbers indicate the percentage of CD38$^-$ cells among the human CD45$^+$CD34$^+$ cells. FIG. 15(d) shows quantitative analysis of the percentages of CD38$^-$ cells in the human CD45$^+$CD34+ population in TPO$^{m/m}$ and TPO$^{h/h}$ recipient mice (n=43-53). FIG. 15(e) shows absolute numbers of human CD34$^+$CD38$^-$ cells in the bone marrow of the same mice as in 15(d)d. FIGS. 15(f) and (g) show methylcellulose colony formation assay with human CD45$^+$CD34$^+$ cells purified from Rag2$^{-/-}\gamma_c^{-/-}$TPO$^{m/m}$ and TPO$^{h/h}$ recipients. FIG. 15(f) is CFU-GEMM, FIG. 15(g) is BFU-E (black), CFU-G (white), CFU-M (gray) and CFU-GM (dashed). CD34$^+$ cells were pooled from groups of 3-4 mice, 4 independent pools per genotype of recipient mice. In FIG. 15(h) human CD45$^+$CD34$^+$ cells were purified from Rag2$^{-/-}\gamma_c^{-/-}$ TPO$^{m/m}$ and TPO$^{h/h}$ primary recipient mice, transplanted into newborn Rag2$^{-/-}\gamma_c^{-/-}$ mice (100,000 cells per mouse), and human CD45+ chimerism was determined in secondary recipients 8 weeks later. The results are pooled from two independent experiments (n=7-12 primary recipients, n=11-19 secondary recipients).

A significant reduction in the percentage of these cells in both TPO$^{h/m}$ and TPO" mice compared to TPO$^{m/m}$ was observed (FIG. 15(b)), suggesting that human TPO is either not fully cross-reactive on the mouse receptor or is not available in sufficient amounts to mouse cells in this knock-in setting.

Human CD34$^+$ populations in the bone marrow of engrafted TPO$^{m/m}$ and TPO" hosts were characterized. Human HSCs with long-term repopulating potential are contained in the Lin-CD34$^+$CD38$^-$ cell fraction. The percentage of CD34$^+$ cells among the human CD45$^+$ population was slightly increased in TPO$^{h/h}$ mice (12.39±0.79% vs. 10.00±0.81%, mean±sem, n=43-53, p=0.037). A small (1.5 fold) but statistically significant increase was observed in the percentage of CD38$^-$ cells within the CD34$^+$ population in TPO$^{h/h}$ compared to TPO$^{m/m}$ recipients (FIG. 15(c),(d)). Overall, this resulted in a significant increase (approximately 2.8-fold) of absolute numbers of CD34$^+$CD38$^-$ cells in TPO-humanized mice (FIG. 15(e)). Thus, based on cell surface immunophenotype, human TPO favors a population of cells known to be highly enriched for HSCs.

To address the functional properties of this cell population, human CD34$^+$ cells were purified from the bone marrow of TPO$^{m/m}$ and TPO$^{h/h}$ mice, and assessed in methylcellulose colony formation assays in vitro. CFU-GEMM are multilineage myeloid colonies derived from immature cells that at least contain all erythro-megakaryocyte and myeloid cell differentiation potential. The formation of CFU-GEMM was detected, albeit in small numbers, from all four samples of CD34$^+$ cells isolated from TPO$^{h/h}$ recipient mice, while only one sample from TPO$^{m/m}$ generated CFU-GEMM (FIG. 15(f)). This result demonstrates improved maintenance of immature human hematopoietic progenitor cells in TPO$^{h/h}$ recipients. Furthermore, consistent with enhanced myeloid differentiation observed in vivo (FIG. 14), the numbers of CFU-M were also significantly higher in human CD34$^+$ cell samples isolated from TPO$^{h/h}$ compared to TPO$^{m/m}$ mice (225.0±12.25 vs. 81.25±10.80 colonies per 150,000 CD34$^+$ cells plated, mean±sem, p=0.0001; FIG. 15(g)).

Maintenance and/or self-renewal of HSCs is best demonstrated functionally by successful secondary transplants. SCID repopulating cells (SRCs) that serially engraft in mice represent currently the surrogate experimental gold standard for human HSC function. Thus, human CD34$^+$ cells were purified from bone marrow of TPO$^{m/m}$ and TPO$^{h/h}$ primary recipients and transplanted in equally low numbers (100,000 CD34$^+$ cells per animal) into Rag2$^{-/-}\gamma_c^{-/-}$ newborn mice. Bone marrow of secondary recipients was analyzed 8 weeks later (FIG. 15(h)). Human CD34$^+$ cells isolated from TPO$^{m/m}$ primary recipients had a very low capacity to serially engraft, as human CD45$^+$ cells were detected in only 2 of 11 secondary recipients. By contrast, human CD45$^+$ cells were present in the bone marrow of 15 of 19 mice engrafted with CD34+ cells isolated from TPO$^{h/h}$ primary recipients (p=0.0012). As the genotype of the secondary recipient mice was the same for both groups (TPO$^{m/m}$), this result indicates that the presence of human TPO in the primary recipient favored the maintenance of human cells with enhanced self-renewal capacity.

Taken together, these results demonstrate that homozygous TPO-humanized mice represent a better environment to maintain self-renewal capacity and multilineage differentiation potential of human hematopoietic stem and progenitor cells.

Persons skilled in the art can devise various arrangements that, although not explicitly described or shown in this disclosure, embody the invention and are included within its spirit and scope. All examples are provided to help the reader understand the principles and concepts of the invention and are used without limitation to the specific examples and embodiments described. All principles, aspects, embodiments, and examples of the invention are intended to encompass equivalents thereof, whether the equivalents are now known or developed in the future. The scope of the present invention is not intended to be limited to the embodiments and examples shown and described in this disclosure.

We claim:

1. A genetically modified mouse, wherein the mouse is null for a RAG gene and null for the mouse IL2Rγ gene, and comprises a replacement of a mouse IL-3 gene with a human IL-3 gene at the mouse IL-3 locus, a replacement of a mouse GM-CSF gene with a human GM-CSF gene at the mouse GM-CSF locus, a human hemato-lymphoid system, and a S. typhi infection, wherein the S. typhi infection is maintained for one week or more following exposure to S. typhi.

2. The mouse according to claim 1, wherein the S. typhi infection is a systemic infection.

3. A method for identifying an agent that inhibits S. typhi infection, the method comprising:
   infecting a genetically modified mouse with S typhi, wherein the genetically modified mouse is null for a RAG gene and null for the mouse IL2Rγ gene, and comprises a replacement of a mouse IL-3 gene with a human IL-3 gene at the mouse IL-3 locus, a replacement of a mouse GM-CSF gene with a human GM-CSF gene at the mouse GM-CSF locus, and a human hemato-lymphoid system;
   administering a candidate S. typhi inhibitor to the genetically modified mouse; and
   detecting an amount of S. typhi in the genetically modified mouse;
   wherein less S. typhi in the genetically modified mouse following administration of the candidate S. typhi inhibitor as compared with the amount of S. typhi in a matched S. typhi-infected mouse not administered the candidate S. typhi inhibitor indicates that the candidate S. typhi inhibitor inhibits a S. typhi infection.

4. The method according to claim 3, wherein the candidate S. typhi inhibitor is a drug, and the administering occurs after the infecting.

5. The method according to claim 3, wherein the candidate S. typhi inhibitor is a vaccine, and the administering occurs before the infecting.

6. The method according to claim 5, wherein the vaccine comprises a S. typhi cell surface protein or immunogenic fragment thereof.

7. The method according to claim 5, wherein the vaccine comprises membrane fraction of a S. typhi strain.

8. The method according to claim 5, wherein the vaccine comprises a recombinant S. typhi protein or immunogenic fragment thereof.

9. The method according to claim 5, wherein the vaccine comprises an expression vector that encodes a S. typhi protein or immunogenic fragment thereof.

10. The method according to claim 5, wherein the vaccine comprises an inactivated S. typhi strain or inactivated mixture of S. typhi strains.

11. The method according to claim 3, wherein the detecting comprises ascertaining the number of colony forming units per unit of blood or tissue from the genetically modified mouse.

12. A genetically modified mouse, wherein the mouse is null for a mouse RAG gene and null for the mouse IL2Rγ gene, and comprises a replacement of a mouse IL-3 gene with a human IL-3 gene at the mouse IL-3 locus, a replacement of a mouse GM-CSF gene with a human GM-CSF gene at the mouse GM-CSF locus, a human hemato-lymphoid system, and a M. tuberculosis infection, wherein the mouse comprises a granuloma that comprises a human immune cell.

13. A method for identifying an agent that inhibits a *M. tuberculosis* infection, the method comprising:
  infecting a genetically modified mouse with *M. tuberculosis*, wherein the genetically modified mouse is null for a RAG gene and null for the mouse IL2Rγ gene, and comprises a replacement of a mouse IL-3 gene with a human IL-3 gene at the mouse IL-3 locus, a replacement of a mouse GM-CSF gene with a human GM-CSF gene at the mouse GM-CSF locus, and a human hematolymphoid system;
  administering a candidate *M. tuberculosis* inhibitor to the genetically modified mouse; and
  detecting the number and/or size of granuloma in the genetically modified mouse;
  wherein a smaller granuloma or less granulomas in the genetically modified mouse following administration of the candidate *M. tuberculosis* inhibitor as compared with a size or number of granuloma in a matched *M. tuberculosis*-infected genetically modified mouse not administered the candidate *M. tuberculosis* inhibitor indicates that the candidate *M. tuberculosis* inhibitor inhibits a *M. tuberculosis* infection.

14. The method according to claim 13, wherein the candidate *M. tuberculosis* inhibitor is a drug, and the administering occurs after the infecting.

15. The method according to claim 13, wherein the candidate *M. tuberculosis* inhibitor is a vaccine, and the administering occurs before the infecting.

16. The method according to claim 13, wherein the granuloma is a lung granuloma.

* * * * *